(12) United States Patent
Sugio et al.

(10) Patent No.: US 8,430,510 B2
(45) Date of Patent: Apr. 30, 2013

(54) NOISE REDUCTION DEVICE, ELECTRO-OCULOGRAPHY MEASURING DEVICE, OPHTHALMOLOGICAL DIAGNOSIS DEVICE, EYE-GAZE TRACKING DEVICE, WEARABLE CAMERA, HEAD-MOUNTED DISPLAY, ELECTRONIC EYEGLASSES, NOISE REDUCTION METHOD, AND RECORDING MEDIUM

(75) Inventors: Toshiyasu Sugio, Osaka (JP); Daisuke Sato, Osaka (JP)

(73) Assignee: Panasonic Corporation, Osaka (JP)

( * ) Notice: Subject to any disclaimer, the term of this patent is extended or adjusted under 35 U.S.C. 154(b) by 316 days.

(21) Appl. No.: 12/945,005

(22) Filed: Nov. 12, 2010

(65) Prior Publication Data

US 2011/0170066 A1  Jul. 14, 2011

(30) Foreign Application Priority Data

Nov. 19, 2009 (JP) .................................. 2009-263713

(51) Int. Cl.
*A61B 3/14* (2006.01)
*A61B 3/00* (2006.01)
*A61B 3/10* (2006.01)

(52) U.S. Cl.
USPC ............ 351/209; 351/200; 351/205; 351/221

(58) Field of Classification Search .................. 351/209, 351/200, 205, 105, 243, 221, 222, 246
See application file for complete search history.

(56) References Cited

U.S. PATENT DOCUMENTS

| | | | |
|---|---|---|---|
| 2008/0188777 A1* | 8/2008 | Bedziouk et al. | 600/595 |
| 2009/0214485 A1* | 8/2009 | Gavrilova et al. | 424/93.7 |
| 2010/0191140 A1* | 7/2010 | Terada et al. | 600/544 |
| 2012/0081666 A1* | 4/2012 | Kiderman et al. | 351/210 |

FOREIGN PATENT DOCUMENTS

| | | |
|---|---|---|
| JP | 9-34631 | 2/1997 |
| JP | 11-85384 | 3/1999 |
| JP | 11-276461 | 10/1999 |
| JP | 2002-272693 | 9/2002 |

OTHER PUBLICATIONS

Hiroyuki Manabe et al., Full-time Wearable Headphone-Type Gaze Detector, Interaction 2006, pp. 23-24, 2006 (with English translation).

* cited by examiner

*Primary Examiner* — Dawayne A Pinkney

(74) *Attorney, Agent, or Firm* — Wenderoth, Lind & Ponack, L.L.P.

(57) ABSTRACT

A noise reduction device includes: a saccade information obtaining unit that obtains saccade information from an electro-oculography original signal that indicates an electro-oculogram resulting from an eye movement of a user, the saccade information relating to a saccadic movement which is a rapid eyeball movement; a control unit that determines a filter property for reducing noise included in the electro-oculography original signal, on the basis of the saccade information obtained by the saccade information obtaining unit; and a filtering unit that reduces the noise included in the electro-oculography original signal using the filter property determined by the control unit, to output an electro-oculography signal.

21 Claims, 65 Drawing Sheets

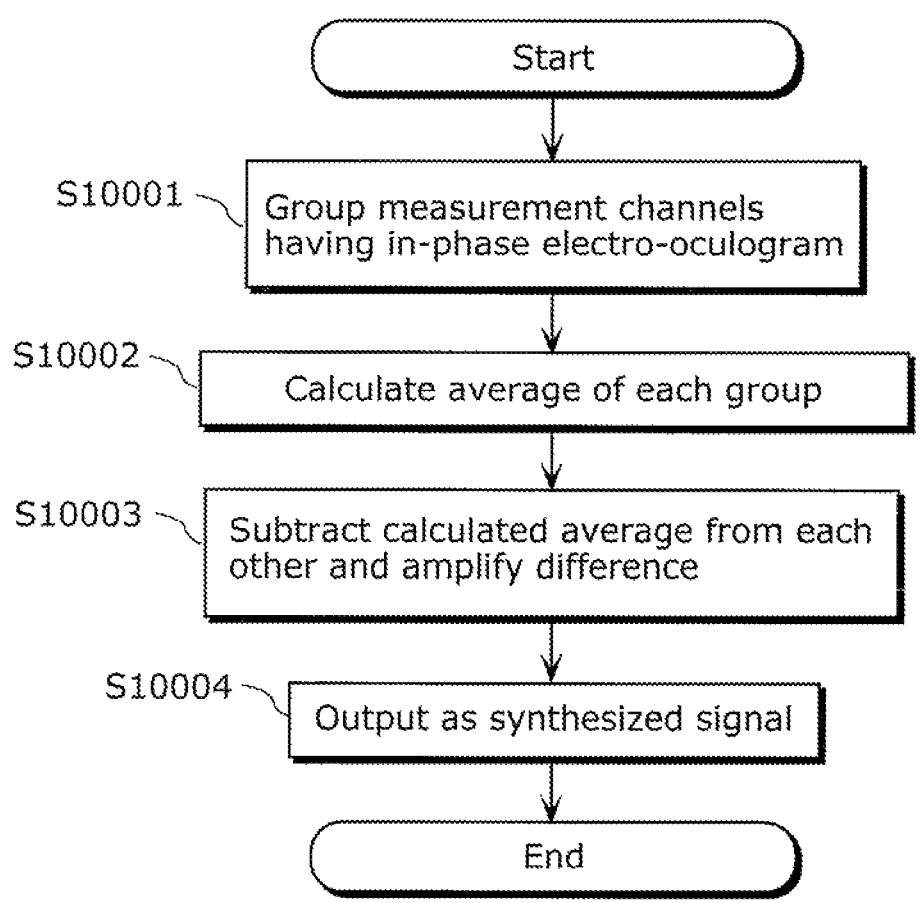

FIG. 51A

| Electro-oculography change amount | Eyeball movement angle |
|---|---|
| 5V | 40° |
| 4.5V | 30° |
| 4V | 20° |
| ... | ... |
| -5V | -40° |

FIG. 51B

| Electro-oculography change amount | Gaze point |
|---|---|
| 5V | (600,0) |
| 4.5V | (500,0) |
| 4V | (400,0) |
| ... | ... |
| -5V | (-600,0) |

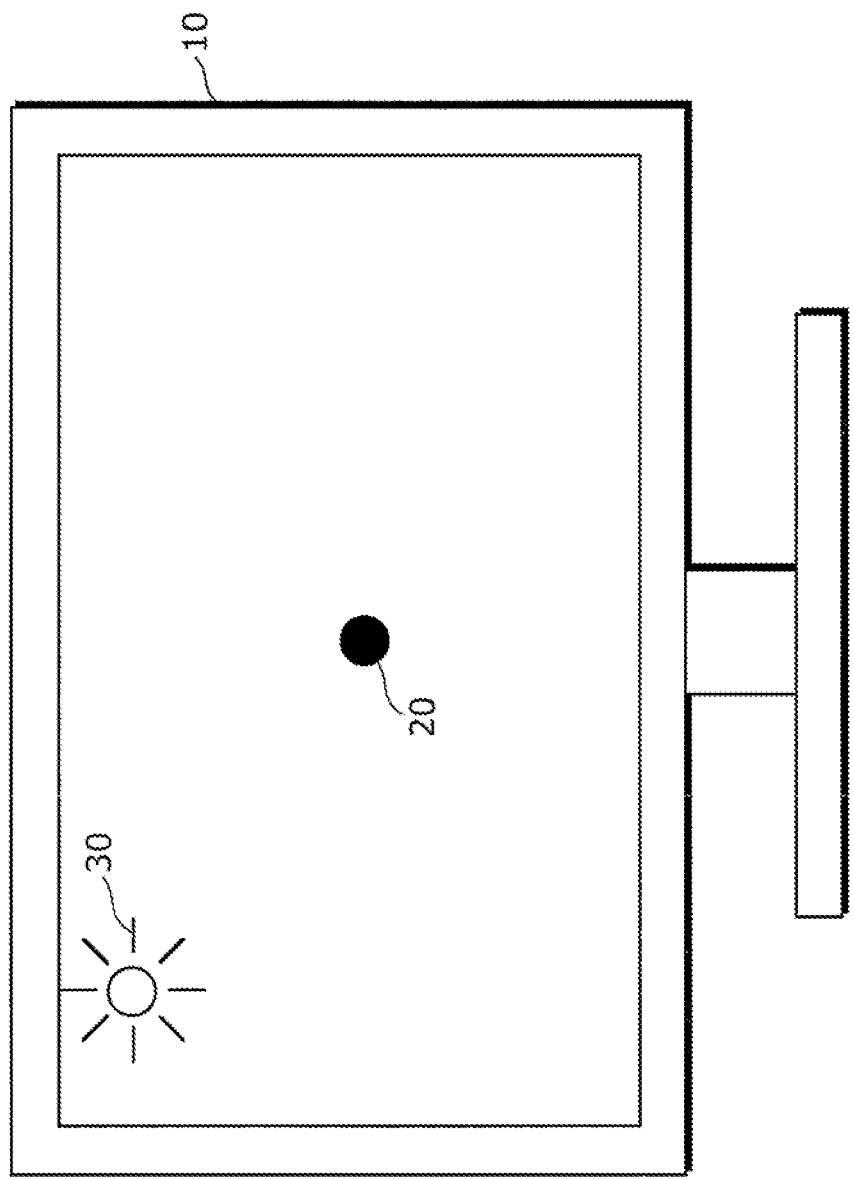

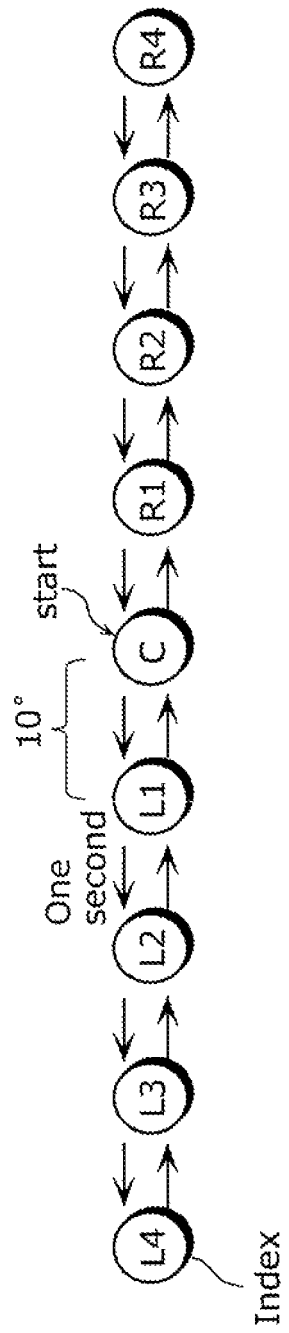

NOISE REDUCTION DEVICE, ELECTRO-OCULOGRAPHY MEASURING DEVICE, OPHTHALMOLOGICAL DIAGNOSIS DEVICE, EYE-GAZE TRACKING DEVICE, WEARABLE CAMERA, HEAD-MOUNTED DISPLAY, ELECTRONIC EYEGLASSES, NOISE REDUCTION METHOD, AND RECORDING MEDIUM

BACKGROUND OF THE INVENTION (1) Field of the Invention

The present invention relates to an electro-oculography measuring device that can output an electro-oculography signal by removing noise from an electro-oculography original signal.

(2) Description of the Related Art

The present invention relates to a noise reduction device and method for reducing noise that occurs when measuring an electro-oculogram of a human.

In recent years, EOG that utilizes a potential generated between a cornea and a retina has been proposed as a method for detecting an eye movement of a human.

EOG mentioned here is an eye movement detection method based on the fact that the human cornea is charged positively with respect to the retina. In detail, electrodes are placed near a human eyeball, and an eye movement is detected from a change in potential measured from the electrodes. FIGS. 63A and 63B show an example of the eye movement detection method employing EOG. The case where the electrodes are placed at two positions that are to the right and left of the right eye of the user at the same distance away from the center of the eyeball is shown as an example.

Let $V_a$ be an electro-oculogram generated on an electrode A placed to the right, and $V_b$ be an electro-oculogram generated on an electrode B placed to the left. When the eyeball of the user is positioned at the center as shown in FIG. 63A, $V_a$ and $V_b$ are equal, so that a measured electro-oculogram $V_{a-b}$ is 0 V. On the other hand, when the user looks to the right as shown in FIG. 63B, the electrode A is closer to the cornea of the right eye and accordingly $V_a > V_b$, so that the measured electro-oculogram $V_{a-b}$ is a plus value. Conversely, when the user looks to the left, $V_a < V_b$, so that the measured electro-oculogram $V_{a-b}$ is a minus value. That is, the plus value of the measured electro-oculogram $V_{a-b}$ indicates that the user has moved the eye to the right, and the minus value of the measured electro-oculogram $V_{a-b}$ indicates that the user has moved the eye to the left. In EOG, the user's eye movement is detected by utilizing such a change in measured electro-oculogram $V_{a-b}$.

When detecting the eye movement using EOG in this way, noise included in a generated electro-oculography signal needs to be reduced in order to increase detection accuracy. As an example of a noise reduction method, the following technique is described in Patent Literature 1.

In the noise reduction method disclosed in Patent Literature 1, first the user is instructed to gaze at a specified position, and an electro-oculography signal during this time is measured. Such an electro-oculography signal in a state where eye movements are intentionally reduced is treated as drift noise. In subsequent measurement, a signal corresponding to the drift noise is subtracted from a measured electro-oculography signal.

CITATION LIST

Patent Literature

[Patent Literature 1] Japanese Unexamined Patent Application Publication No. 11-85384
[Patent Literature 2] Japanese Unexamined Patent Application Publication No. 11-276461
[Patent Literature 3] Japanese Unexamined Patent Application Publication No. 9-034631
[Patent Literature 4] Japanese Unexamined Patent Application Publication No. 2002-272693

Non-Patent Literature

[Non-patent Literature 1] "Full-time Wearable Headphone-type Gaze Detector", Interaction 2006, pp. 23-24, 2006, Hiroyuki Manabe, Masaaki Fukumoto However, since drift noise significantly changes with time, frequent correction is required in order to increase drift noise reduction accuracy. In other words, the above process of measuring the electro-oculography signal in a state where the user is gazing at the specified position needs to be frequently performed. Thus, the noise reduction method disclosed in Patent Literature 1 is not practical.

Besides, the noise reduction method disclosed in Patent Literature 1 relates to the reduction of drift noise which is low frequency noise, but does not address the problem of high frequency noise.

SUMMARY OF THE INVENTION

In view of the above, the present invention has an object of reducing noise components in an electro-oculography original signal to thereby improve an S/N ratio in electro-oculography measurement, by a simpler method.

A noise reduction device according to one form of the present invention includes: a saccade information obtaining unit that obtains saccade information from an electro-oculography original signal that indicates an electro-oculogram resulting from an eye movement of a user, the saccade information relating to a saccadic movement which is a rapid eyeball movement; a control unit that determines a filter property for reducing noise included in the electro-oculography original signal, on the basis of the saccade information obtained by the saccade information obtaining unit; and a filtering unit that reduces the noise included in the electro-oculography original signal using the filter property determined by the control unit, to output an electro-oculography signal.

According to the above structure, noise included in the electro-oculography original signal can be reduced easily, which contributes to an improved S/N ratio.

As an example, the filtering unit may be a high pass filter. The saccade information obtaining unit may include: a saccade detecting unit that outputs a saccade detection signal in the case where a saccade signal indicating the saccadic movement is included in the electro-oculography original signal; and a time interval calculating unit that calculates, as the saccade information, a time interval of temporally adjacent saccade detection signals output from the saccade detecting unit. The control unit may then increase a cutoff frequency in the case where the time interval is equal to or smaller than a first value, and decrease the cutoff frequency in the case where the time interval is larger than the first value.

As another example, the filtering unit may be a high pass filter. The saccade information obtaining unit may include: a saccade detecting unit that outputs a saccade detection signal in the case where a saccade signal indicating the saccadic movement is included in the electro-oculography original signal; and an occurrence frequency calculating unit that calculates, as the saccade information, an occurrence frequency of the saccade detection signal output from the saccade detecting unit. The control unit may then increase a cutoff frequency in the case where the occurrence frequency is larger than a second value, and decrease the cutoff frequency in the case where the occurrence frequency is equal to or smaller than the second value.

Moreover, when the noise is drift noise which is a change of a base line of the electro-oculography original signal with time, the control unit desirably changes the cutoff frequency within a range from 0 to a maximum frequency of the drift noise.

As another example, the filtering unit may be a low pass filter. The saccade information obtaining unit may include: a saccade detecting unit that outputs a saccade detection signal in the case where a saccade signal indicating the saccadic movement is included in the electro-oculography original signal; and a non-occurrence area specifying unit that specifies a non-occurrence area on the basis of the saccade detection signal output from the saccade detecting unit, the non-occurrence area being a temporally continuous area which includes a sample subject to filtering by the filtering unit and in which no saccadic movement occurs. The control unit may then set a filter coefficient of a sample not included in the non-occurrence area, to 0.

As another example, the filtering unit may be a low pass filter. The saccade information obtaining unit may include: a saccade detecting unit that outputs, in the case where a saccade signal indicating the saccadic movement is included in the electro-oculography original signal, an amplitude of the saccade signal; and a non-occurrence probability calculating unit that calculates a non-occurrence probability for each sample input to the filtering unit, according to the amplitude detected by the saccade detecting unit, the non-occurrence probability being a probability that no saccade occurs in a position of the sample. The control unit may then set a larger filter coefficient for a sample having a higher non-occurrence probability.

Moreover, the saccade detecting unit may include: a delayed signal generating unit that generates a delayed signal by delaying the electro-oculography original signal by a predetermined amount of time; a subtraction unit that generates an output signal obtained by subtracting the delayed signal from the electro-oculography original signal; and a saccade determining unit that determines a signal, in the output signal, that exceeds a predetermined threshold, as the saccade signal indicating the saccadic movement.

Moreover, the predetermined amount of time may be shorter than an amount of time of visual fixation by the user on a calibration index.

Moreover, the saccade detecting unit may include: a first filtering unit that performs one of maximum value filtering and minimum value filtering on the electro-oculography original signal, to output a first electro-oculography signal; a subtraction unit that generates an output signal by subtracting, from one of the first electro-oculography signal and a second electro-oculography signal, an other one of the first electro-oculography signal and the second electro-oculography signal, the second electro-oculography signal being obtained from the electro-oculography original signal; and a saccade determining unit that determines a signal, in the output signal, that exceeds a predetermined threshold, as the saccade signal indicating the saccadic movement.

Moreover, the saccade detecting unit may further include a second filtering unit that performs an other one of the maximum value filtering and the minimum value filtering on the electro-oculography original signal, to output the second electro-oculography signal.

Moreover, the saccade detecting unit may further include a second filtering unit that performs an other one of the maximum value filtering and the minimum value filtering on the first electro-oculography signal, to output the second electro-oculography signal.

Moreover, the noise reduction device may further include a synthesized signal generating unit that generates a synthesized signal by averaging the electro-oculography original signal measured through each of a plurality of channels, for each group to which the plurality of channels belong, and differential-amplifying an average value of each group. The saccade detecting unit may then detect a saccade included in the synthesized signal.

An electro-oculography measuring device according to one form of the present invention includes: an electro-oculography measuring unit that outputs an electro-oculography original signal that indicates an electro-oculogram resulting from an eye movement; and the above noise reduction device that reduces noise included in the electro-oculography original signal.

An ophthalmological diagnosis device according to one form of the present invention diagnoses a retinal state of a user. In detail, the ophthalmological diagnosis device includes: the above electro-oculography measuring device; and a diagnosis unit that detects retinal abnormality of the user from an electro-oculography signal output from the electro-oculography measuring device.

An eye-gaze tracking device according to one form of the present invention detects a gaze-path direction of a user from an electro-oculography signal. In detail, the eye-gaze tracking device includes: the above electro-oculography measuring device; a calibration index presenting unit that presents a calibration index to the user; a saccade detecting unit that detects a saccadic movement from the electro-oculography signal and outputs an electro-oculography change amount, the saccadic movement being a rapid eyeball movement that occurs when a gaze point of the user moves to the calibration index presented by the calibration index presenting unit, and the electro-oculography change amount being an amount of change in electro-oculogram before or after the saccadic movement; a calibration parameter calculating unit that calculates a calibration parameter, on the basis of a position of the calibration index presented by the calibration index presenting unit and the electro-oculography change amount output from the saccade detecting unit; and a calibration unit that detects the gaze-path direction of the user from the electro-oculography signal, on the basis of the calibration parameter.

A wearable camera according to one form of the present invention captures an image in a gaze-path direction of a user. In detail, the wearable camera includes: an imaging unit; the above eye-gaze tracking device; and an imaging control unit that causes the imaging unit to capture an image in a gaze-path direction detected by the eye-gaze tracking device.

A head-mounted display according to one form of the present invention moves a mouse pointer in a gaze-path direction of a user. In detail, the head-mounted display includes: a display unit that displays an image and the mouse pointer; the above eye-gaze tracking device; and a display control unit that moves the mouse pointer displayed by the display unit, in a gaze-path direction detected by the eye-gaze tracking device.

Electronic eyeglasses according to one form of the present invention change a focus of each of lenses according to a gaze point of a user. In detail, the electronic eyeglasses include: lenses each having a changeable focus; the above eye-gaze tracking device; and a focus control unit that changes the focus of each of the lenses according to a gaze point detected by the eye-gaze tracking device.

A noise reduction method according to one form of the present invention includes: obtaining saccade information from an electro-oculography original signal that indicates an electro-oculogram resulting from an eye movement of a user, the saccade information relating to a saccadic movement which is a rapid eyeball movement; determining a filter property for reducing noise included in the electro-oculography original signal, on the basis of the saccade information obtained in the obtaining; and reducing the noise included in the electro-oculography original signal using the filter property determined in the determining, to output an electro-oculography signal.

A non-transitory computer-readable recording medium for use in a computer according to one form of the present invention has a computer program recorded thereon for causing the computer to execute: obtaining saccade information from an electro-oculography original signal that indicates an electro-oculogram resulting from an eye movement of a user, the saccade information relating to a saccadic movement which is a rapid eyeball movement; determining a filter property for reducing noise included in the electro-oculography original signal, on the basis of the saccade information obtained in the obtaining; and reducing the noise included in the electro-oculography original signal using the filter property determined in the determining, to output an electro-oculography signal.

According to the present invention, the S/N ratio of the electro-oculography signal in electro-oculography measurement can be improved by a simpler method.

FURTHER INFORMATION ABOUT TECHNICAL BACKGROUND TO THIS APPLICATION

The disclosure of Japanese Patent Application No. 2009-263713 filed on Nov. 19, 2009 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 35 is a flowchart showing an operation of a synthesized signal generating unit according to Embodiment 10;

FIG. 51A is a diagram showing a table that holds a plurality of combinations of an electro-oculography change amount and an eyeball movement angle associated with each other;

FIG. 51B is a diagram showing a table that holds a plurality of combinations of an electro-oculography change amount and a gaze point associated with each other;

FIG. 52 is a diagram showing a state of a display on which a calibration index is displayed;

FIG. 65 is a diagram explaining a drift in electro-oculography measurement.

DESCRIPTION OF THE PREFERRED EMBODIMENT(S)

The following describes embodiments of the present invention with reference to drawings.

(Embodiment 1)

Figure 1:
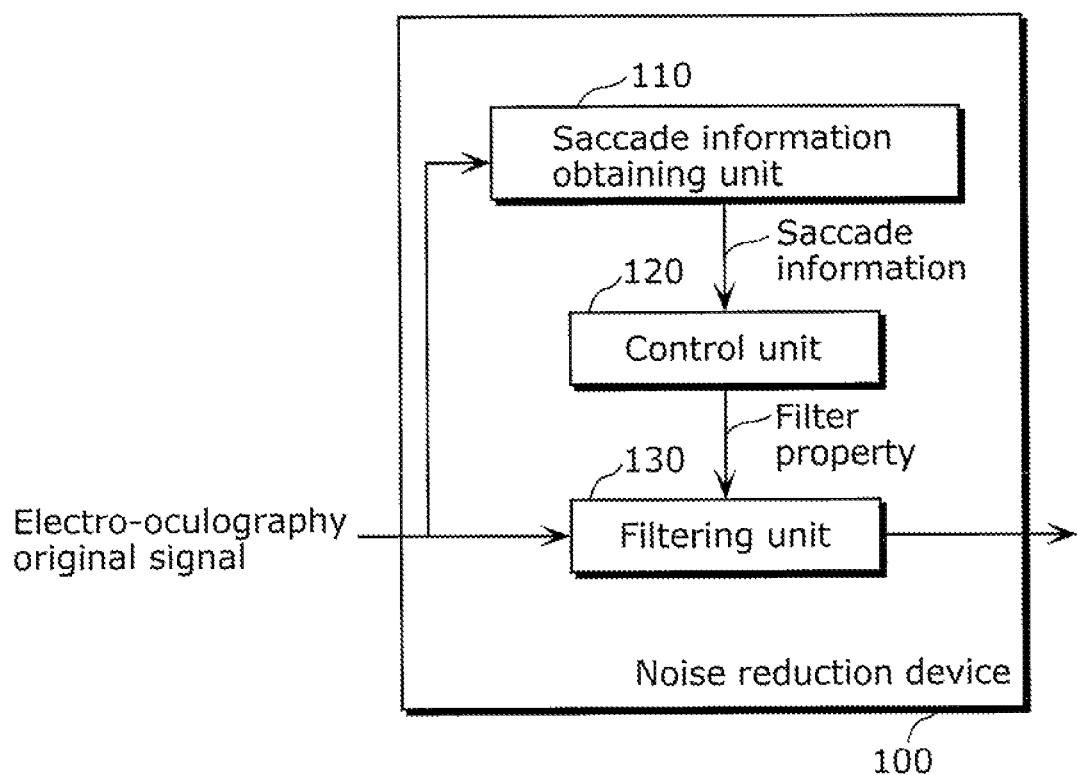
FIG. 1 is a block diagram of a noise reduction device according to Embodiment 1.

FIG. 1 is a block diagram showing a structure of a noise reduction device 100 according to Embodiment 1 of the present invention. The noise reduction device 100 shown in FIG. 1 includes a saccade information obtaining unit 110, a control unit 120, and a filtering unit 130.

The saccade information obtaining unit 110 detects a saccade signal from an electro-oculography original signal, and outputs saccade information. For example, the saccade information includes presence or absence of the saccade signal, an amplitude of the saccade signal, a time interval between adjacent saccade signals, an occurrence frequency of the saccade signal within a predetermined time, and the like.

The control unit 120 determines a filter property of the filtering unit 130 used in noise reduction, on the basis of the saccade information output from the saccade information obtaining unit 110. For example, the filter property controlled by the control unit 120 is a cutoff property, a filter coefficient, or the like.

The filtering unit 130 reduces noise included in the electro-oculography original signal, using the filter property adaptively controlled by the control unit 120. For example, the filtering unit 130 is a low pass filter or a high pass filter.

For instance, the control unit 120 may have a structure of changing a cutoff frequency of the filtering unit 130 according to the adjacent saccade signal time interval included in the saccade information. As an example, in the case where the low pass filter is used as the filtering unit 130, the cutoff frequency is increased when the saccade signal time interval is shorter. A shorter saccade signal time interval corresponds to a state where eye movements are active and have a high frequency. In such a state, frequency characteristics of eye movements are little affected even when the cutoff frequency is increased to reduce noise of a wider range in a low frequency band.

By changing the cutoff frequency of the filtering unit 130 according to the time interval in this way, drift noise which is an example of low frequency noise can be reduced without significantly affecting frequency characteristics of eye movements. Thus, noise components in the electro-oculography original signal can be reduced by a simpler method. Processing in the control unit 120 will be described in more detail later.

Figure 2:
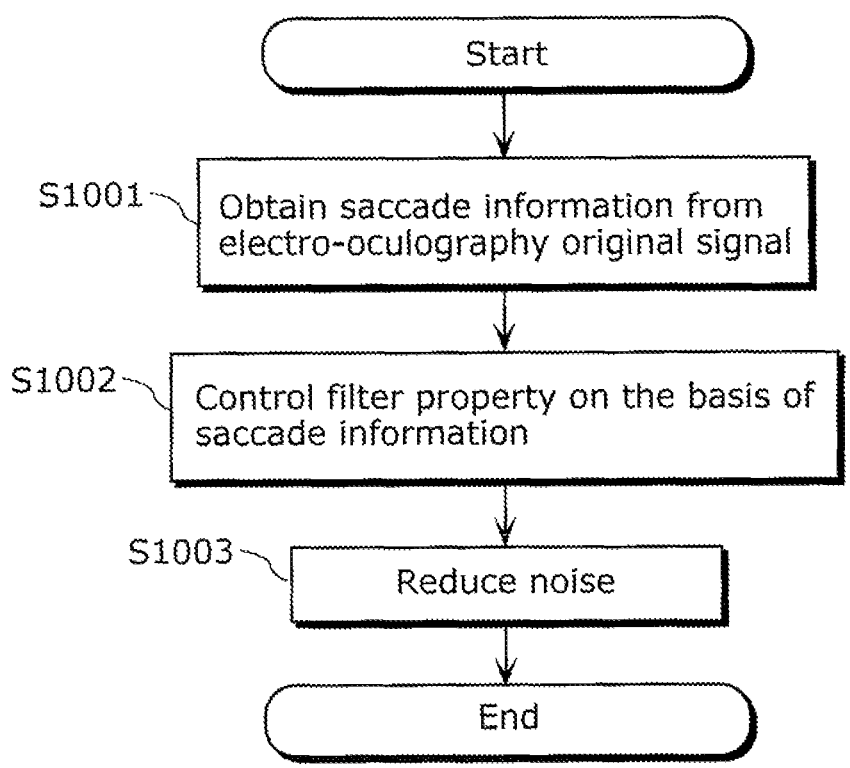
FIG. 2 is a flowchart showing an operation of the noise reduction device according to Embodiment 1.

The following describes a procedure of measuring an electro-oculography signal by the noise reduction device 100 according to Embodiment 1, with reference to FIG. 2. First, the saccade information obtaining unit 110 obtains the saccade information such as the saccade signal presence or absence, the saccade signal amplitude, the adjacent saccade signal time interval, or the saccade signal occurrence frequency within the predetermined time, from the electro-oculography original signal (Step S1001). Following this, the control unit 120 adaptively controls the filter property of the filtering unit 130, on the basis of the saccade information obtained by the saccade information obtaining unit 110 (Step S1002). Lastly, the filtering unit 130 reduces noise included in the electro-oculography original signal, using the adaptively controlled filter property (Step S1003).

According to Embodiment 1 described above, the saccade information is obtained from the electro-oculography original signal, and the filter property is adaptively controlled on the basis of the obtained saccade information. This enables noise components in the electro-oculography original signal to be reduced by a simpler method.

(Embodiment 2)

Embodiment 2 of the present invention relates to a device and method for reducing drift noise in particular, in order to achieve an improved S/N ratio in electro-oculography measurement. Drift noise is a phenomenon in which a base line of an electro-oculography original signal changes with time. Drift noise is caused, for example, by a material of an electrode used for electro-oculography measurement, a change in contact state between the skin and the electrode, and so on. Drift noise is low frequency noise and has frequency characteristics that partly overlap with frequency characteristics of eye movements, and so is a major factor responsible for a decrease in S/N ratio in electro-oculography measurement.

Figure 64:
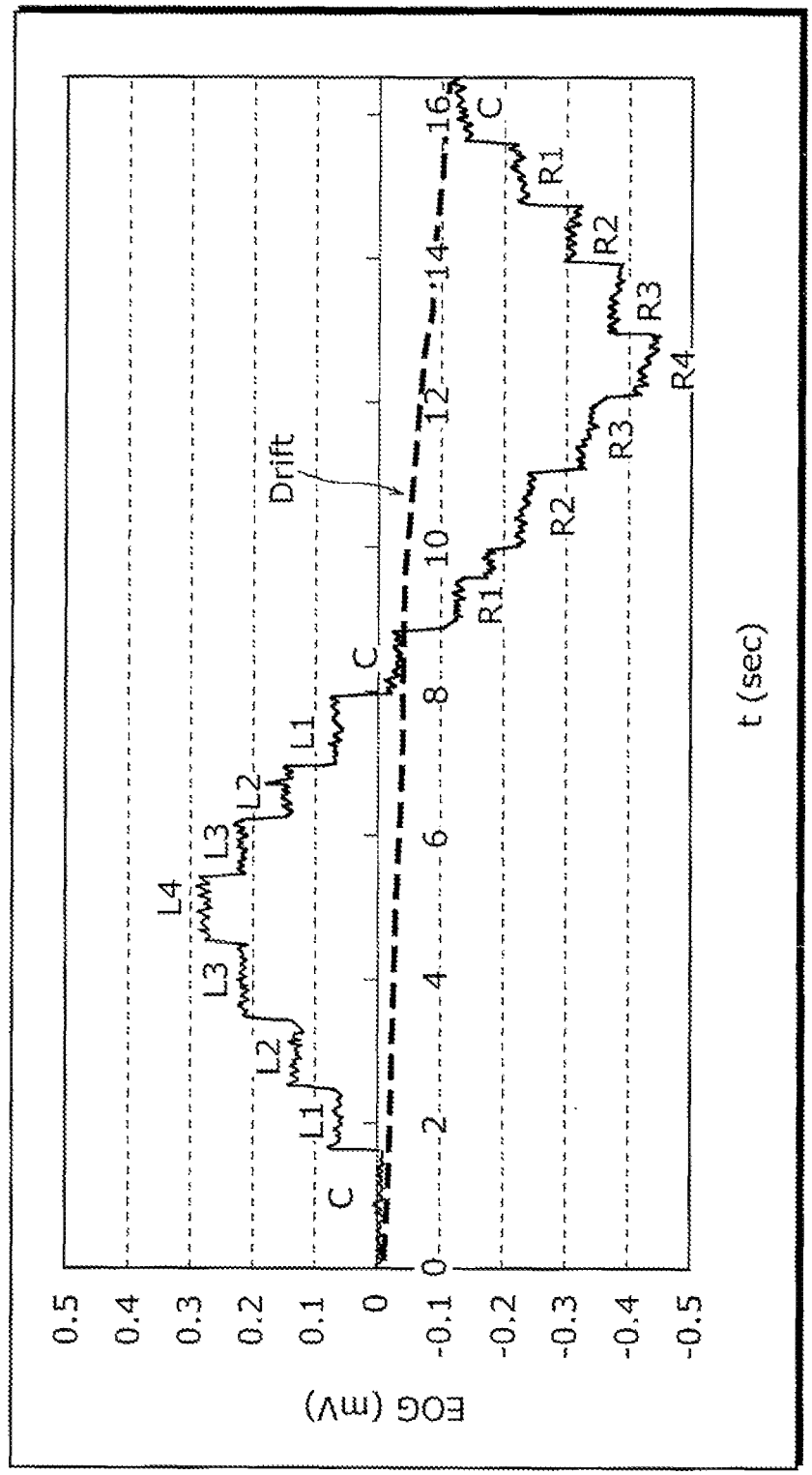
FIG. 64 is a diagram showing an example of a drift in electro-oculography measurement.

FIG. 64 shows a result of measuring an electro-oculogram by actually placing electrodes on the user. FIG. 64 shows the electro-oculography measurement result when a plurality of indexes are sequentially displayed at one second intervals in the order shown in FIG. 65. As shown in FIG. 64, a base line of the electro-oculogram changes with time. In view of this, Embodiment 2 describes a device and method for separating drift noise from the electro-oculography original signal by using a time interval of a saccade detection signal.

Figure 3:
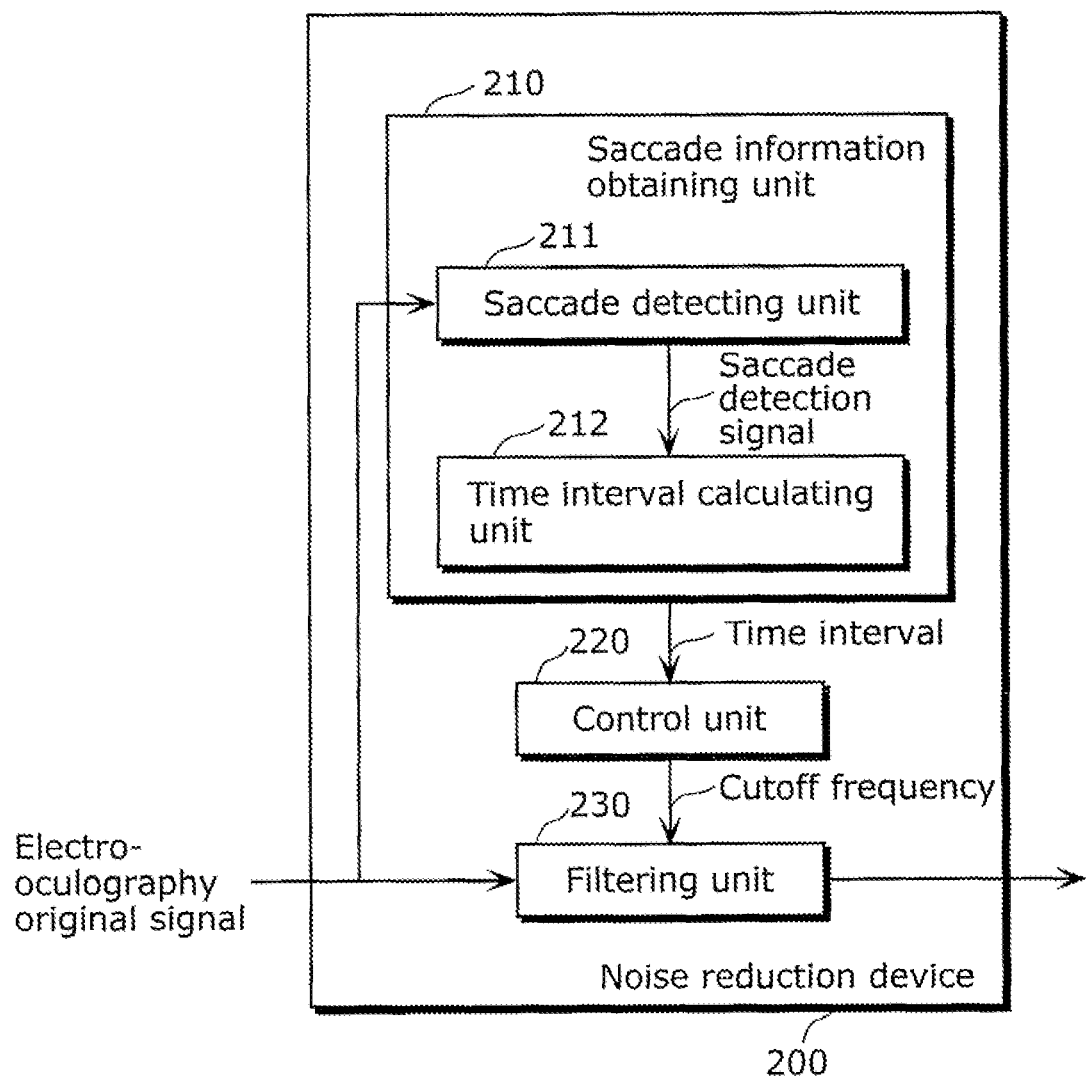
FIG. 3 is a block diagram of a noise reduction device according to Embodiment 2.

FIG. 3 is a block diagram showing a structure of a noise reduction device 200 according to Embodiment 2 of the present invention. The noise reduction device 200 shown in FIG. 3 includes a saccade information obtaining unit 210, a control unit 220, and a filtering unit 230. The saccade information obtaining unit 210 includes a saccade detecting unit 211 and a time interval calculating unit 212. This noise reduction device 200 is a device that reduces low frequency noise such as drift noise included in the electro-oculography original signal, and uses a high pass filter in the filtering unit 230.

The saccade detecting unit 211 outputs a saccade detection signal, in the case where a saccade signal indicating a saccadic movement is included in the electro-oculography original signal. A saccade (saccadic eye movement) is an eye movement that occurs when capturing an object projected on a peripheral retina of a low resolution, at a central fovea of retina of a high resolution. A saccade is known to have an extremely high speed of 100 to 500 (°/sec).

Figure 19:
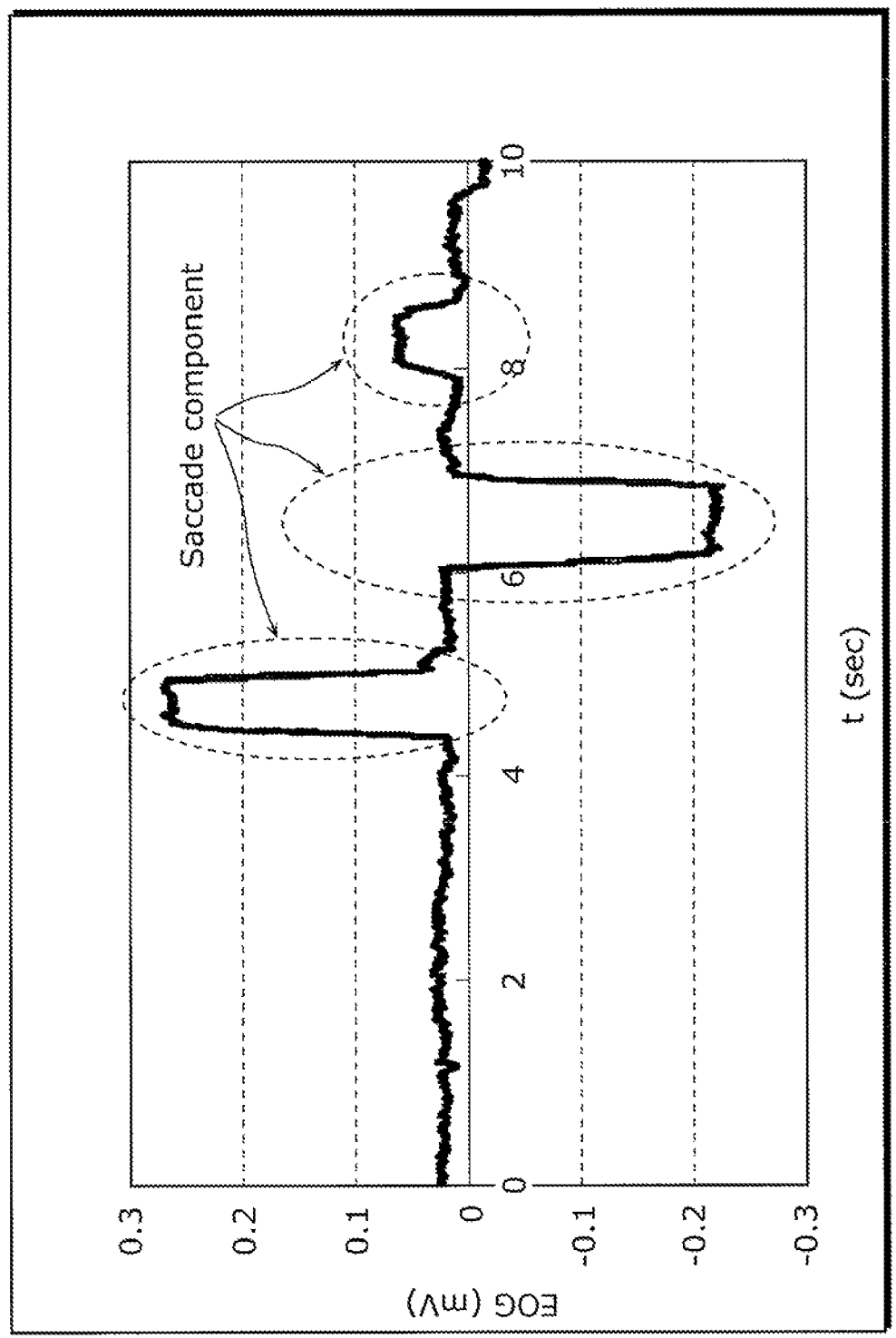
FIG. 19 is a diagram showing an example of an electro-oculography signal that includes a saccade signal.

FIG. 19 shows an example of a waveform of an electro-oculography original signal including a saccade signal. In FIG. 19, the parts enclosed by dotted lines indicate saccades. When a saccade occurs, a potential changes rapidly and stays at the level for a fixed time (visual fixation), and then returns to the original level. This is an example of the case where an eyeball is moved from an index A to an index B by a saccade and then moved again from the index B to the index A by a saccade. A human typically alternates a visual fixation of about 0.3 seconds and a saccade of several dozen milliseconds, to obtain information on his/her surroundings.

As a method for detecting a saccade signal from the electro-oculography original signal as shown in FIG. 19, there is a method of applying each of maximum value filtering and minimum value filtering to the electro-oculography original signal and calculating a difference between results of the two filtering operations. This processing will be described in detail later.

Figure 26:
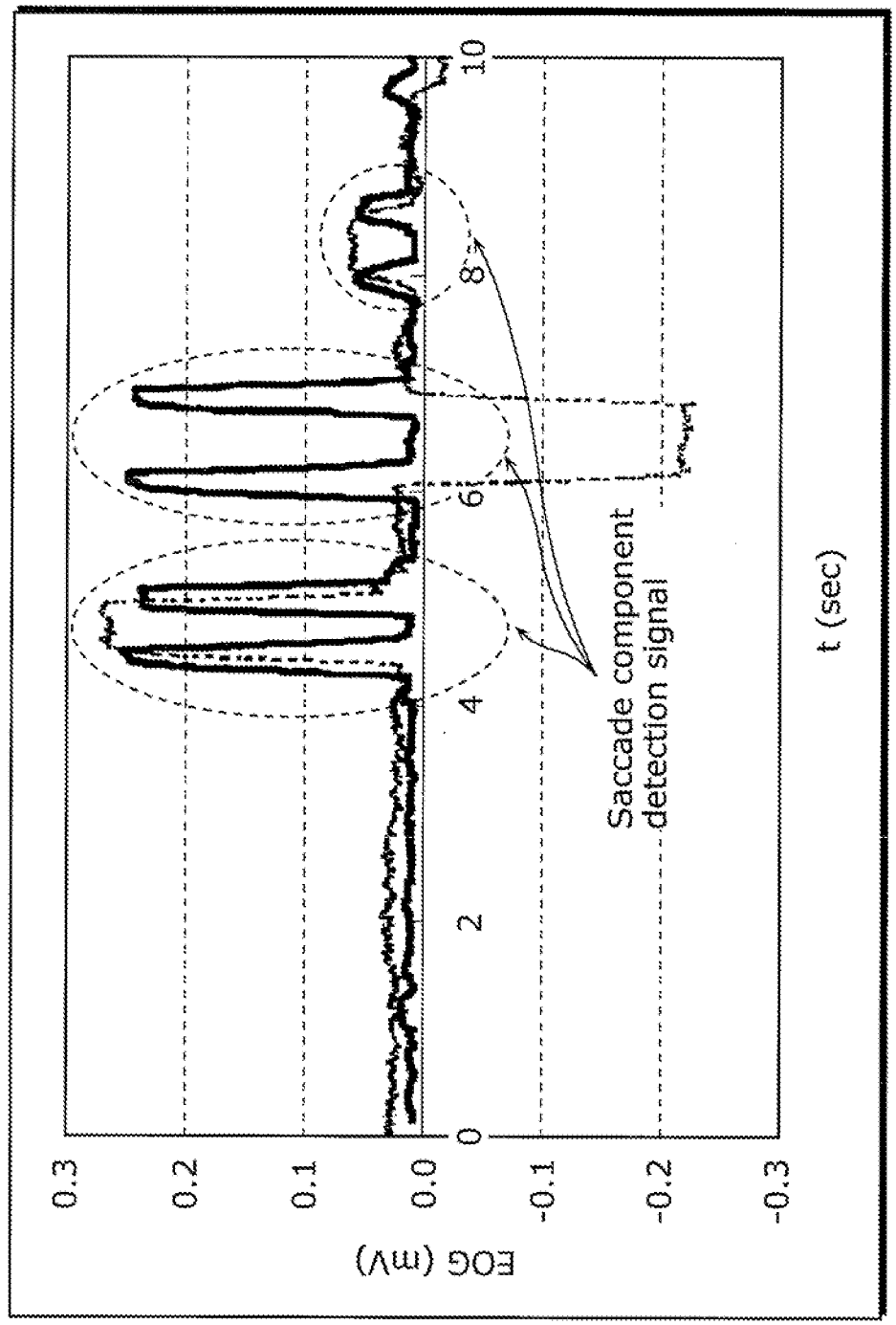
FIG. 26 is a diagram explaining a saccade detection signal extracted from the electro-oculography signal shown in FIG. 19.

FIG. 26 shows an output signal obtained by applying maximum value filtering and minimum value filtering to the electro-oculography original signal shown in FIG. 19. As shown in FIG. 26, a peak appears in the output signal only when a saccade occurs.

The saccade detecting unit 211 includes a saccade determining unit (not shown) that determines a signal, in the output signal, exceeding a predetermined threshold, as a saccade signal indicating a saccadic movement. The saccade detecting unit 211 outputs a saccade detection signal indicating the detection of the saccade signal, to the time interval calculating unit 212.

Though a minimum value filter and a maximum value filter are used as a method for detecting a saccade signal in Embodiment 2, any technique such as a high pass filter may be used so long as a saccade is detected.

Figure 4:
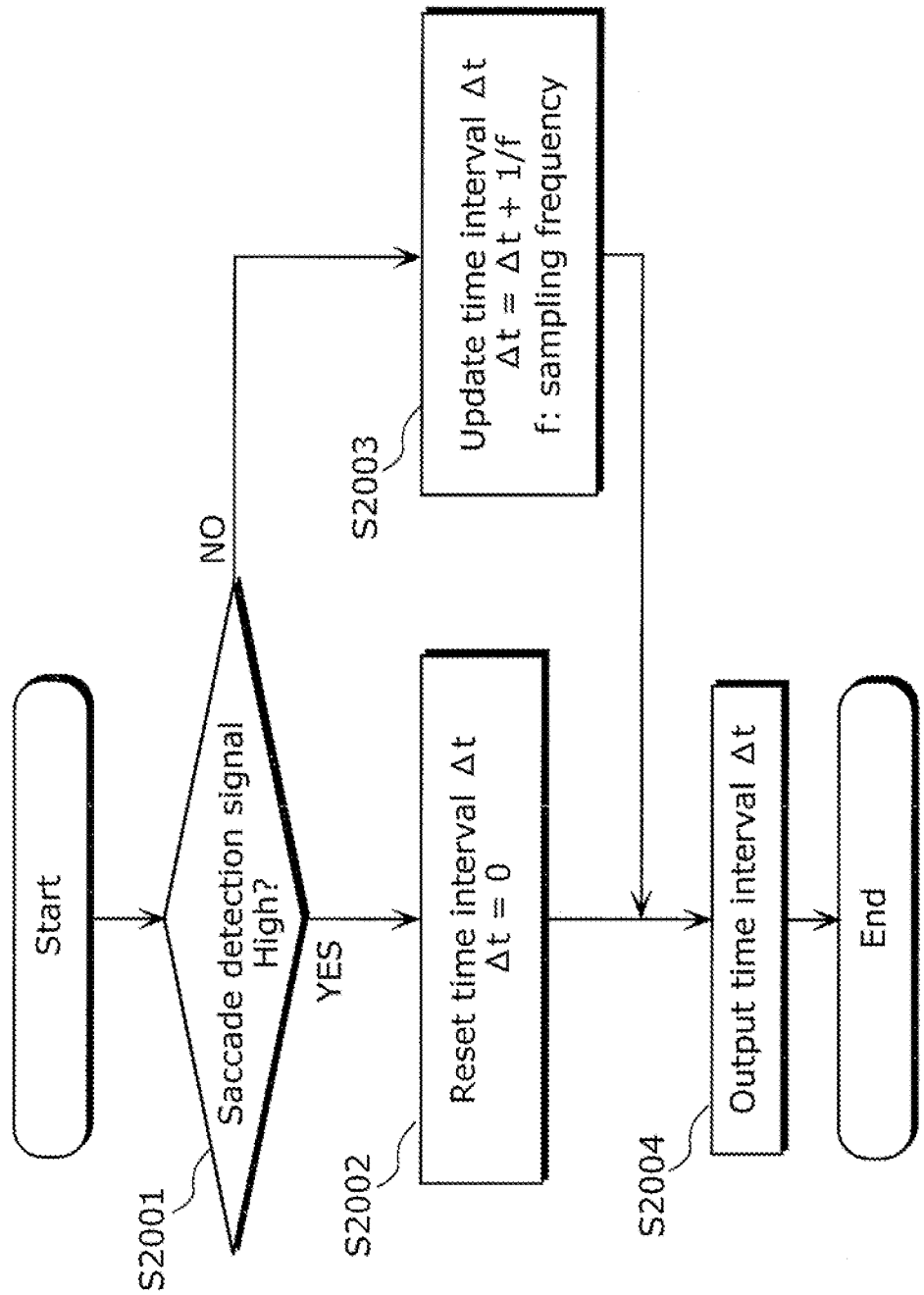
FIG. 4 is a flowchart showing an operation of a time interval calculating unit according to Embodiment 2.

The time interval calculating unit 212 calculates a saccade time interval, using the saccade detection signal output from the saccade detecting unit 211. For instance, the time interval calculating unit 212 may have a structure of including a timer that corresponds to a sampling frequency, and resetting the timer according to the saccade detection signal. FIG. 4 shows a detailed procedure.

First, the time interval calculating unit 212 determines whether or not the saccade detection signal is High, that is, whether or not a saccade is detected (Step S2001). When the saccade detection signal is High, the time interval calculating unit 212 resets a time interval $\Delta t$ of the saccade detection signal (Step S2002). When the saccade detection signal is not High, on the other hand, the time interval calculating unit 212 adds a time $1/f$ corresponding to a sampling frequency $f$ of the noise reduction device 200 to the time interval $\Delta t$, thereby updating the time interval $\Delta t$ (Step S2003). The time interval calculating unit 212 then outputs the reset or updated time interval $\Delta t$ (Step S2004).

The control unit 220 determines a cutoff frequency to be applied to the electro-oculography original signal in the filtering unit 230 which is a high pass filter, using the time interval $\Delta t$ output from the time interval calculating unit 212. For example, in the case where the time interval $\Delta t$ of the saccade detection signal is short, the eye movement appears as a high frequency signal in the electro-oculography original signal, so that the cutoff frequency is increased at this timing to reduce drift noise of a low frequency. On the other hand, in the case where the time interval Δt of the saccade detection signal is long, the eye movement is likely to be a low frequency movement such as gazing or pursuit, so that the cutoff frequency is decreased to protect the electro-oculography original signal.

Figure 5:
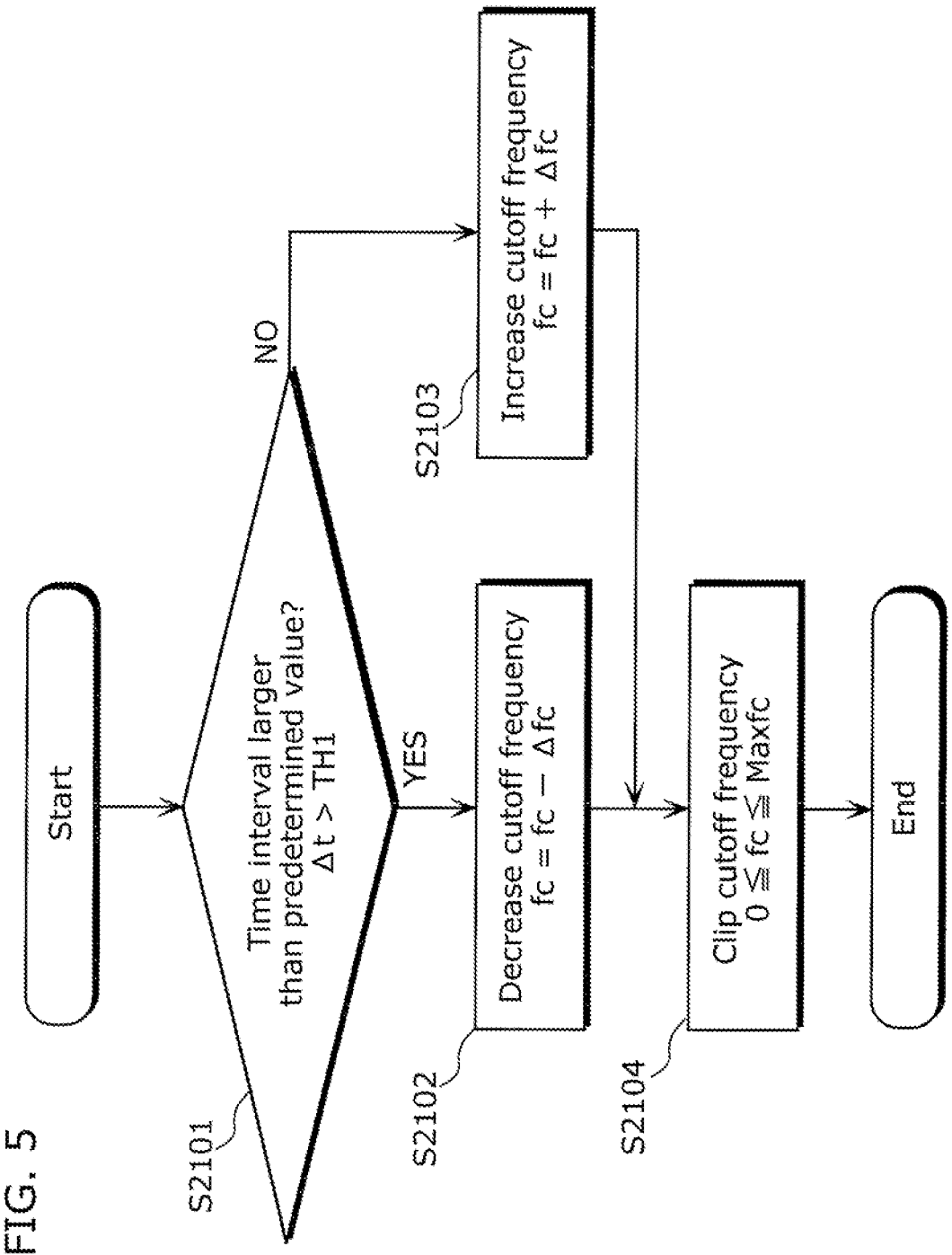
FIG. 5 is a flowchart showing an operation of a control unit according to Embodiment 2.

A detailed procedure is described below, with reference to FIG. 5. Note that the procedure shown in FIG. 5 is executed using the time interval Δt prior to reset at a timing when a saccade is detected in the procedure shown in FIG. 4, as an example.

First, the control unit 220 determines whether or not the time interval Δt is larger than a predetermined value TH1 (Step S2101). When the time interval Δt is larger than the predetermined value TH1, the control unit 220 subtracts a predetermined value Δfc from a cutoff frequency fc, thereby decreasing the cutoff frequency (Step S2102). When the time interval Δt is equal to or smaller than the predetermined value TH1, on the other hand, the control unit 220 to adds the predetermined value Δfc to the cutoff frequency fc, thereby increasing the cutoff frequency (Step S2103). That is, the control unit 220 increases the cutoff frequency fc in the case where the time interval Δt is equal to or smaller than the predetermined value TH1, and decreases the cutoff frequency fc in the case where the time interval Δt is larger than the predetermined value TH1.

The control unit 220 then clips the updated cutoff frequency fc to a predetermined range (from 0 to Maxfc), and outputs the clipped cutoff frequency fc (Step S2104). Here, Maxfc is an estimated maximum frequency of drift noise. In other words, the control unit 220 changes the cutoff frequency within a range from 0 to the maximum frequency of drift noise.

The filtering unit 230 applies the high pass filter to the electro-oculography original signal using the cutoff frequency fc output from the control unit 220, to output an electro-oculography signal in which drift noise has been reduced.

Figure 6:
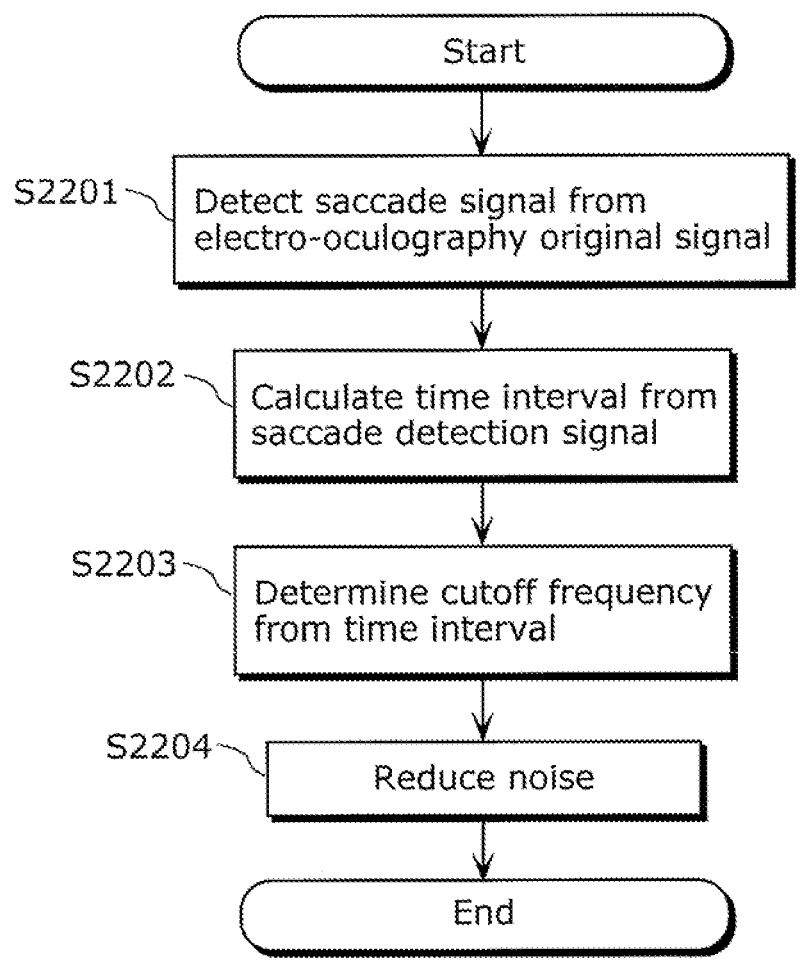
FIG. 6 is a flowchart showing an operation of the noise reduction device according to Embodiment 2.

An overall procedure by which the noise reduction device 200 according to Embodiment 2 described above outputs the electro-oculography signal is described below, with reference to FIG. 6.

First, the noise reduction device 200 obtains the saccade signal from the electro-oculography original signal (Step S2201). Next, the noise reduction device 200 obtains the time interval Δt from the saccade detection signal (Step S2202). The noise reduction device 200 then determines the cutoff frequency fc of the high pass filter, from the obtained time interval Δt (Step S2203). The noise reduction device 200 performs filtering using the new cutoff frequency fc, thereby reducing drift noise (Step S2204).

According to Embodiment 2 described above, the time interval Δt of the saccade detection signal is obtained from the electro-oculography original signal, and the cutoff frequency fc of the high pass filter is adaptively controlled on the basis of the time interval Δt. This enables drift noise in the electro-oculography original signal to be reduced by a simpler method.

Though the cutoff frequency fc is increased or decreased depending on whether or not the time interval Δt is larger than the predetermined value TH1 in Embodiment 2, the cutoff frequency fc may be directly calculated from the time interval Δt. Alternatively, a table showing correspondence between the time interval Δt and the cutoff frequency fc may be created beforehand so that the cutoff frequency fc corresponding to the time interval Δt calculated by the time interval calculating unit 212 is extracted from the table and notified to the filtering unit 230.

(Embodiment 3)

Embodiment 3 of the present invention relates to a device and method for reducing drift noise in particular, in order to achieve an improved S/N ratio in electro-oculography measurement. Embodiment 3 differs from Embodiment 2 in that drift noise is separated from the electro-oculography original signal by using not the time interval of the saccade detection signal but frequency information of the saccade detection signal.

Figure 7:
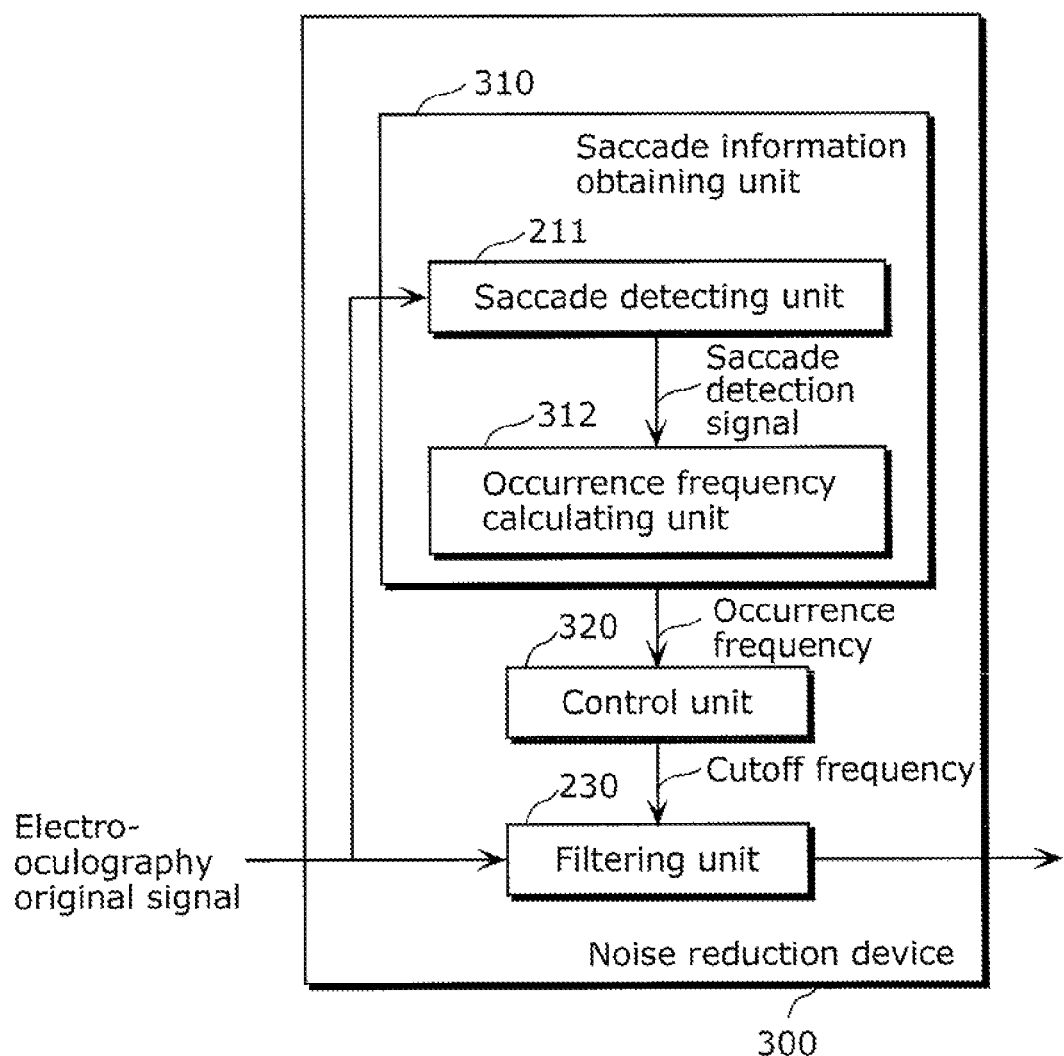
FIG. 7 is a block diagram of a noise reduction device according to Embodiment 3.

FIG. 7 is a block diagram showing a structure of a noise reduction device 300 according to Embodiment 3 of the present invention. The noise reduction device 300 according to Embodiment 3 includes a saccade information obtaining unit 310, a control unit 320, and the filtering unit 230. The saccade information obtaining unit 310 includes the saccade detecting unit 211 and an occurrence frequency calculating unit 312. This noise reduction device 300 is a device that reduces low frequency noise such as drift noise included in the electro-oculography original signal, and uses a high pass filter in the filtering unit 230.

In FIG. 7, the same components as those described in the above embodiments are given the same reference numerals, and their description is omitted.

The occurrence frequency calculating unit 312 includes an internal memory (not shown) storing a saccade detection signal of a predetermined time, and calculates a saccade occurrence frequency using the saccade detection signal of the predetermined time stored in the internal memory. For instance, the occurrence frequency calculating unit 312 may count the saccade detection signal within the predetermined time, and set a counted sum as the saccade occurrence frequency.

Figure 8:
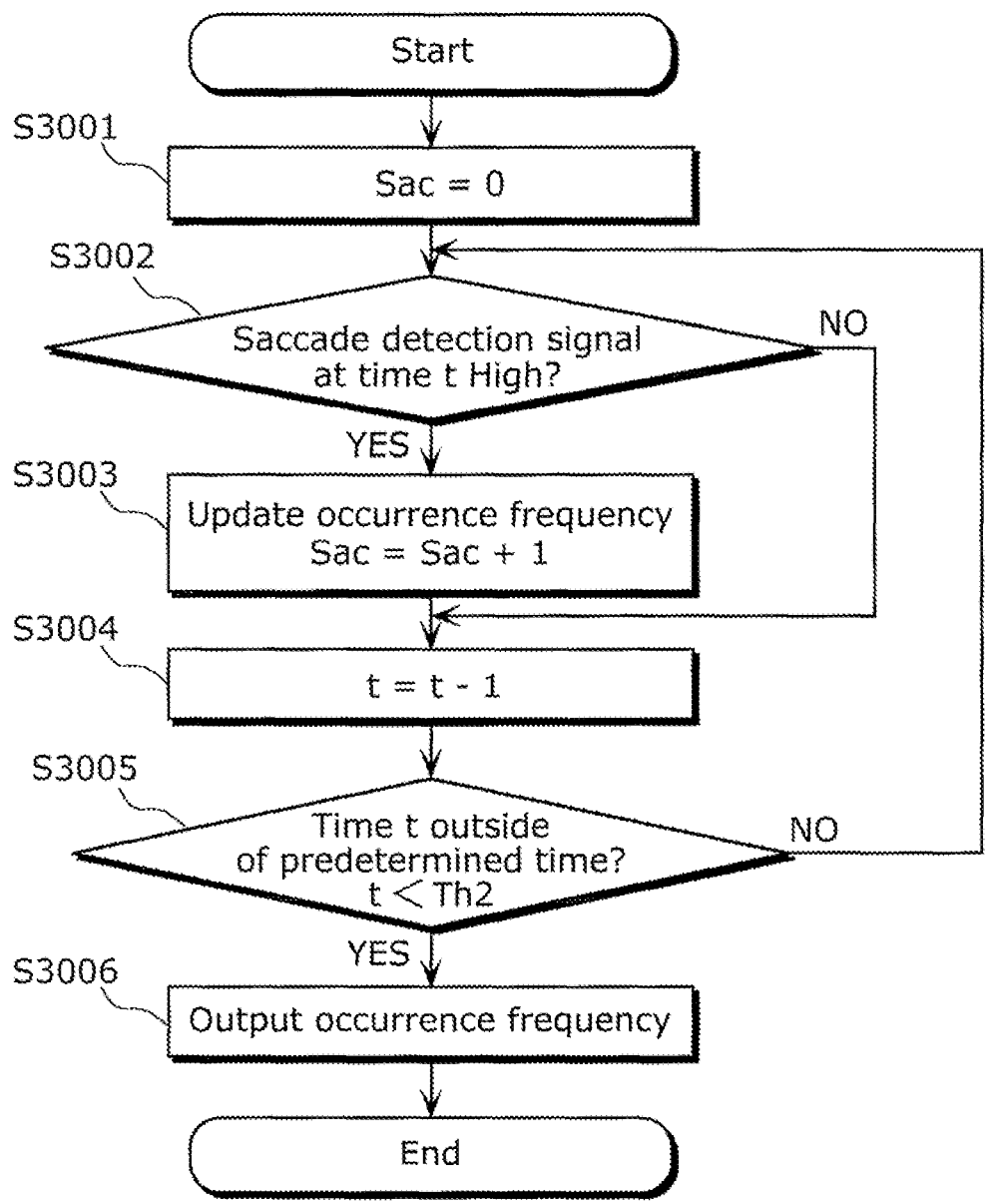
FIG. 8 is a flowchart showing an operation of an occurrence frequency calculating unit according to Embodiment 3.

A detailed procedure is described below, with reference to FIG. 8. First, the occurrence frequency calculating unit 312 resets a saccade occurrence frequency Sac to 0 (Step S3001). Next, the occurrence frequency calculating unit 312 determines whether or not the saccade detection signal at time t in the internal memory is High (Step S3002). When the saccade detection signal at time t is High, the occurrence frequency calculating unit 312 adds 1 to the occurrence frequency Sac (Step S3003). When the saccade detection signal at time t is not High, the occurrence frequency calculating unit 312 does not add 1 to the occurrence frequency Sac. The occurrence frequency calculating unit 312 then updates time t, by setting time (t−1) of an immediately preceding sample as time t (Step S3004). The occurrence frequency calculating unit 312 determines whether or not updated time t is within the predetermined time stored in the internal memory, that is, whether or not t<Th2 (Step S3005). When updated time t is within the predetermined time, the occurrence frequency calculating unit 312 returns to Step S3002 to determine whether or not the saccade detection signal at updated time t is High. When updated time t is outside of the predetermined time, the occurrence frequency calculating unit 312 outputs the calculated occurrence frequency Sac (Step S3006).

The control unit 320 determines the cutoff frequency fc to be applied to the electro-oculography original signal in the filtering unit 230 which is a high pass filter, using the occurrence frequency Sac output from the occurrence frequency calculating unit 312. For example, in the case where the saccade occurrence frequency is large, the eye movement appears as a high frequency signal in the electro-oculography original signal, so that the cutoff frequency fc is increased to reduce drift noise of a low frequency. On the other hand, in the case where the saccade occurrence frequency is small, the eye movement is likely to be a low frequency movement such as gazing or pursuit, so that the cutoff frequency fc is decreased to protect the electro-oculography original signal.

Figure 9:
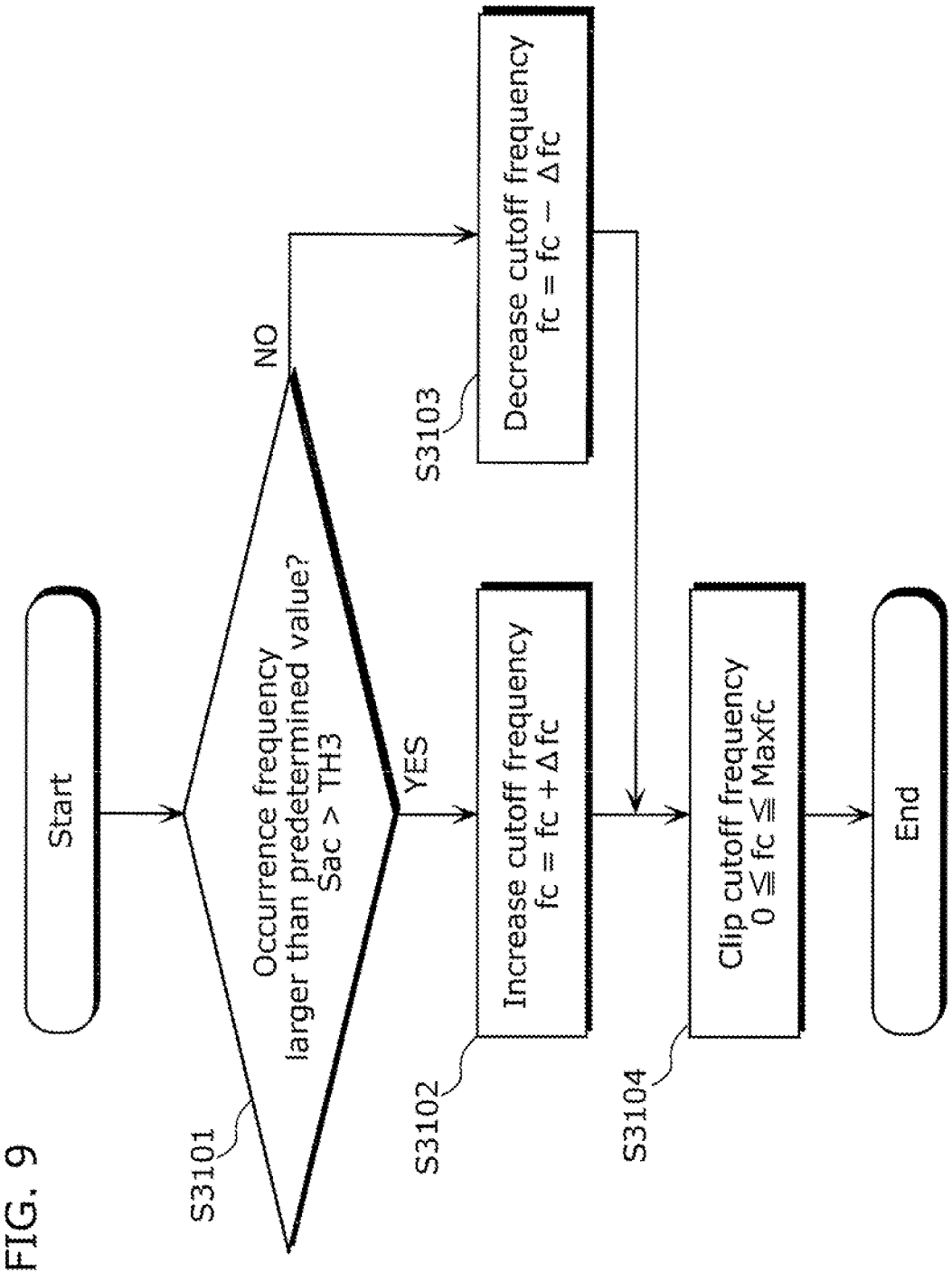
FIG. 9 is a flowchart showing an operation of a control unit according to Embodiment 3.

A detailed procedure is described below, with reference to FIG. 9. First, the control unit 320 determines whether or not the occurrence frequency Sac is larger than a predetermined value TH3 (Step S3101). When the occurrence frequency Sac is larger than the predetermined value TH3, the control unit 320 adds the predetermined value Δfc to the cutoff frequency fc, thereby increasing the cutoff frequency (Step S3102). When the occurrence frequency Sac is equal to or smaller than TH3, on the other hand, the control unit 320 subtracts the predetermined value Mc from the cutoff frequency fc, thereby decreasing the cutoff frequency (Step S3103). That is, the control unit 320 increases the cutoff frequency fc in the case where the occurrence frequency Sac is larger than the predetermined value TH3, and decreases the cutoff frequency fc in the case where the occurrence frequency Sac is equal to or smaller than the predetermined value TH3.

The control unit 320 then clips the updated cutoff frequency fc to a predetermined range (from 0 to Maxfc), and outputs the clipped cutoff frequency fc (Step S3104). Here, Maxfc is an estimated maximum frequency of drift noise. In other words, the control unit 320 changes the cutoff frequency within a range from 0 to the maximum frequency of drift noise.

Figure 10:
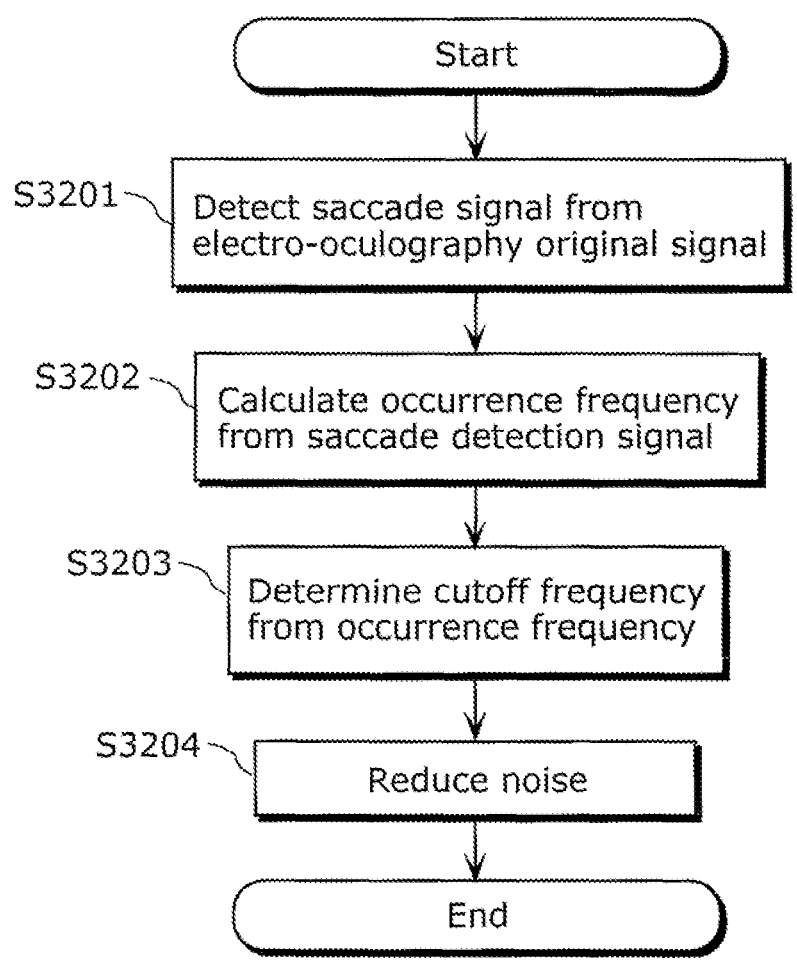
FIG. 10 is a flowchart showing an operation of the noise reduction device according to Embodiment 3.

An overall procedure by which the noise reduction device 300 according to Embodiment 3 described above outputs the electro-oculography signal is described below, with reference to FIG. 10.

First, the noise reduction device 300 obtains the saccade signal from the electro-oculography original signal (Step S3201). Next, the noise reduction device 300 obtains the occurrence frequency Sac from the saccade detection signal (Step S3202). The noise reduction device 300 then determines the cutoff frequency fc of the high pass filter, from the obtained occurrence frequency Sac (Step S3203). The noise reduction device 300 performs filtering using the new cutoff frequency fc, thereby reducing drift noise (Step S3204).

According to Embodiment 3 described above, the saccade occurrence frequency Sac is obtained from the electro-oculography original signal, and the cutoff frequency fc of the high pass filter is adaptively controlled on the basis of the occurrence frequency Sac. This enables drift noise in the electro-oculography original signal to be reduced by a simpler method.

Though the cutoff frequency fc is increased or decreased depending on whether or not the occurrence frequency Sac is larger than the predetermined value TH3 in Embodiment 3, the cutoff frequency fc may be directly calculated from the occurrence frequency Sac. Alternatively, a table showing correspondence between the occurrence frequency Sac and the cutoff frequency fc may be created beforehand so that the cutoff frequency fc corresponding to the occurrence frequency Sac calculated by the occurrence frequency calculating unit 312 is extracted from the table and notified to the filtering unit 230.

(Embodiment 4)

Embodiment 4 of the present invention relates to a device and method for reducing high frequency noise in particular, in order to achieve an improved S/N ratio in electro-oculography measurement. High frequency noise is, for example, a muscle potential or a brain wave of a living body, power supply noise of an external environment, or the like, and is a factor responsible for a decrease in S/N ratio in electro-oculography measurement. In view of this, Embodiment 4 describes a device and method for separating high frequency noise from the electro-oculography original signal by using the saccade detection signal.

Figure 11:
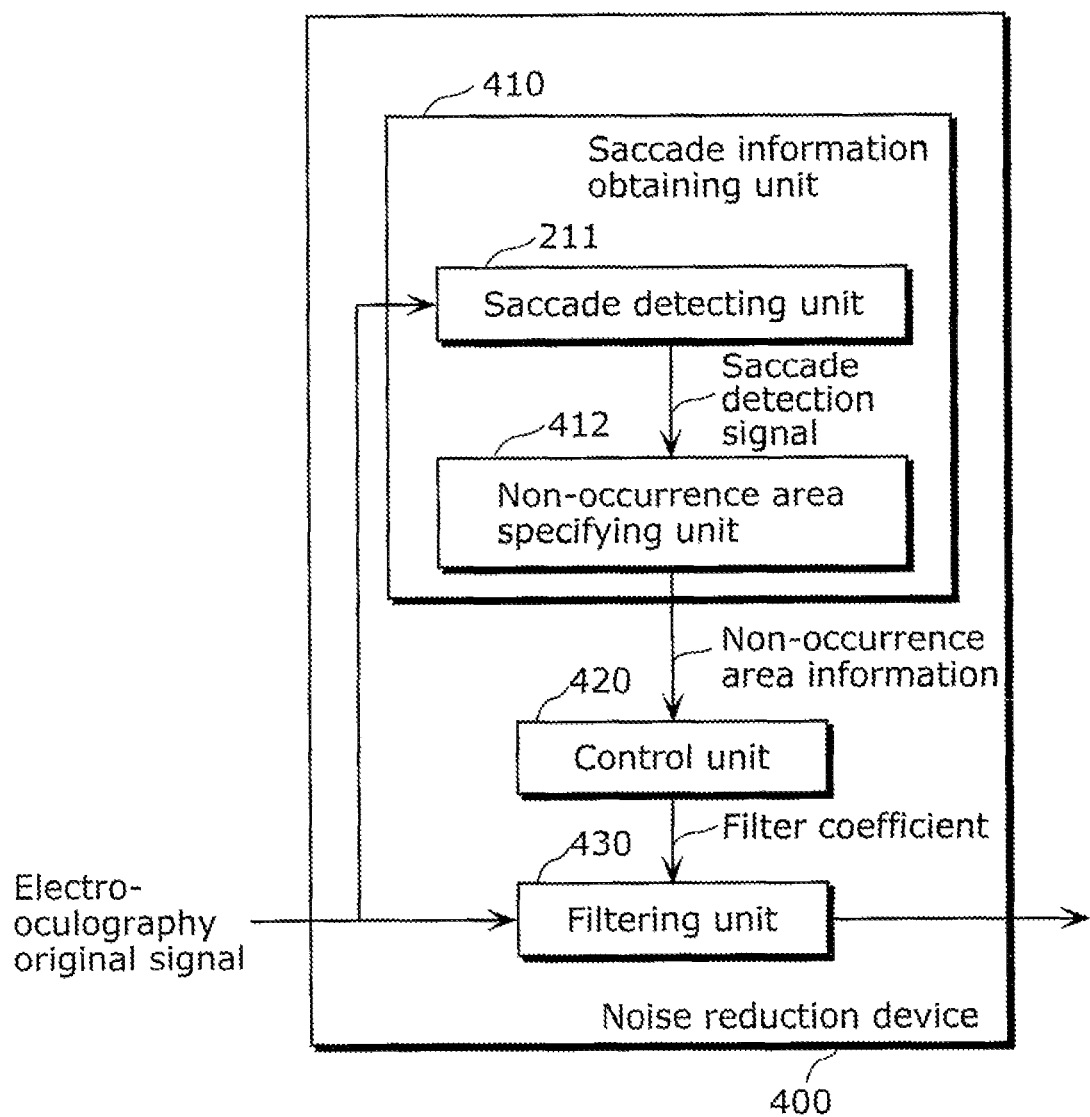
FIG. 11 is a block diagram of a noise reduction device according to Embodiment 4.

FIG. 11 is a block diagram showing a structure of a noise reduction device 400 according to Embodiment 4 of the present invention. The noise reduction device 400 according to Embodiment 4 includes a saccade information obtaining unit 410, a control unit 420, and a filtering unit 430. The saccade information obtaining unit 410 includes the saccade detecting unit 211 and a non-occurrence area specifying unit 412. This noise reduction device 400 is a device that reduces high frequency noise included in the electro-oculography original signal, and uses a low pass filter in the filtering unit 430.

In FIG. 11, the same components as those described in the above embodiments are given the same reference numerals, and their description is omitted.

The non-occurrence area specifying unit 412 includes an internal memory (not shown) storing a saccade detection signal of a predetermined time, and obtains saccade non-occurrence area information (that is, information for specifying a non-occurrence area) using the saccade detection signal of the predetermined time stored in the internal memory. For instance, the non-occurrence area specifying unit 412 may specify a temporally continuous area which includes a sample subject to filtering in the filtering unit 430 and in which no saccadic movement occurs, as a saccade non-occurrence area.

Figure 12:
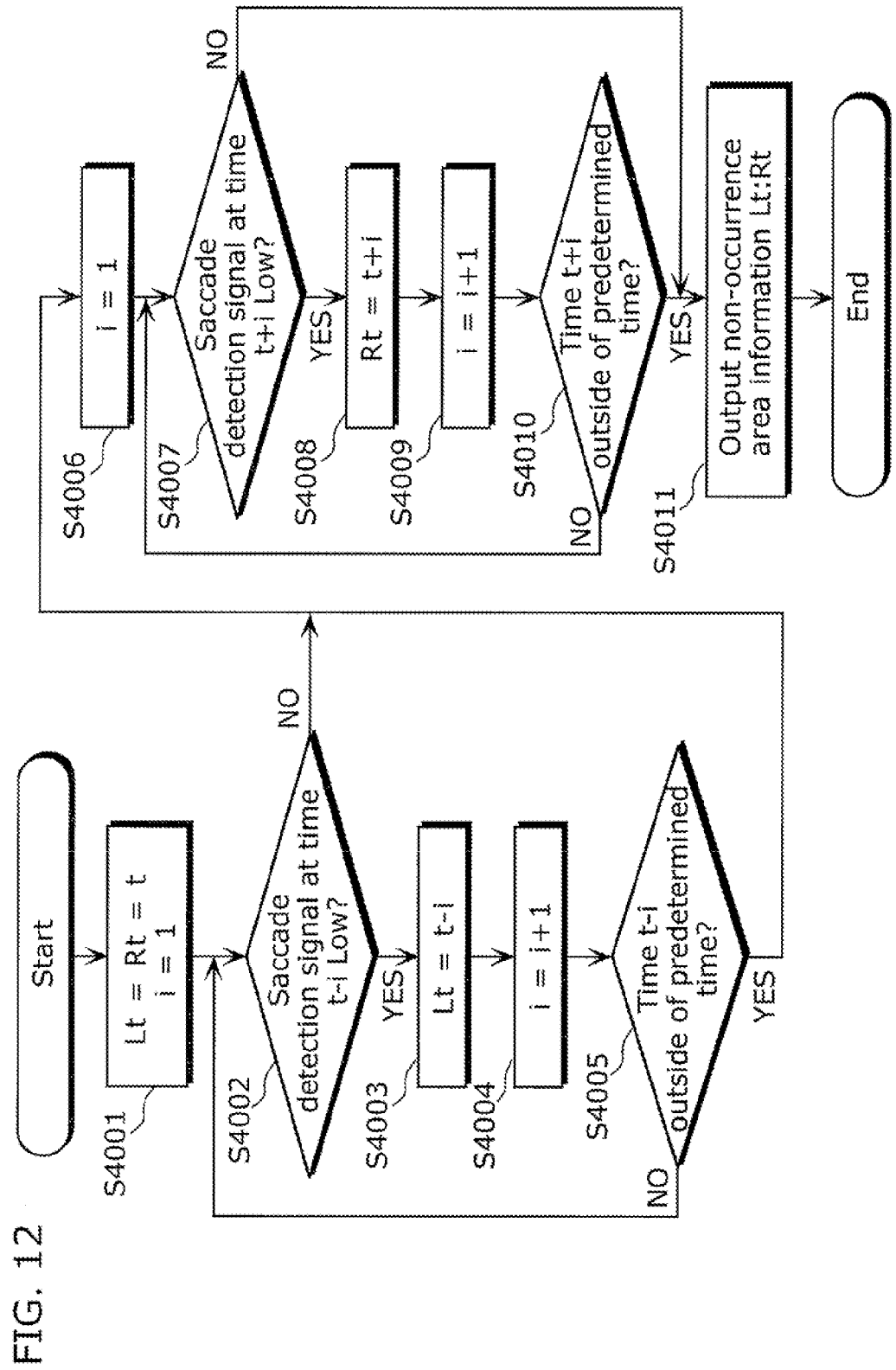
FIG. 12 is a flowchart showing an operation of a non-occurrence area specifying unit according to Embodiment 4.

A detailed procedure is described below, with reference to FIG. 12. First, the non-occurrence area specifying unit 412 designates the saccade non-occurrence area to be from time Lt to time Rt, and sets Lt and Rt to current sampling time t (a time of a sample subject to filtering) (Step S4001). Next, the non-occurrence area specifying unit 412 determines whether or not the saccade detection signal at time (t−i) is Low (Step S4002). When the saccade detection signal is Low, the non-occurrence area specifying unit 412 updates Lt by setting time (t−i) as Lt (Step S4003). The non-occurrence area specifying unit 412 then adds 1 to i (Step S4004), and checks the saccade detection signal at next time (t−i) (Step S4005). When time (t−i) is outside of the predetermined time or the saccade detection signal at time (t−i) is High, the non-occurrence area specifying unit 412 goes to Step S4006 to update Rt.

The non-occurrence area specifying unit 412 resets i to 1 (Step S4006), and determines whether or not the saccade detection signal at time (t+i) is Low (Step S4007). When the saccade detection signal is Low, the non-occurrence area specifying unit 412 updates Rt by setting time (t+i) as Rt (Step S4008). The non-occurrence area specifying unit 412 then adds 1 to i (Step S4009), and checks the saccade detection signal at next time (t+i) (Step S4010). When time (t+i) is outside of the predetermined time or the saccade detection signal at time (t+i) is High, the non-occurrence area specifying unit 412 outputs the saccade non-occurrence area information showing the area from time Lt to time Rt (Step S4011).

Figure 13A:
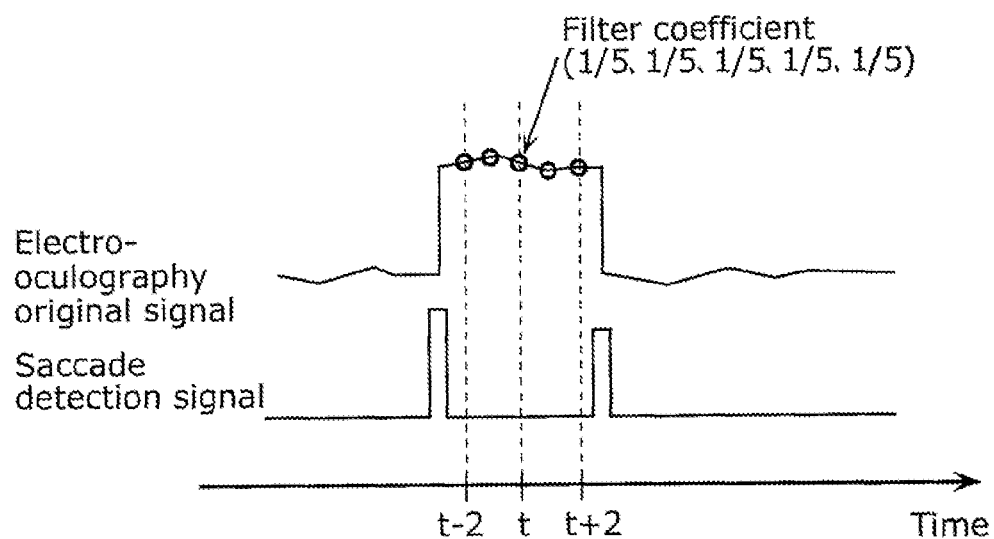
FIG. 13A is a diagram showing an example of filter coefficient determination by a control unit according to Embodiment 4.
Figure 13B:
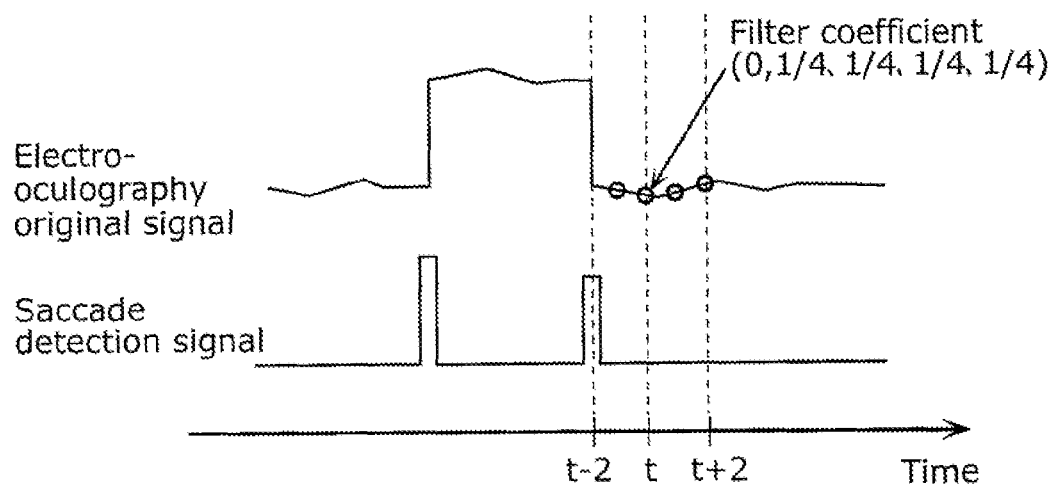
FIG. 13B is a diagram showing an example of filter coefficient determination by the control unit according to Embodiment 4.

The control unit 420 determines a filter coefficient to be applied to the electro-oculography original signal in the filtering unit 430 which is a low pass filter, using the saccade non-occurrence area information output from the non-occurrence area specifying unit 412. Suppose a smoothing filter with a filter length of 5 is used. In the case where the saccade non-occurrence area for sampling time t is from time (t−2) to time (t+2), ($1/5$, $1/5$, $1/5$, $1/5$, $1/5$) are output as filter coefficients, as shown in FIG. 13A. In the case where the saccade non-occurrence area for sampling time t is from time (t−1) to time (t+2), on the other hand, (0, ¼, ¼, ¼, ¼) are output as filter coefficients, as shown in FIG. 13B. Thus, the control unit 420 adaptively controls the filter coefficients on the basis of the saccade non-occurrence area information.

That is, the control unit 420 sets a filter coefficient of a sample not included in the non-occurrence area (a sample at time (t−2) in the example shown in FIG. 13B), to 0. This makes it possible to eliminate the influence of the sample at time (t−2) having an extremely large signal level, when reducing high frequency noise of the sample at time t through the low pass filter.

The filtering unit 430 applies the low pass filter to the electro-oculography original signal using the filter coefficients output from the control unit 420, to output the electro-oculography signal in which high frequency noise has been reduced.

Figure 14:
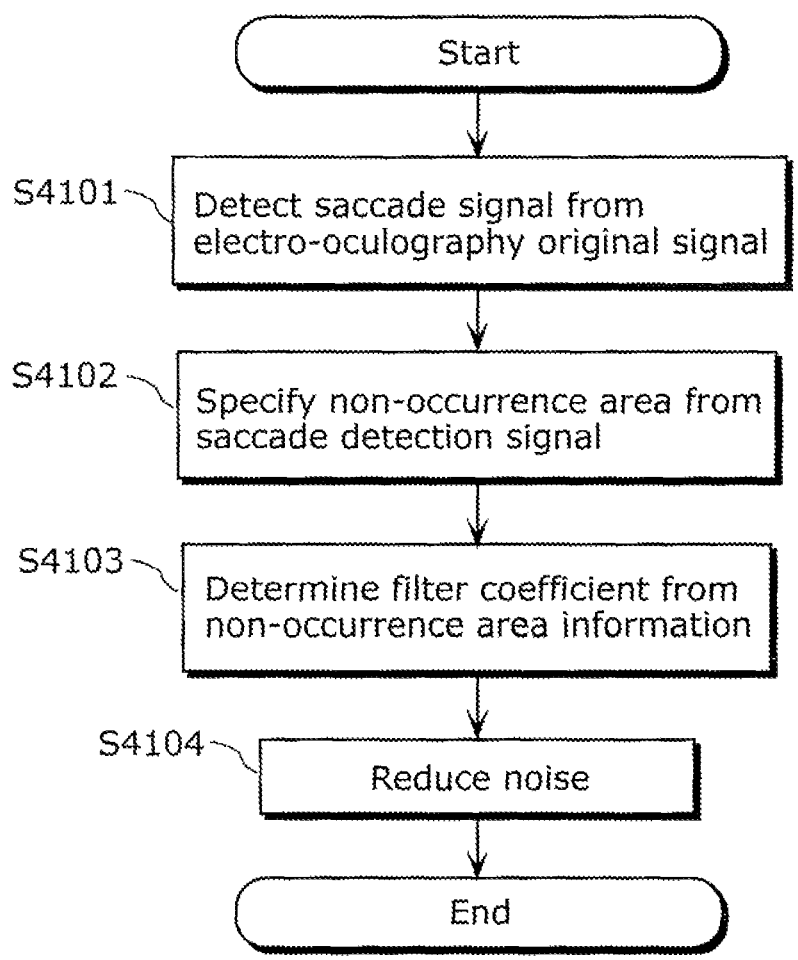
FIG. 14 is a flowchart showing an operation of the noise reduction device according to Embodiment 4.

An overall procedure by which the noise reduction device 400 according to Embodiment 4 described above outputs the electro-oculography signal is described below, with reference to FIG. 14.

First, the noise reduction device 400 obtains the saccade signal from the electro-oculography original signal (Step S4101). Next, the noise reduction device 400 obtains the saccade non-occurrence area information from the saccade detection signal (Step S4102). The noise reduction device 400 then determines the filter coefficient of the low pass filter, from the obtained non-occurrence area information (Step S4103). The noise reduction device 400 performs filtering using the determined filter coefficient, thereby reducing high frequency noise (Step S4104).

According to Embodiment 4 described above, the saccade non-occurrence area information is obtained from the electro-oculography original signal, and the filter coefficient of the low pass filter is adaptively controlled on the basis of the non-occurrence area information. This enables high frequency noise in the electro-oculography original signal to be reduced by a simpler method.

Moreover, the low pass filter is applied using only the samples included in the saccade non-occurrence area, so that high frequency noise can be reduced while protecting the saccade signal.

(Embodiment 5)

Embodiment 5 of the present invention relates to a device and method for reducing high frequency noise in particular, in order to achieve an improved S/N ratio in electro-oculography measurement. Embodiment 5 describes a device and method for separating high frequency noise from the electro-oculography original signal by using the saccade detection signal and the amplitude of the saccade signal.

Figure 15:
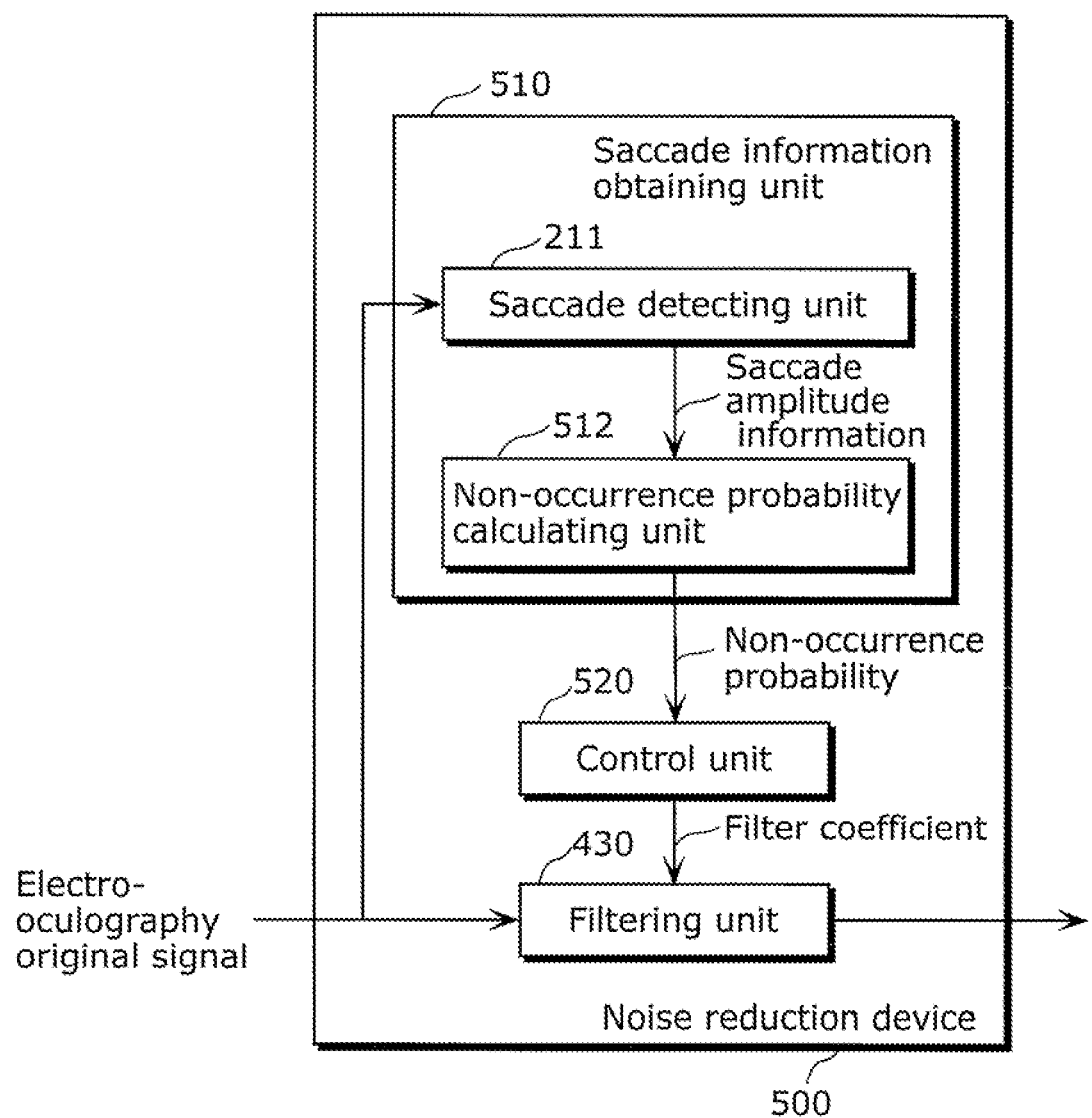
FIG. 15 is a block diagram of a noise reduction device according to Embodiment 5.

FIG. 15 is a block diagram showing a structure of a noise reduction device 500 according to Embodiment 5 of the present invention. The noise reduction device 500 according to Embodiment 5 includes a saccade information obtaining unit 510, a control unit 520, and the filtering unit 430. The saccade information obtaining unit 510 includes the saccade detecting unit 211 and a non-occurrence probability calculating unit 512. This noise reduction device 500 is a device that reduces high frequency noise included in the electro-oculography original signal, and uses a low pass filter in the filtering unit 430.

In FIG. 15, the same components as those described in the above embodiments are given the same reference numerals, and their description is omitted.

The saccade detecting unit 211 outputs the saccade detection signal indicating the presence or absence of a saccade, and the amplitude of the saccade signal. As a method for detecting the amplitude of the saccade signal from the electro-oculography original signal, there is a method of applying each of maximum value filtering and minimum value filtering to the electro-oculography original signal and calculating a difference between results of the two filtering operations. This processing will be described in detail later.

The non-occurrence probability calculating unit 512 includes an internal memory (not shown) storing an amplitude of a saccade signal and a saccade detection signal of a predetermined time, and calculates a saccade non-occurrence probability using the amplitude of the saccade signal and the saccade detection signal of the predetermined time stored in the internal memory. For instance, the non-occurrence probability calculating unit 512 may set the saccade non-occurrence probability of an area defined by the saccade detection signal within the predetermined time to 1, and decrease the non-occurrence probability according to the amplitude of the saccade signal each time the saccade detection signal becomes High.

The non-occurrence probability mentioned here is a probability that no saccade actually occurs in a sample position shown by the saccade detection signal. That is, the non-occurrence probability is higher when the amplitude of the corresponding saccade signal is smaller. On the other hand, the non-occurrence probability is lower when the amplitude of the corresponding saccade signal is larger.

Figure 16:
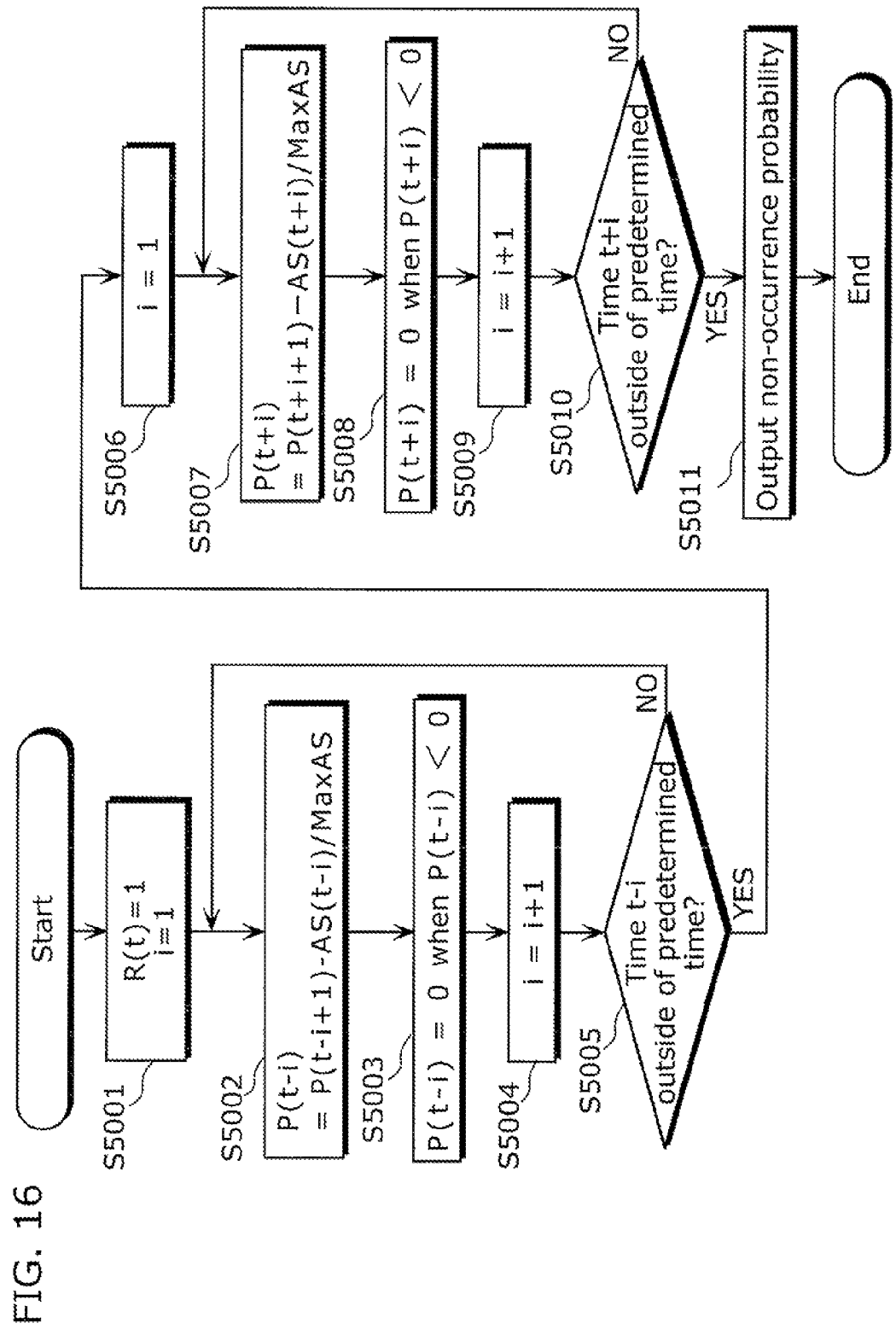
FIG. 16 is a flowchart showing an operation of a non-occurrence probability calculating unit according to Embodiment 5.

A detailed procedure is described below, with reference to FIG. 16. First, the non-occurrence probability calculating unit 512 sets a saccade non-occurrence probability P(t) at time t to 1 (Step S5001). Next, the non-occurrence probability calculating unit 512 decreases the saccade non-occurrence probability, by setting a saccade non-occurrence probability P(t−i) at time (t−i) to be a result of subtracting AS(t−i)/MaxAS from a saccade non-occurrence probability P(t−i+1) at time (t−i+1) (Step S5002). Here, AS(t−i) is the amplitude of the saccade signal at time (t−i), and MaxAS is a maximum amplitude of the saccade signal determined beforehand in electro-oculography measurement.

In the case where the amplitude AS(t−i) of the saccade signal is 0, that is, in the case where no saccade occurs, P(t−i+1) is copied to P(t−i). When P(t−i) is smaller than 0, the non-occurrence probability calculating unit 512 clips P(t−i) to 0 (Step S5003). The non-occurrence probability calculating unit 512 then adds 1 to i (Step S5004), and calculates a saccade non-occurrence probability at next is time (t−i).

When time (t−i) is outside of the predetermined time (Step S5005), the non-occurrence probability calculating unit 512 calculates a saccade non-occurrence probability P(t+i) at time (t+i) in sequence, according to the same procedure (Steps S5006 to S5009). When time (t+i) is outside of the predetermined time (Step S5010), the non-occurrence probability calculating unit 512 outputs the calculated non-occurrence probability (Step S5011).

Though MaxAS is the maximum amplitude of the saccade signal determined beforehand in electro-oculography measurement in this embodiment, MaxAS may be updated if the amplitude of the saccade signal exceeding this value is measured during electro-oculography measurement.

The control unit 520 determines a filter coefficient to be applied to the electro-oculography original signal in the filtering unit 430 which is a low pass filter, using the saccade non-occurrence probability output from the non-occurrence probability calculating unit 512. For example, when a smoothing filter with a filter length of n is used as the low pass filter, the control unit 520 calculates a filter coefficient at time (t+i), according to Expression 1 given below.

[Math. 1]

$$a(t+i) = \frac{P(t+i)}{\sum_{k=-\frac{n}{2}}^{\frac{n}{2}} P(t+k)}$$ (Expression 1)

Figure 17A:
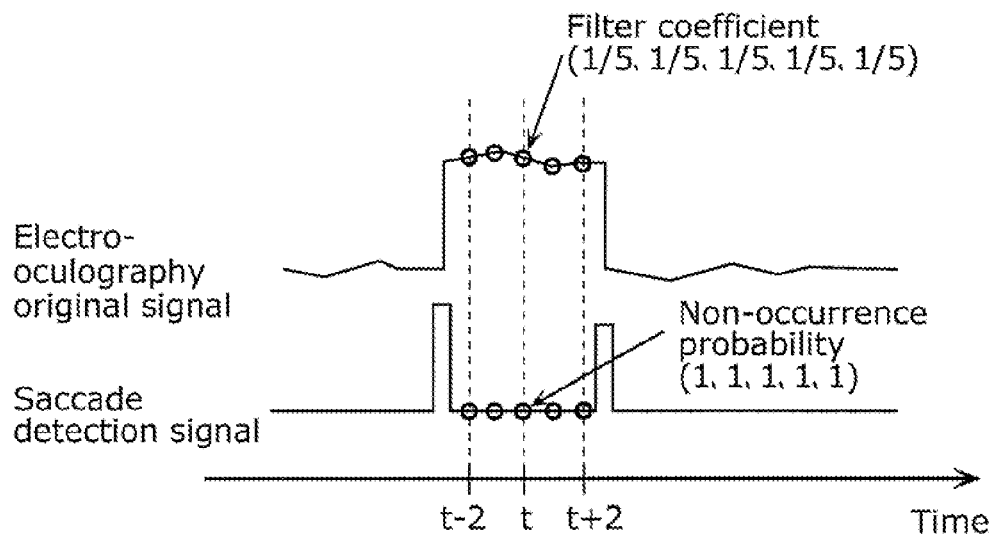
FIG. 17A is a diagram showing an example of filter coefficient determination by a control unit according to Embodiment 5.
Figure 17B:
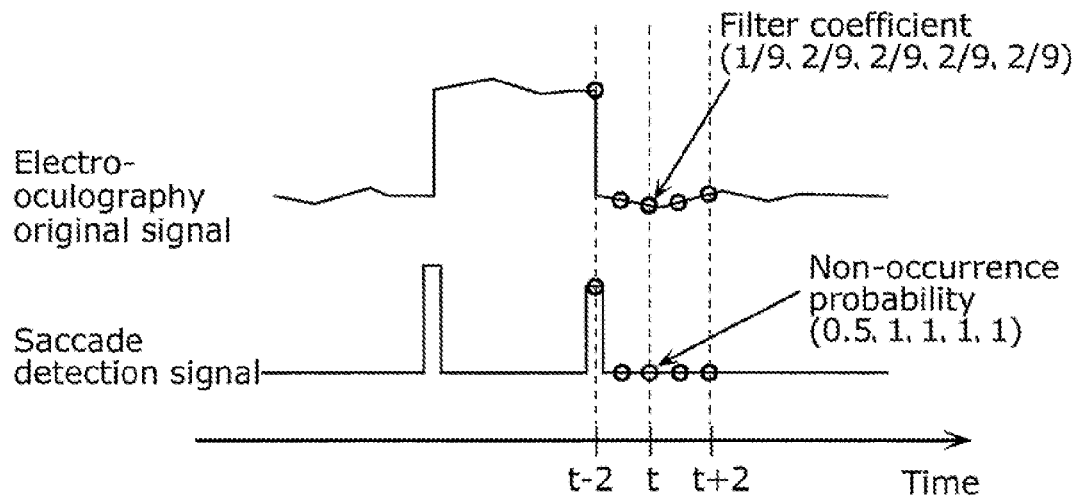
FIG. 17B is a diagram showing an example of filter coefficient determination by the control unit according to Embodiment 5.

Suppose a smoothing filter with a filter length of 5 is used. In the case where the saccade non-occurrence probabilities for sampling time t are (1, 1, 1, 1, 1), (⅕, ⅕, ⅕, ⅕, ⅕) are calculated as filter coefficients, as shown in FIG. 17A. In the case where the saccade non-occurrence probabilities for sampling time t are (0.5, 1, 1, 1, 1), on the other hand, (⅑, 2/9, 2/9, 2/9, 2/9) are calculated as filter coefficients, as shown in FIG. 17B. Thus, the control unit 520 relatively increases a filter coefficient corresponding to a sample with a higher non-occurrence probability, and relatively decreases a filter coefficient corresponding to a sample with a lower non-occurrence probability.

Figure 18:
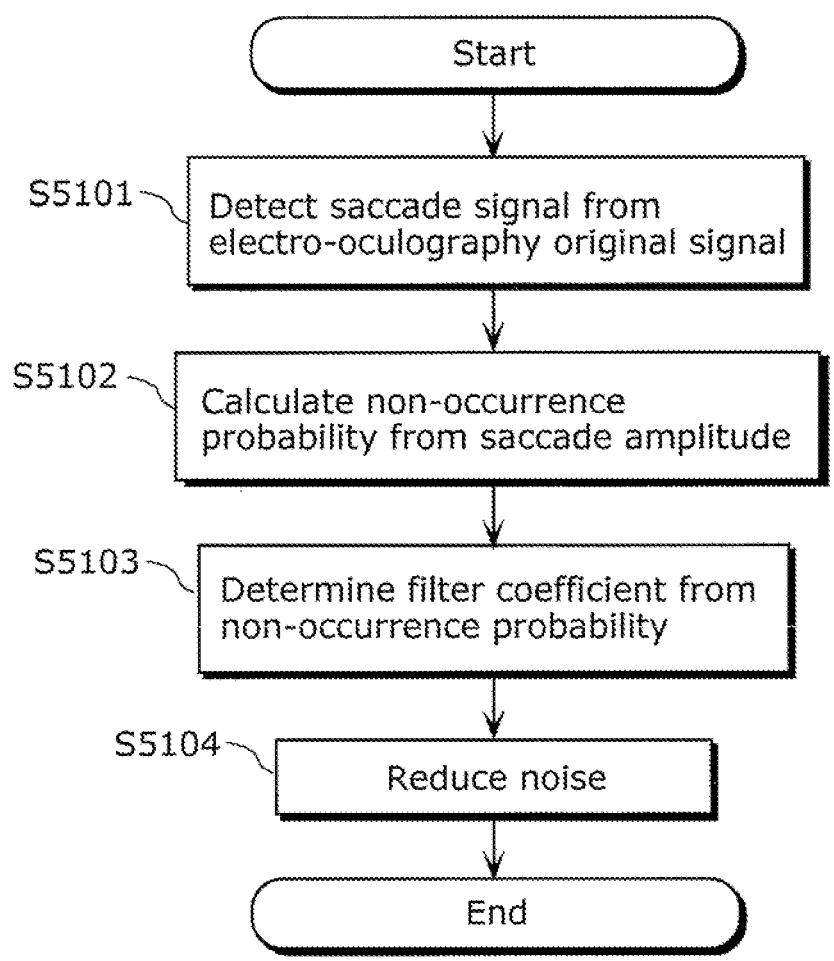
FIG. 18 is a flowchart showing an operation of the noise reduction device according to Embodiment 5.

An overall procedure by which the noise reduction device 500 according to Embodiment 5 described above outputs the electro-oculography signal is described below, with reference to FIG. 18.

First, the noise reduction device 500 obtains the saccade signal from the electro-oculography original signal (Step S5101). Next, the noise reduction device 500 obtains the saccade non-occurrence probability from the amplitude of the obtained saccade signal (Step S5102). The noise reduction device 500 then determines the filter coefficient of the low pass filter, from the obtained non-occurrence probability (Step S5103). The noise reduction device 500 performs filtering using the determined filter coefficient, thereby reducing high frequency noise (Step S5104).

According to Embodiment 5 described above, the saccade non-occurrence probability is obtained from the electro-oculography original signal, and the filter coefficient of the low pass filter is adaptively controlled on the basis of the non-occurrence probability. This enables high frequency noise in the electro-oculography original signal to be reduced by a simpler method.

Moreover, since the filter coefficient of the low pass filter is determined on the basis of the non-occurrence probability corresponding to the amplitude of the saccade signal, high frequency noise can be reduced even in the event of false saccade detection.

Though a minimum value filter and a maximum value filter are used as a method for detecting the amplitude of the saccade signal in Embodiment 5, any technique such as a high pass filter may be used so long as a saccade is detected.

The following describes a method of detecting the saccade signal in the electro-oculography original signal in the saccade detecting unit 211, in detail. Note that the saccade signal is widely used not only in the noise reduction device 100 described above, but also for detecting the user's eye movement and state in fields such as medical equipment, driver supporting equipment, user interfaces, and the like. Therefore, it is very useful to detect the saccade signal accurately and easily.

For example, the method of detecting a saccade signal from an electro-oculography original signal includes techniques disclosed by the following Patent Literatures 2 to 4.

Japanese Unexamined Patent Application Publication No. 11-276461 (Patent Literature 2) discloses a technique of detecting a saccade signal of an operator and determining attentiveness of the operator based on an occurrence frequency. It is to be noted that a high pass filter having a cutoff frequency of about 0.05 to 0.1 Hz is used for detecting a saccade signal.

Japanese Unexamined Patent Application Publication No. 9-034631 (Patent Literature 3) discloses a technique for eliminating the need for manually positioning a pointer on the display screen and a gaze-point of an operator. More specifically, when a saccade signal is detected within a predetermined period of time after a symbol for calibration is generated on the display screen, it is determined that the symbol for calibration and the gaze-point of the operator have matched, and then the position of the pointer is calibrated. It is to be noted that a high pass filter having a cutoff frequency of about 0.05 to 0.1 Hz is used for detecting a saccade signal.

Japanese Unexamined Patent Application Publication No. 2002-272693 (Patent Literature 4) discloses a technique for detecting an end point of a saccadic movement on the basis of an eye-movement signal. Then, each time a saccadic movement ends, brain waves within a predetermined period of time from the end point are consecutively stored for plural parts of the brain as unit brain waves, so that an eye fixation related potential is obtained. It is to be noted that a saccade signal is detected by determining whether or not the direction of an eye movement has changed after continuously stayed the same within a predetermined period of time.

Figure 20:
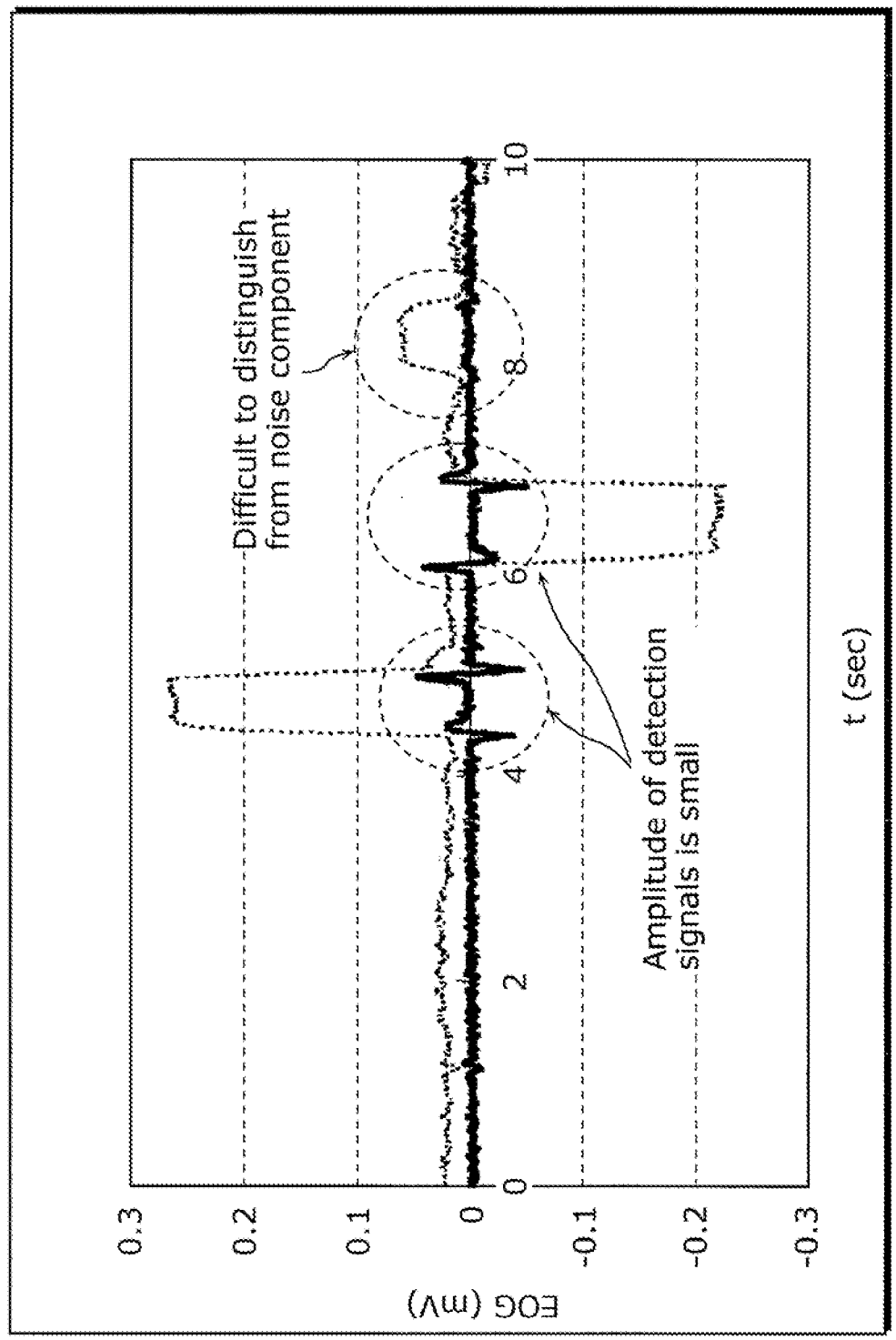
FIG. 20 is a diagram showing an electro-oculography signal obtained by applying high pass filter processing to the electro-oculography signal shown in FIG. 19.

The methods of detecting a saccade as disclosed in Patent Literatures 2 to 4 may be adopted for the saccade detecting unit 211 shown in FIG. 3. However, with the methods as shown in Patent Literatures 2 and 3, a saccade signal is detected by using a high pass filter. When the electro-oculography original signal shown in FIG. 19 passes a high pass filter, an amplitude of a saccade signal decreases in some cases as shown in FIG. 20. It can be difficult especially for a saccade signal with a small amplitude to be distinguished from a noise component.

Further, with the method shown in Patent Literature 4, there is a possibility of false detection such as in the case where, when detecting the direction of eye movement, the direction of eye movement is not determined as continuously the same even during a saccade due to an effect of a noise component or the like.

In view of this, Embodiments 6 to 9 of the present invention describe a method of detecting a saccade signal from an electro-oculography original signal of a user accurately and easily. Though an example of detecting a saccade signal from an electro-oculography original signal including a drift signal obtained from electrodes placed on the user is described below, the same applies to the case of detecting a saccade signal from an electro-oculography signal from which noise has been removed as described in Embodiment 14.

(Embodiment 6)

Figure 21:
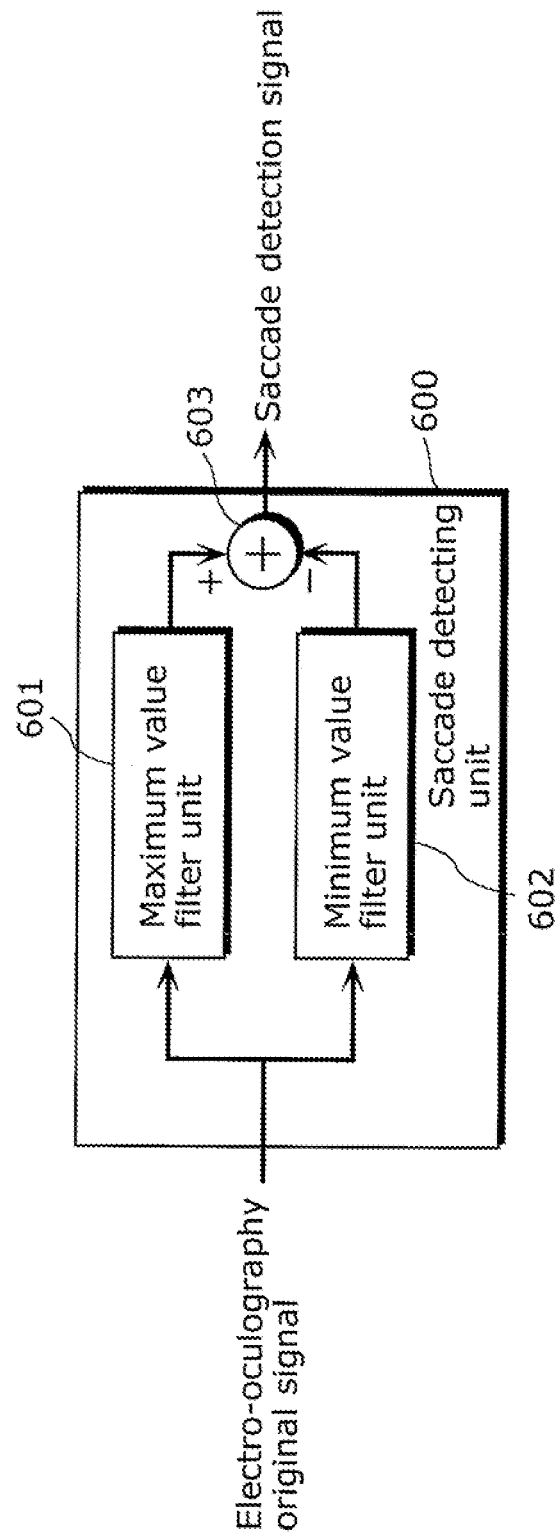
FIG. 21 is a block diagram of a saccade detecting unit according to Embodiment 6.

FIG. 21 is a block diagram showing a structure of a saccade detecting unit 600 according to Embodiment 6 of the present invention. The saccade detecting unit 600 shown in FIG. 21 includes: a maximum value filter unit (first filtering unit) 601 which performs maximum value filtering on an electro-oculography original signal; a minimum value filter unit (second filtering unit) 602 which performs minimum value filtering on the electro-oculography original signal; and a subtraction unit 603.

More specifically, the maximum value filter unit 601 and the minimum value filter unit 602 are connected in parallel to each other. The maximum value filter unit 601 performs the maximum value filtering on the electro-oculography original signal and outputs a first electro-oculography signal. The minimum value filter unit 602 performs the minimum value filtering on the electro-oculography original signal and outputs a second electro-oculography signal. Then, the subtraction unit 603 subtracts the second electro-oculography signal from the first electro-oculography signal to generate an output signal.

Figure 63:
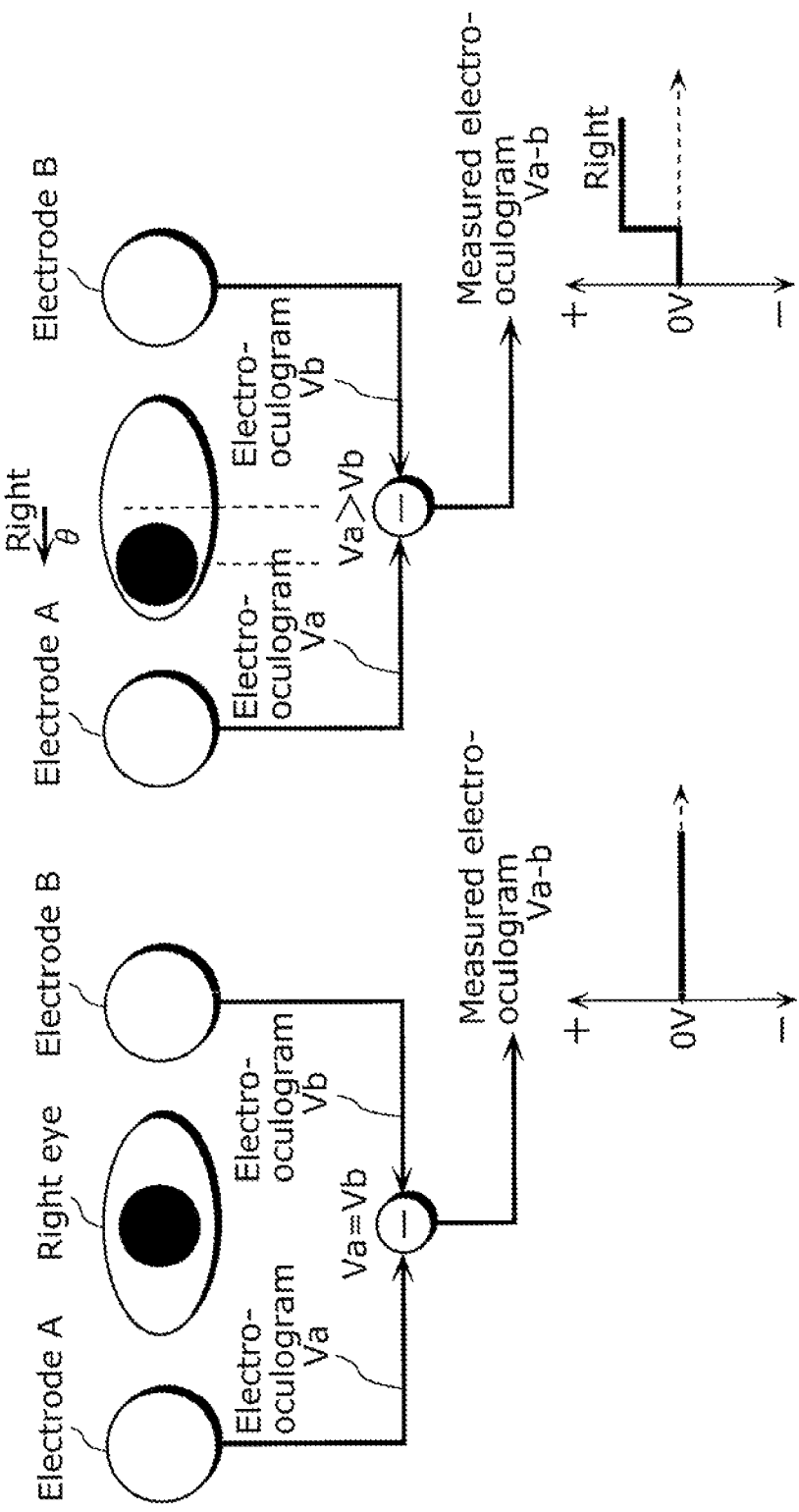
FIG. 63A is a diagram showing a state where the user's eyeball faces front.
FIG. 63B is a diagram showing a state where the user's eyeball faces right.

It is to be noted that the present invention is intended for the case where a blink component of a user is not included in the electro-oculography original signal, such as in the case where electrodes are placed on the right and left of an eyeball as shown in FIGS. 63A and 63B, or in the measuring method where electrodes are placed at a position away from the eye. Description will be given as to detection of a saccade signal when such a measuring method is used.

Next, the processing of the maximum value filter unit 601 as shown in FIG. 21 will be described. The maximum value filter unit 601 performs filtering described below on an electro-oculography original signal f (x).

$$fmax(x)=max(fmax(x),f(x+i))$$

When n is an odd number, the following applies. (−n/2<i<n/2)

When n is an even number, one of the followings applies. (−n/2≦i<n/2) or (−n/2<i≦n/2)

Here, f max (x) is an electro-oculography signal after the maximum value filtering is performed, n is the number of filter taps, and i is an integer. Further, max (a, b) is a function that returns a larger value of a and b. Thus, in the maximum value filtering, a sampling value is output which has the largest amplitude of n samples centering on an arbitrary sample f (x) in the electro-oculography original signal. The first electro-oculography signal can be obtained by performing the above processing on each of the samples of the electro-oculography original signal.

Figure 22:
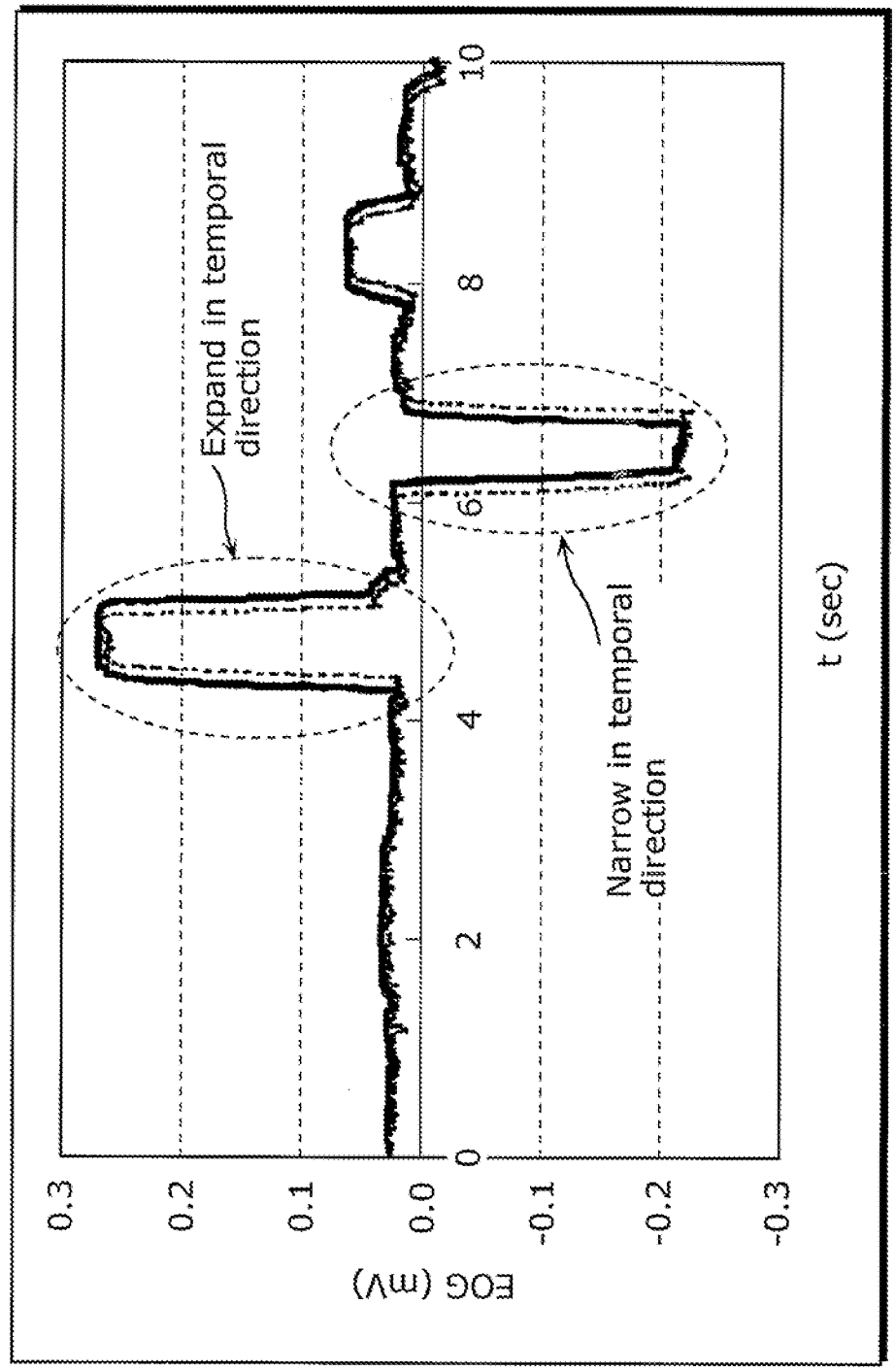
FIG. 22 is a diagram showing an electro-oculography signal obtained by applying maximum value filtering (unit processing period=0.25 seconds) to the electro-oculography signal shown in FIG. 19.

FIG. 22 shows an example of performing the above-described filtering processing on the electro-oculography original signal of FIG. 19. It is to be noted that the unit processing period for the maximum value filtering is set to 0.25 seconds for detecting the saccade signal from the electro-oculography original signal. It is to be noted that the unit processing period indicates a time interval including a sample on which a single maximum value filtering is performed. Further, the number of filter taps n of the maximum value filter unit 601 is the number of samples included in the unit processing period (0.25 seconds). Thus, the number of filter taps n can be calculated using the unit processing period and a sampling frequency when A/D conversion is performed on the electro-oculography original signal.

Figure 23:
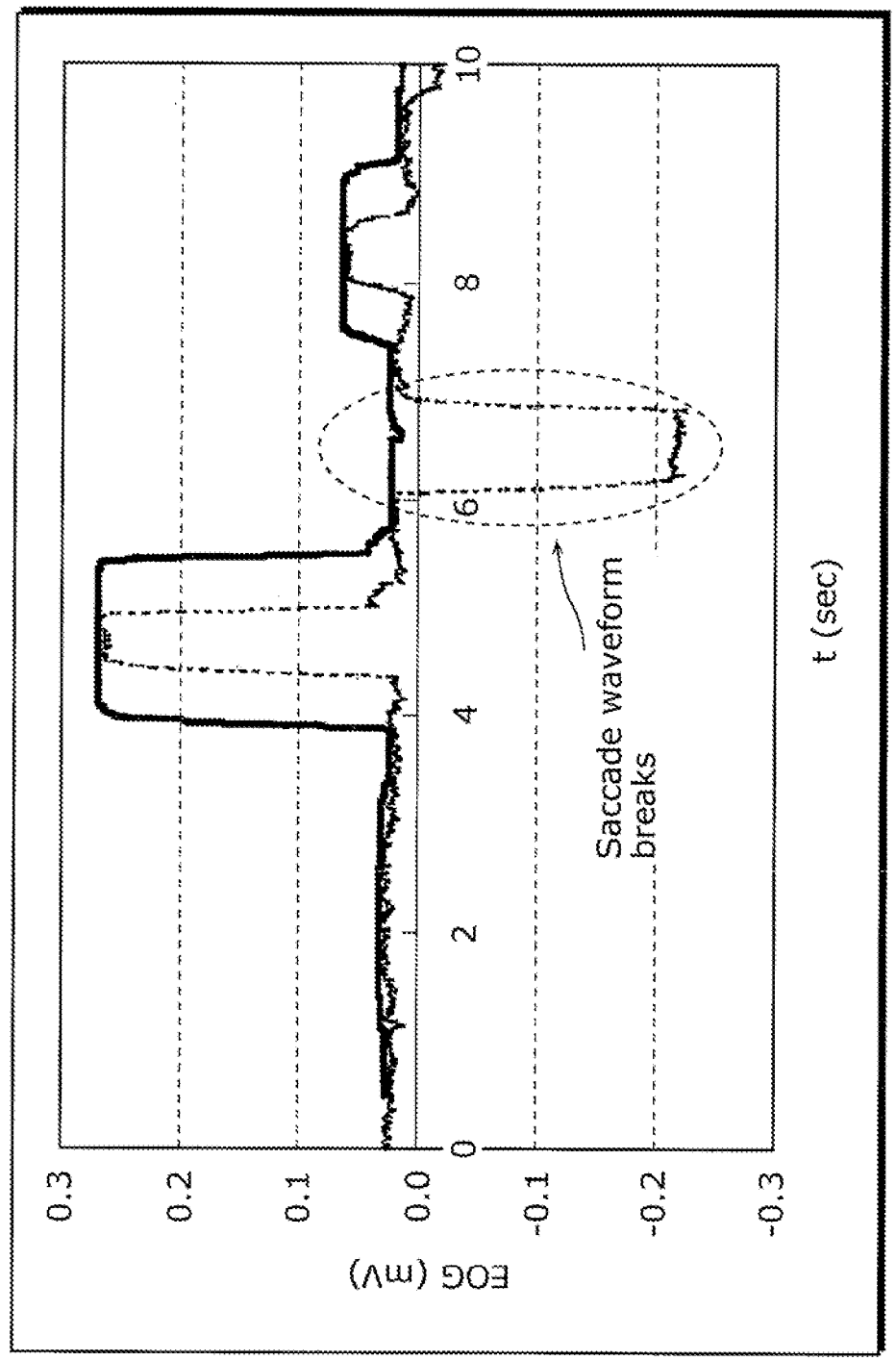
FIG. 23 is a diagram showing an electro-oculography signal obtained by applying maximum value filtering (unit processing period=1.0 second) to the electro-oculography signal shown in FIG. 19.

As shown in FIG. 22, when the maximum value filtering is performed on the electro-oculography original signal, a plus signal expands in the temporal direction and a minus signal narrows in the temporal direction. However, when the unit processing period of the maximum value filter unit 601 is set to be larger than an amount of time of one typical visual fixation (0.3 to 0.4 seconds, approximately), the saccade waveform in the minus direction breaks as shown in FIG. 23. FIG. 23 is an example of performing the maximum value filtering with the unit processing period being 1.0 second. Since the saccade signal cannot be detected when the saccade waveform breaks as shown in FIG. 23, it is necessary to set the unit processing period of the maximum value filter unit 601 to be shorter than the amount of time of one typical visual fixation.

It is to be noted that, although an example in which the unit processing period of the maximum value filtering is 0.25 seconds has been described in Embodiment 6, the unit processing period may be any value as long as it is shorter than the amount of time of one typical visual fixation.

Next, the processing of the minimum value filter unit 602 will be described. The minimum value filter unit 602 performs filtering described below on the electro-oculography original signal f (x).

$$fmin(x)=min(fmin(x),f(x+i))$$

When n is an odd number, the following applies. (−n/2<i<n/2)

When n is an even number, one of the followings applies. (−n/2≦i<n/2) or (−n/2<i≦n/2)

Here, f min (x) is an electro-oculography signal after the minimum value filtering is performed, n is the number of filter taps, and i is an integer. Further, min (a, b) is a function that returns a smaller value of a and b. Thus, in the minimum value filtering, a sampling value is output which has the smallest amplitude of n samples centering on an arbitrary sample f (x) in the electro-oculography original signal. The second electro-oculography signal can be obtained by performing the above processing on each of the samples of the electro-oculography original signal.

Figure 24:
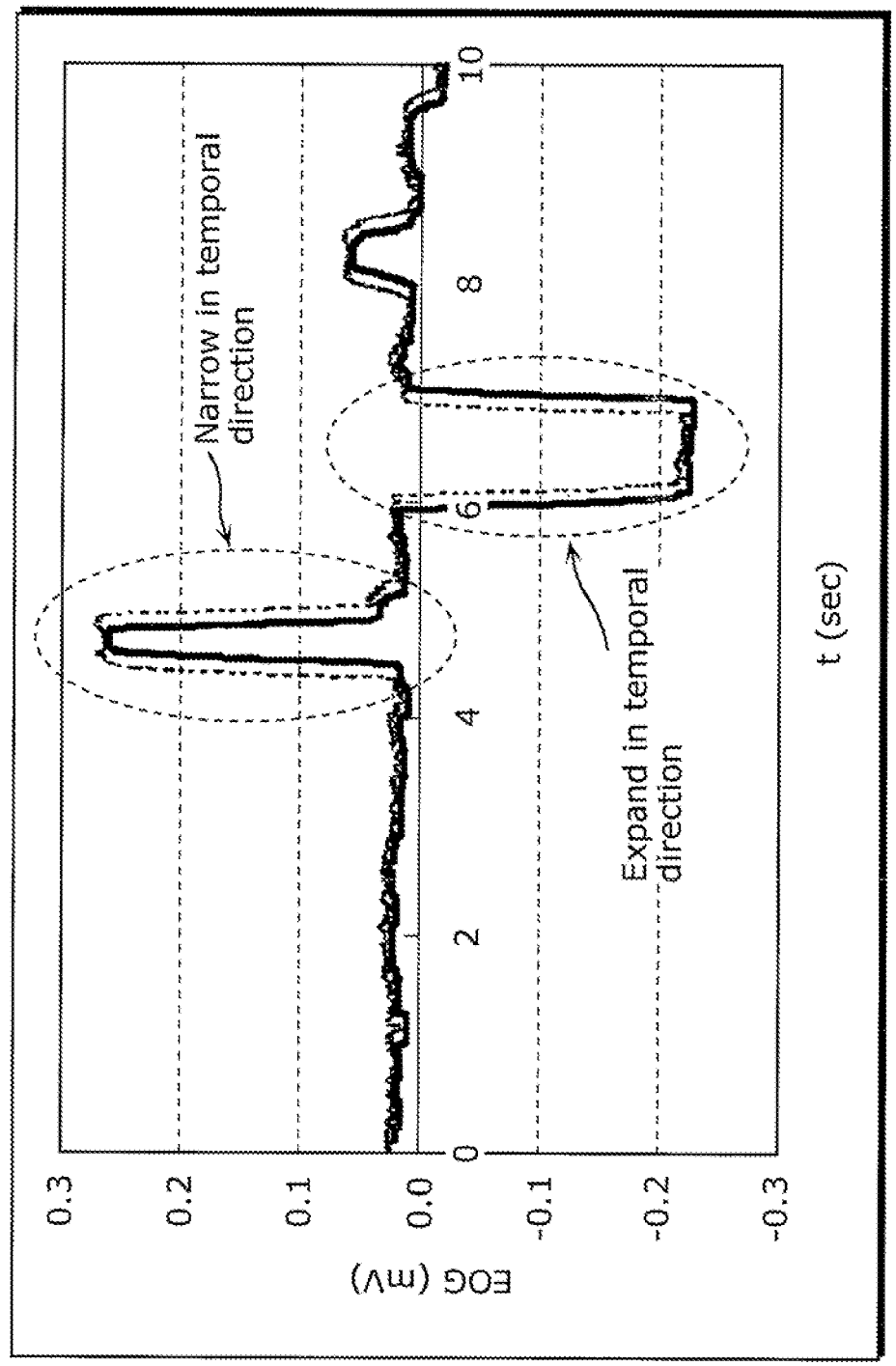
FIG. 24 is a diagram showing an electro-oculography signal obtained by applying minimum value filtering (unit processing period=0.25 seconds) to the electro-oculography signal shown in FIG. 19.

FIG. 24 shows an example of performing the above-described filtering processing on the electro-oculography original signal of FIG. 19.

In FIG. 24, the unit processing period for the minimum value filtering is set to 0.25 seconds for detecting the saccade signal from the electro-oculography original signal.

Figure 25:
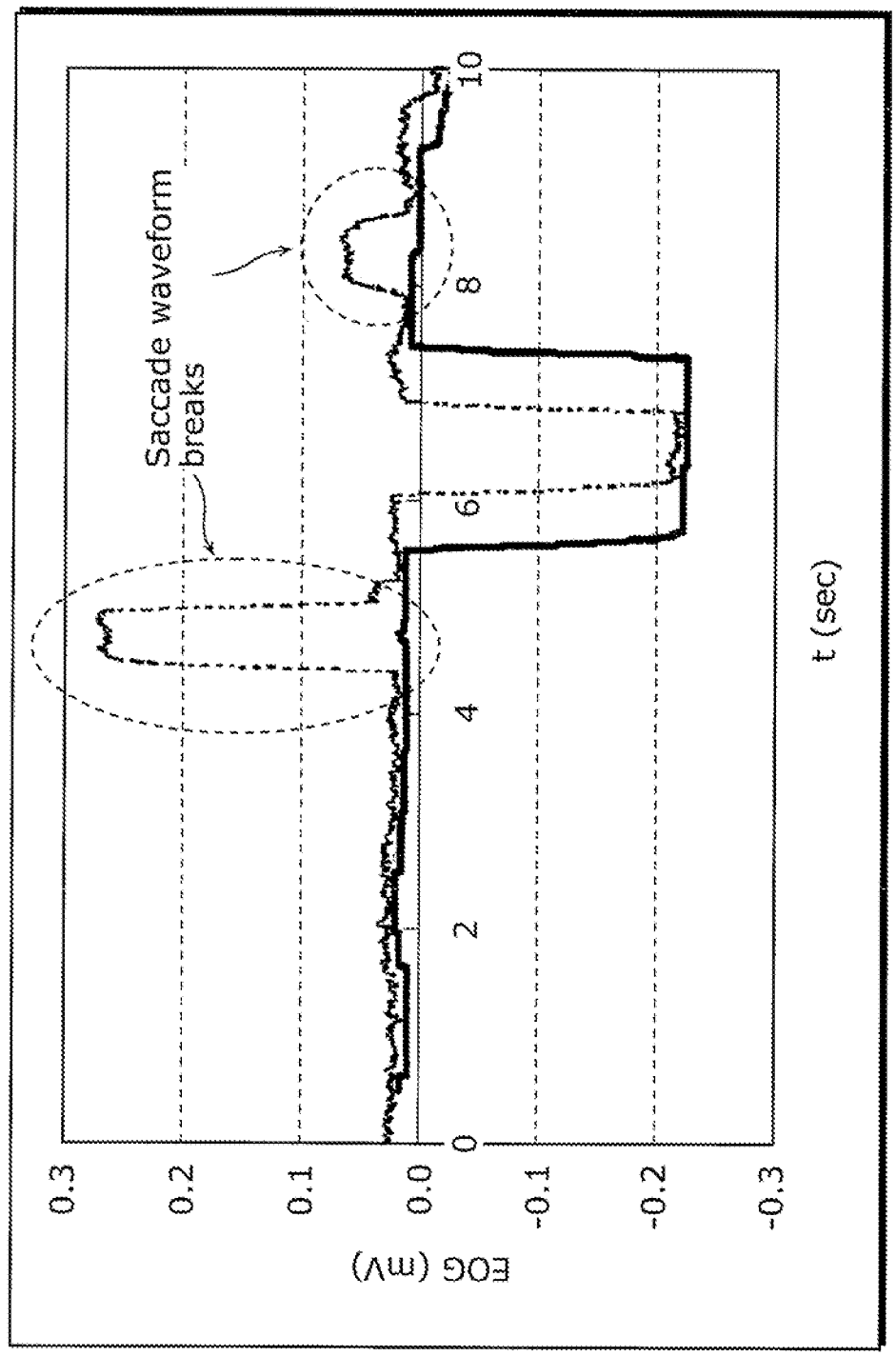
FIG. 25 is a diagram showing an electro-oculography signal obtained by applying minimum value filtering (unit processing period=1.0 second) to the electro-oculography signal shown in FIG. 19.

As shown in FIG. 24, when the minimum value filtering is performed on the electro-oculography original signal, a plus signal narrows in the temporal direction and a minus signal expands in the temporal direction. Here, when the unit processing period of the minimum value filter unit 202 is set to be larger than the amount of time of one typical visual fixation, the saccade waveform in the plus direction breaks as shown in FIG. 25. FIG. 25 is an example of performing the minimum value filtering with the unit processing period being 1.0 second. Since a saccade component cannot be detected when the saccade waveform breaks as shown in FIG. 25, it is necessary to set the unit processing period of the minimum value filter unit 602 to be shorter than the amount of time of one typical visual fixation.

It is to be noted that, although an example in which the unit processing period of the minimum value filter unit is 0.25 seconds has been described in Embodiment 6, the unit processing period may be any value as long as it is shorter than the amount of time of one typical visual fixation.

Next, the processing of the subtraction unit 603 will be described. The subtraction unit 603 subtracts the second electro-oculography signal f min (x) which has been output from the minimum value filter unit 602, from the first electro-oculography signal f max (x) which has been output from the maximum value filter unit 601, thereby extracting the saccade signal.

FIG. 26 shows a signal indicating a difference between the first electro-oculography signal shown in FIG. 22 and the second electro-oculography signal shown in FIG. 24. It can be understood by referring to FIG. 26 that the detection signal including the period of time when a saccade occurs is obtained.

The saccade detecting unit 600 generates a saccade detection signal and amplitude information on the basis of the output signal as shown in FIG. 26, and outputs the saccade detection signal and the amplitude information to the time interval calculating unit 212, the occurrence frequency calculating unit 312, the non-occurrence area specifying unit 412, or the non-occurrence probability calculating unit 512. For example, when the amount of change in sampling value within a period of time corresponding to a period of time required for a saccadic movement exceeds a predetermined threshold, it is determined that a saccadic movement has occurred and the saccade detection signal is output. Moreover, the amount of change in sampling value at this time is output as the amplitude information.

It is to be noted that, although the maximum value filter unit 601 and the minimum value filter unit 602 are used in Embodiment 6, a filter that selects a value close to the maximum value or the minimum value may be used. In this case, it is desirable to select a value approximately 90% of the maximum value or the minimum value.

Further, although Embodiment 6 describes an example in which the unit processing periods (the numbers of filter taps) of the maximum value filter unit 601 and the minimum value filter unit 602 are set to the same value, difference values may be used.

According to the structure of Embodiment 6 as described above, a saccade signal is detected by performing each of the maximum value filtering and the minimum value filtering on the electro-oculography original signal and subtracting the second electro-oculography signal on which the minimum value filtering has been performed, from the first electro-oculography signal on which the maximum value filtering has been performed. As a result, it is possible to easily obtain a saccade signal that includes the time when a saccade occurs.

(Embodiment 7)

Figure 27:
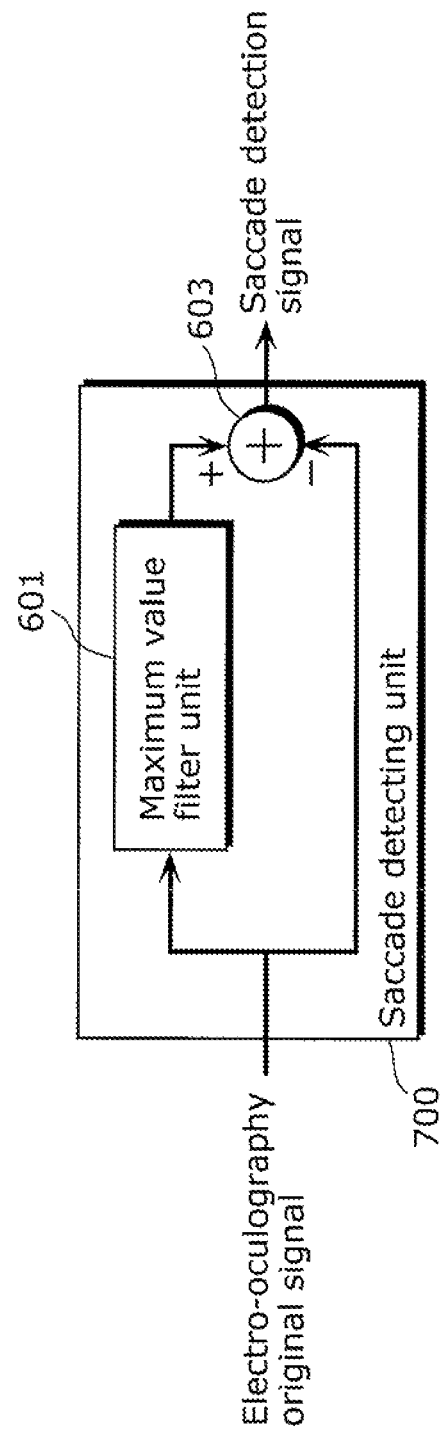
FIG. 27 is a block diagram of a saccade detecting unit according to Embodiment 7.

FIG. 27 is a block diagram showing a structure of a saccade detecting unit 700 according to Embodiment 7 of the present invention.

The saccade detecting unit 700 according to Embodiment 7 includes the maximum value filter unit (first filtering unit) 601 and the subtraction unit 603. More specifically, it is different from Embodiment 6 in that the minimum value filter unit 602 is omitted. By omitting the minimum value filter unit 602, it is possible to easily obtain a saccade signal while reducing the amount of processing.

In FIG. 27, since the structure same as the structure in FIG. 21 has already been described, the same numerals are assigned and the description that is overlapped will be omitted. In the saccade detecting unit 700 according to Embodiment 7, an electro-oculography original signal enters two paths. Then, one passes the maximum value filter unit 601 to be input into the subtraction unit 603 as the first electro-oculography signal and the other is directly input into the subtraction unit 603 as the second electro-oculography signal. Then, the subtraction unit 603 subtracts the electro-oculography original signal f (x) (corresponding to "the second electro-oculography signal") from the first electro-oculography signal f max (x) on which the maximum value filtering has been performed to output the saccade signal, which differs from Embodiment 6.

Figure 28:
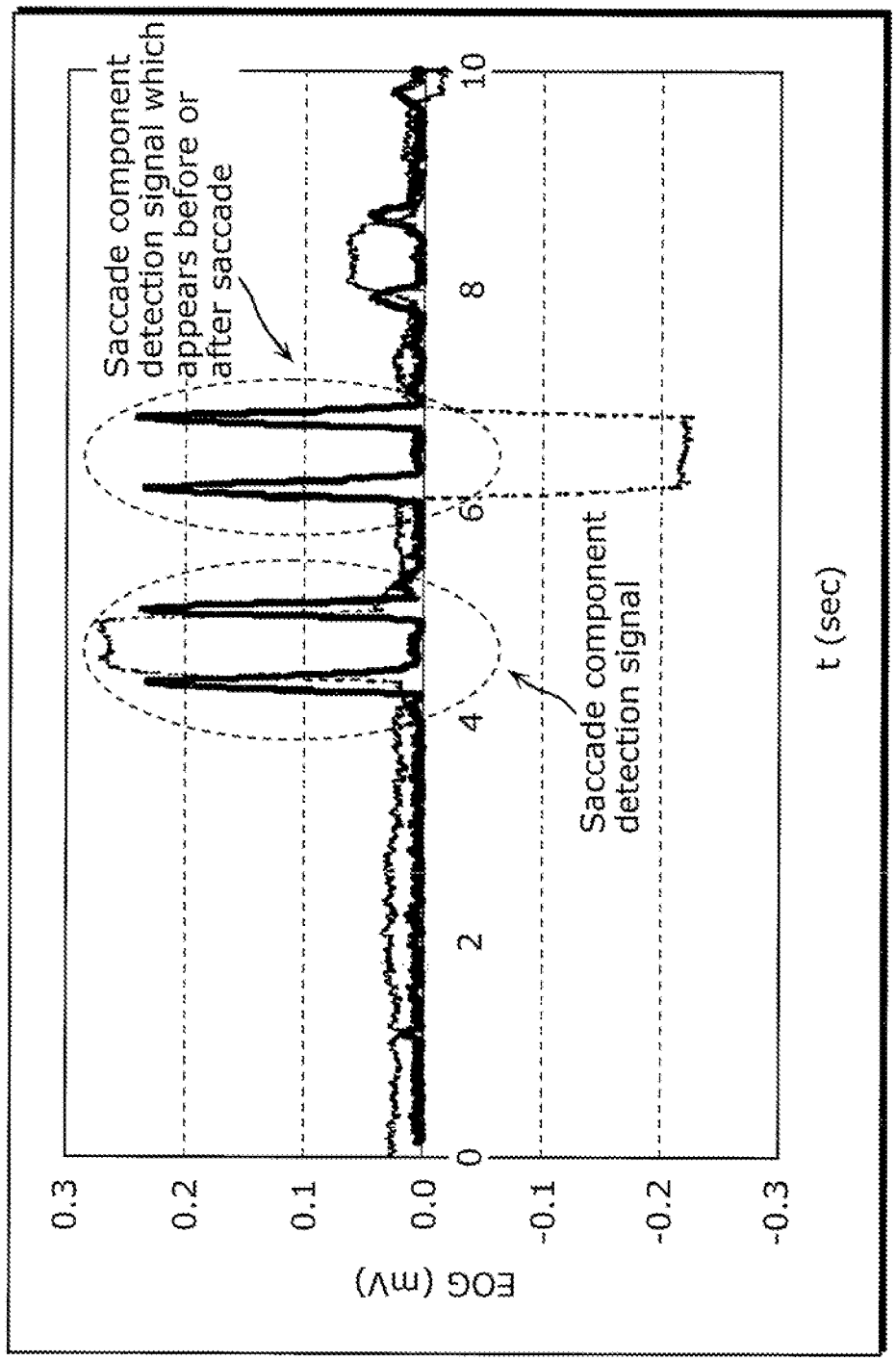
FIG. 28 is a diagram showing a saccade detection signal obtained by subtracting the electro-oculography signal shown in FIG. 19 from the electro-oculography signal shown in FIG. 22.

FIG. 28 shows a signal indicating a difference between the first electro-oculography signal on which the maximum value filtering has been performed as shown in FIG. 22 and the electro-oculography original signal shown in FIG. 19. It can be understood by referring to FIG. 28 that the detection signal is obtained when a saccade occurs.

The saccade detecting unit 700 generates a saccade detection signal and amplitude information on the basis of the output signal as shown in FIG. 28, and outputs the saccade detection signal and the amplitude information to the time interval calculating unit 212, the occurrence frequency calculating unit 312, the non-occurrence area specifying unit 412, or the non-occurrence probability calculating unit 512. For example, when the amount of change in sampling value within a period of time corresponding to a period of time required for a saccadic movement exceeds a predetermined threshold, it is determined that a saccadic movement has occurred and the saccade detection signal is output. Moreover, the amount of change in sampling value at this time is output as the amplitude information.

The detection signal of the saccade component in the minus direction, however, appears before or after the time when a saccade occurs. Thus, Embodiment 7 is effective in terms of the processing amount when obtaining an occurrence frequency and the like of a saccade, which does not require temporal information.

It is to be noted that, although the maximum value filter unit 601 is used in Embodiment 7, a filter that selects a value close to the maximum value may be used. In this case, it is desirable to select a value approximately 90% of the maximum value.

According to the structure of Embodiment 7 as described above, it is possible to obtain a saccade signal easily because the saccade signal is detected by subtracting the electro-oculography original signal from the first electro-oculography signal obtained by performing the maximum value filtering on the electro-oculography original signal.

(Embodiment 8)

Figure 29:
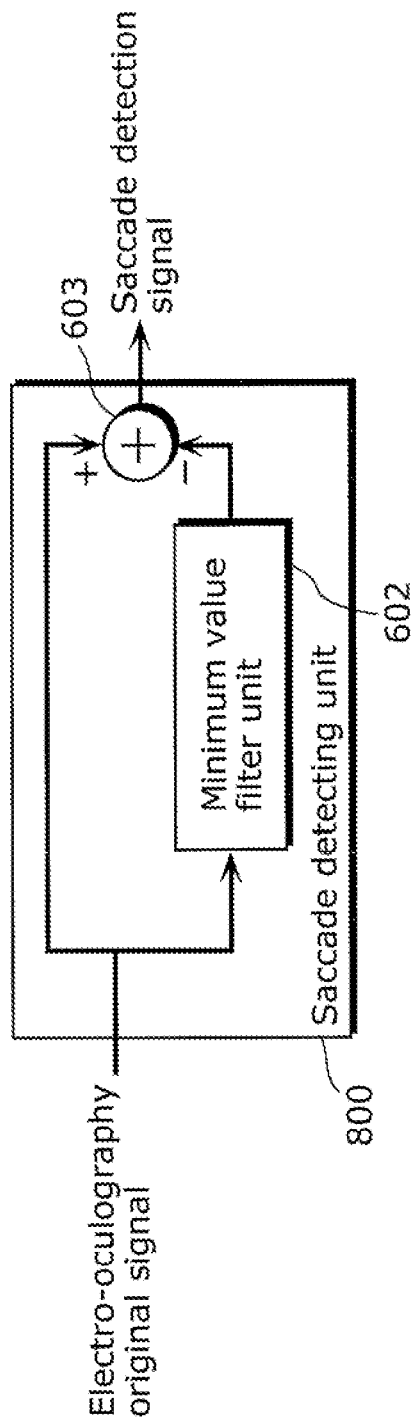
FIG. 29 is a block diagram of a saccade detecting unit according to Embodiment 8.

FIG. 29 is a block diagram showing a structure of a saccade detecting unit 800 according to Embodiment 8 of the present invention.

The saccade detecting unit 800 according to Embodiment 8 includes the minimum value filter unit (first filtering unit) 602 and the subtraction unit 603. More specifically, it is different from Embodiment 6 in that the maximum value filter unit 601 is omitted. By omitting the maximum value filter unit 601, it is possible to easily obtain a saccade signal while reducing the amount of processing.

In FIG. 29, since the structure same as the structure in FIG. 21 has already been described, the same numerals are assigned and the description that is overlapped will be omitted. In the saccade detecting unit 800 according to Embodiment 8, an electro-oculography original signal enters two paths. Then, one passes the minimum value filter unit 602 to be input into the subtraction unit 603 as the first electro-oculography signal and the other is directly input into the subtraction unit 603 as the second electro-oculography signal. Then, the subtraction unit 603 subtracts the first electro-oculography signal f min (x) on which the minimum value filtering has been performed, from the electro-oculography original signal f (x) (corresponding to "the second electro-oculography signal") to output the saccade signal, which differs from Embodiment 6.

Figure 30:
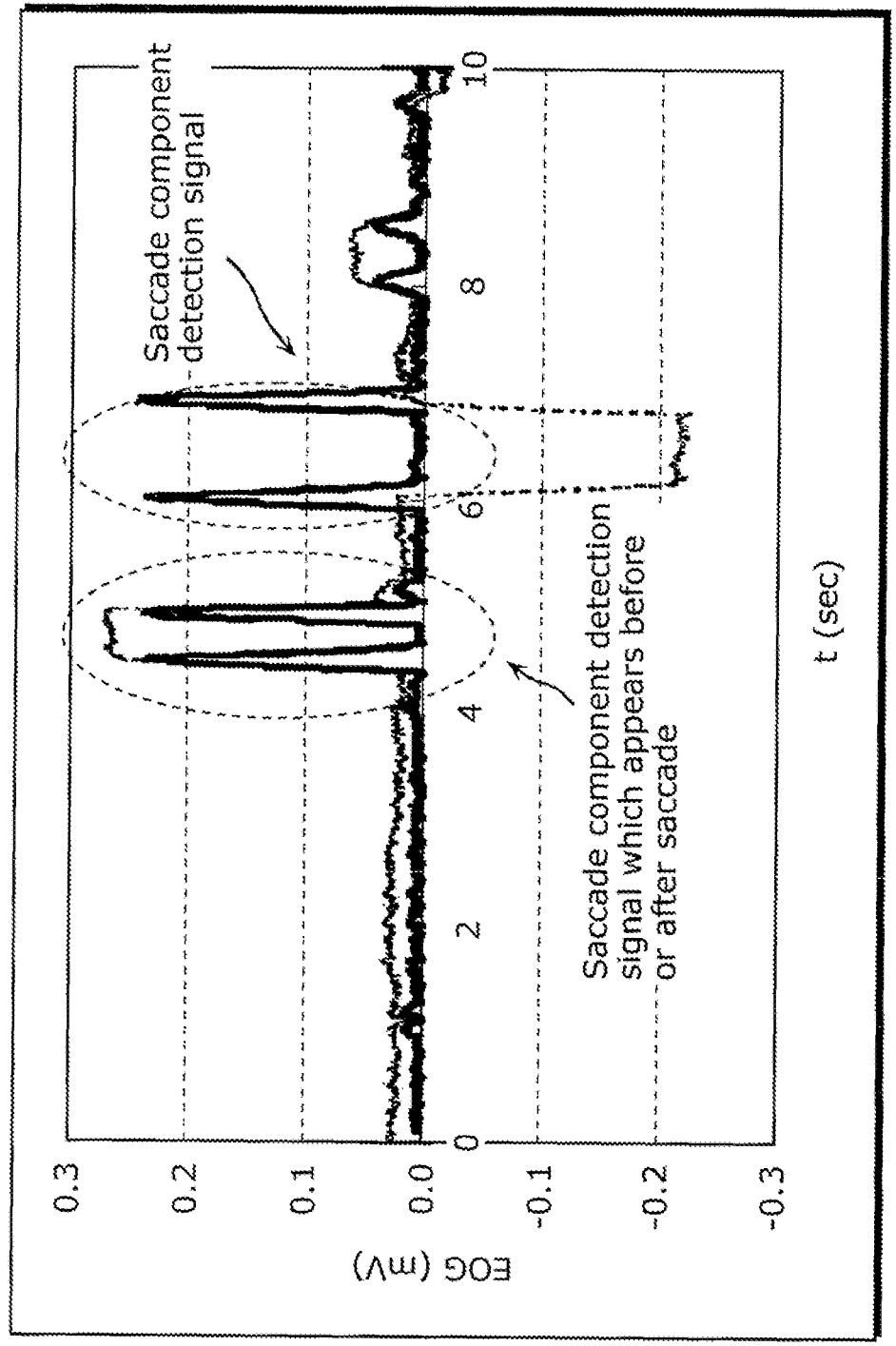
FIG. 30 is a diagram showing a saccade detection signal obtained by subtracting the electro-oculography signal shown in FIG. 24 from the electro-oculography signal shown in FIG. 19.

FIG. 30 shows a signal indicating a difference between the electro-oculography original signal shown in FIG. 19 and the second electro-oculography signal on which the minimum value filtering has been performed as shown in FIG. 24. It can be understood by referring to FIG. 30 that the detection signal is obtained when a saccade occurs.

The saccade detecting unit 800 generates a saccade detection signal and amplitude information on the basis of the output signal as shown in FIG. 30, and outputs the saccade detection signal and the amplitude information to the time interval calculating unit 212, the occurrence frequency calculating unit 312, the non-occurrence area specifying unit 412, or the non-occurrence probability calculating unit 512. For example, when the amount of change in sampling value within a period of time corresponding to a period of time required for a saccadic movement exceeds a predetermined threshold, it is determined that a saccadic movement has occurred and the saccade detection signal is output. Moreover, the amount of change in sampling value at this time is output as the amplitude information.

The saccade signal in the plus direction, however, appears before or after the time when a saccade occurs. Thus, Embodiment 8 is effective in terms of the processing amount when obtaining an occurrence frequency and the like of a saccade, which does not require temporal information.

It is to be noted that, although the minimum value filter unit 602 is used in Embodiment 8, a filter that selects a value close to the minimum value may be used. In this case, it is desirable to select a value approximately 90% of the minimum value.

According to the structure of Embodiment 8 as described above, it is possible to obtain a saccade signal easily because the saccade signal is detected by subtracting, from the electro-oculography original signal (the second electro-oculography signal), the first electro-oculography signal obtained by performing the minimum value filtering on the electro-oculography original signal.

(Embodiment 9)

Figure 31:
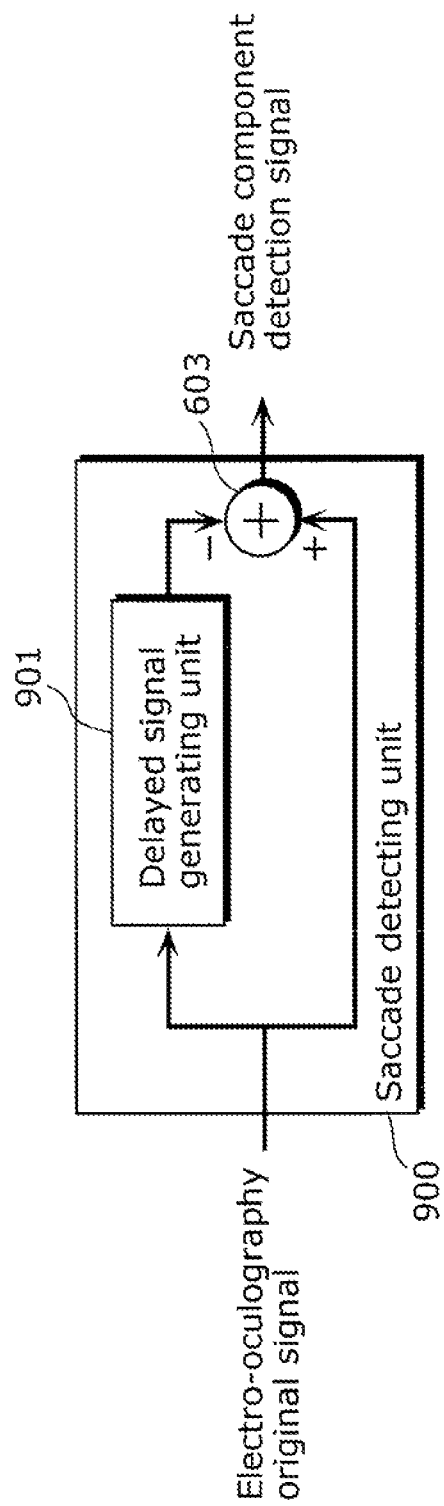
FIG. 31 is a block diagram of a saccade detecting unit according to Embodiment 9.

Next, a block diagram of a saccade detecting unit 900 according to Embodiment 9 is shown in FIG. 31.

The saccade detecting unit 900 according to Embodiment 9 includes a delayed signal generating unit 901 and the subtraction unit 603. The delayed signal generating unit 901 delays an electro-oculography original signal by a predetermined amount of time and outputs a delayed signal. Further, the electro-oculography original signal input into the saccade detecting unit 900 enters two paths. Then, one passes the delayed signal generating unit 901 to be input into the subtraction unit 603 as the delayed signal and the other is directly input into the subtraction unit 603. Then, the subtraction unit 603 subtracts the delayed signal from the electro-oculography original signal to output a saccade signal. It is possible to easily obtain a signed saccade signal by including the delayed signal generating unit 901.

The processing of the delayed signal generating unit 901 as shown in FIG. 31 will be described. The delayed signal generating unit 901 performs the following processing on an electro-oculography original signal f (x).

$$f\text{delay}(x) = f(x-t)$$

Figure 32:
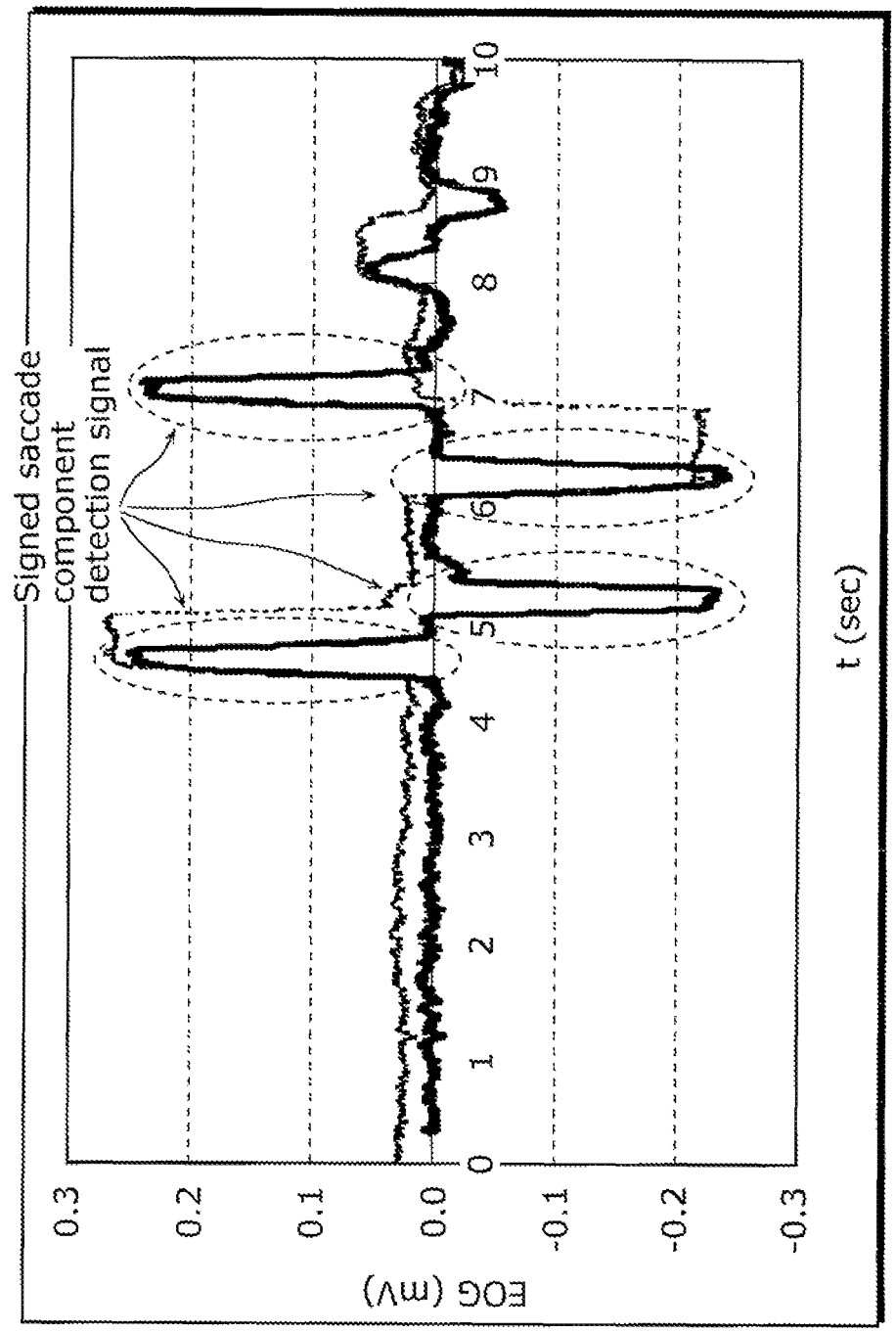
FIG. 32 is a diagram showing a saccade detection signal when a delay time of a delayed signal generating unit is 0.25 seconds.

Here, f delay (x) is an electro-oculography signal (delayed signal) after delay processing, and t is a delay time. The delayed signal can be obtained by performing the delay processing described above on the electro-oculography original signal shown in FIG. 19. Then, FIG. 32 shows an example where the delayed signal is subtracted from the electro-oculography original signal by the subtraction unit 603. It is to be noted that, in order to detect a signed saccade component from the electro-oculography original signal, the delay time is specified as t=0.25 seconds. It can be understood by referring to FIG. 32 that the signed saccade signal including the period of time when a saccade occurs is obtained.

The saccade detecting unit 900 generates a saccade detection signal and amplitude information on the basis of the output signal as shown in FIG. 32, and outputs the saccade detection signal and the amplitude information to the time interval calculating unit 212, the occurrence frequency calculating unit 312, the non-occurrence area specifying unit 412, or the non-occurrence probability calculating unit 512. For example, when the amount of change in sampling value within a period of time corresponding to a period of time required for a saccadic movement exceeds a predetermined threshold, it is determined that a saccadic movement has occurred and the saccade detection signal is output. Moreover, the amount of change in sampling value at this time is output as the amplitude information.

Figure 33:
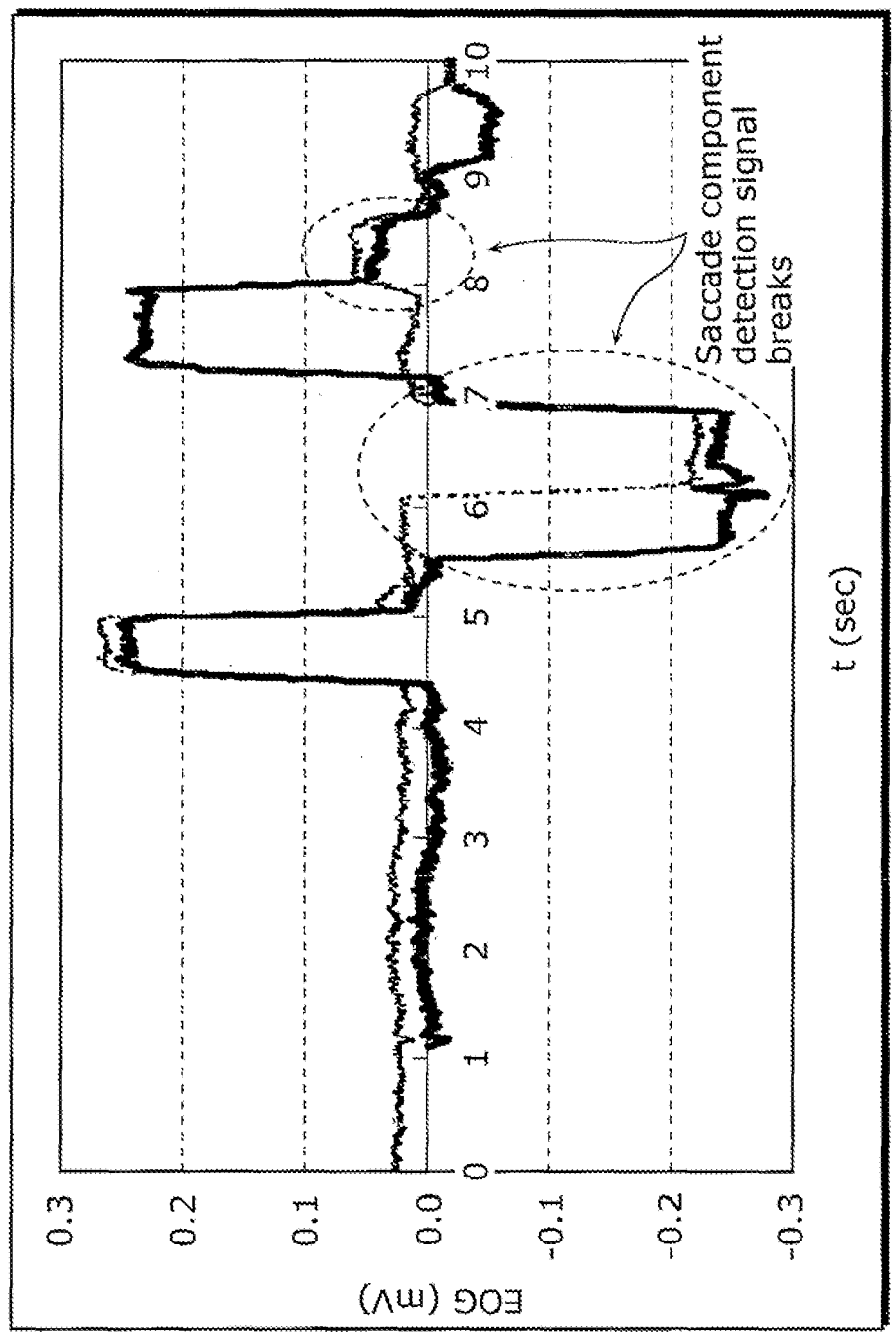
FIG. 33 is a diagram showing a saccade detection signal when the delay time of the delayed signal generating unit is 1.1 seconds.

Here, when the delay time t is set to be larger than the amount of time of one typical visual fixation (from 0.3 to 0.4 seconds, approximately), the saccade signal breaks as shown in FIG. 33. FIG. 33 is an example where the delay time t is 1.1 seconds. When the saccade signal breaks as shown in FIG. 33, the saccade signal cannot be extracted. Thus, the delay time t of the delayed signal generating unit 901 needs to be shorter than the amount of time of one typical visual fixation. It is to be noted that, although the delay time of 0.25 seconds is applied as an example in Embodiment 9, any value can be applied as long as the delay time is shorter than the amount of time of one typical visual fixation.

According to the structure of Embodiment 9 as described above, a signed saccade signal is detected by generating a delayed signal from an electro-oculography original signal and subtracting the delayed signal from the electro-oculography original signal. Thus, it is effective in that saccade signals can be distinguished between plus and minus.

(Embodiment 10)

Figure 34:
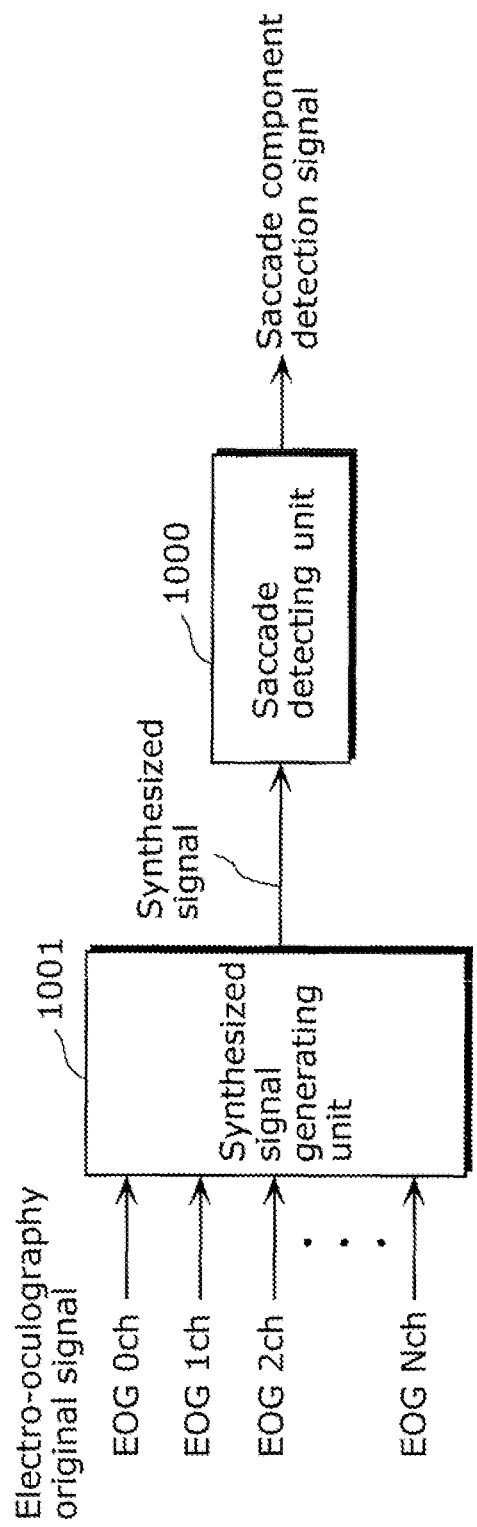
FIG. 34 is a block diagram of a saccade detecting unit according to Embodiment 10.

FIG. 34 is a block diagram of a saccade detecting device according to Embodiment 10. Embodiment 10 relates to a saccade detecting device when measuring an electro-oculography original signal in multichannel.

The saccade detecting device according to Embodiment 10 includes a synthesized signal generating unit 1001 that generates a synthesized signal from a multichannel electro-oculography original signal, and a saccade detecting unit 1000.

For example, the synthesized signal generating unit 1001 averages electro-oculography original signals EOG0ch to EOGNch measured through N channels 0ch to Nch, for each group to which the channels 0ch to Nch belong. The synthesized signal generating unit 1001 then subtracts the average values of the respective groups from each other and amplifies the difference, thereby generating a synthesized signal. FIG. 35 shows a detailed procedure.

First, the synthesized signal generating unit 1001 groups measurement channels having in-phase electro-oculogram (Step S10001). Whether or not electro-oculogram is in phase can be determined according to, for example, a measurement position such as the right or left of the face. It is to be noted that whether or not electro-oculogram is in phase may be not only determined from the measurement position, but also dynamically determined from a feature of a measured electro-oculography original signal. Following this, the synthesized signal generating unit 1001 calculates an average value of each group (Step S10002). The synthesized signal generating unit 1001 then subtracts the average values of the respective groups from each other and amplifies the difference (Step S10003), and outputs the result as a synthesized signal (Step S10004).

The saccade detecting unit 1000 generates a saccade detection signal using the synthesized signal generated by the synthesized signal generating unit 1001. For instance, the saccade detecting device according to any of Embodiments 6 to 9 may be applied to the saccade detecting unit 1000.

The saccade detecting unit 1000 generates a saccade detection signal and amplitude information, and outputs the saccade detection signal and the amplitude information to the time interval calculating unit 212, the occurrence frequency calculating unit 312, the non-occurrence area specifying unit 412, or the non-occurrence probability calculating unit 512. For example, when the amount of change in sampling value within a period of time corresponding to a period of time required for a saccadic movement exceeds a predetermined threshold, it is determined that a saccadic movement has occurred and the saccade detection signal is output. Moreover, the amount of change in sampling value at this time is output as the amplitude information.

According to the structure of Embodiment 10 as described above, a synthesized signal of a high S/N ratio is generated from a multichannel electro-oculography original signal, and a saccade signal is detected using the synthesized signal. This is effective in improving saccade detection accuracy.

Next, a method of measuring an electro-oculogram in consideration of an effect of a blink will be described. When detecting an eye movement by utilizing a change in electro-oculogram as in the EOG and the like, there is a problem of an effect of a signal generated by a blink of a user (hereinafter referred to as "blink signal").

In some cases, the blink signal is generated invariably in the plus direction, or invariably in the minus direction, depending on the method for measuring the electro-oculogram. FIGS. 36A to 36D show examples of placement patterns of the electro-oculography measuring unit and the method for measuring the electro-oculography original signal.

According to the placement pattern of FIG. 36A, the electrodes A and B are placed above and below an eye, respectively, and a difference potential Va−Vb is obtained, where Va is the electro-oculogram measured by the electrode A placed above the eye and Vb is the electro-oculogram measured by the electrode B placed below the eye. In this case, the blink signal is generated invariably in the plus direction. This is because, when a human blinks, the eyeball is always moves upward.

Figure 36A:
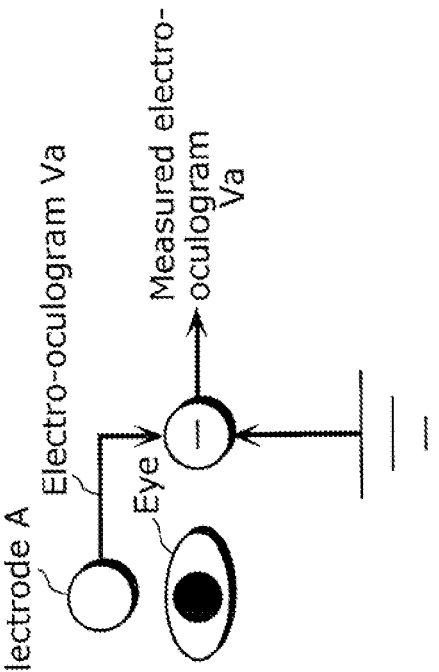
FIG. 36A is a diagram showing an example of an electrode placement pattern.
Figure 36C:
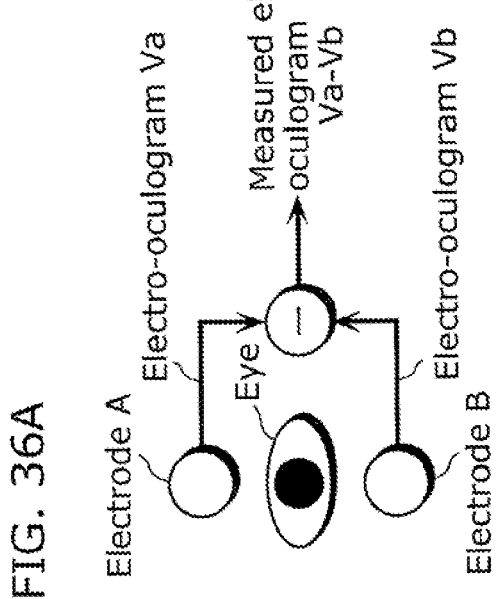
FIG. 36C is a diagram showing another example of the electrode placement pattern.
Figure 36B:
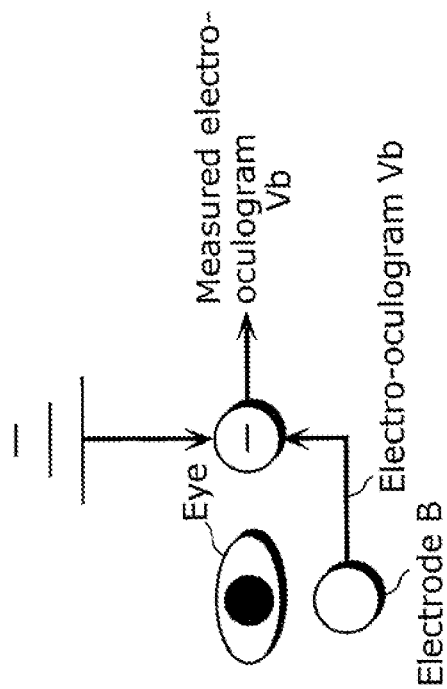
FIG. 36B is a diagram showing another example of the electrode placement pattern.

According to the placement pattern of FIG. 36B, the electrode A is placed above the eye and the other electrode is placed on the earth or a place less subject to the electro-oculogram, so that the electro-oculogram Va of the electrode A is measured. In this case also, the blink signal is generated invariably in the plus direction (at a value larger than a reference value).

Likewise, according to the placement pattern of FIG. 36C, the electrodes A and B are placed above and below the eye, respectively, and a difference potential Vb−Va is obtained, where Vb is the electro-oculogram measured by the electrode B placed below the eye and Va is the electro-oculogram measured by the electrode A placed above the eye. In this case, the blink signal is generated invariably in the minus direction. According to the placement pattern of FIG. 36D, the electrode B is placed below the eye and the other electrode is placed on the earth or a place less subject to the electro-oculogram, so that the electro-oculogram Vb of the electrode B is measured. In this case also; the blink signal is generated invariably in the minus direction.

Figure 37:
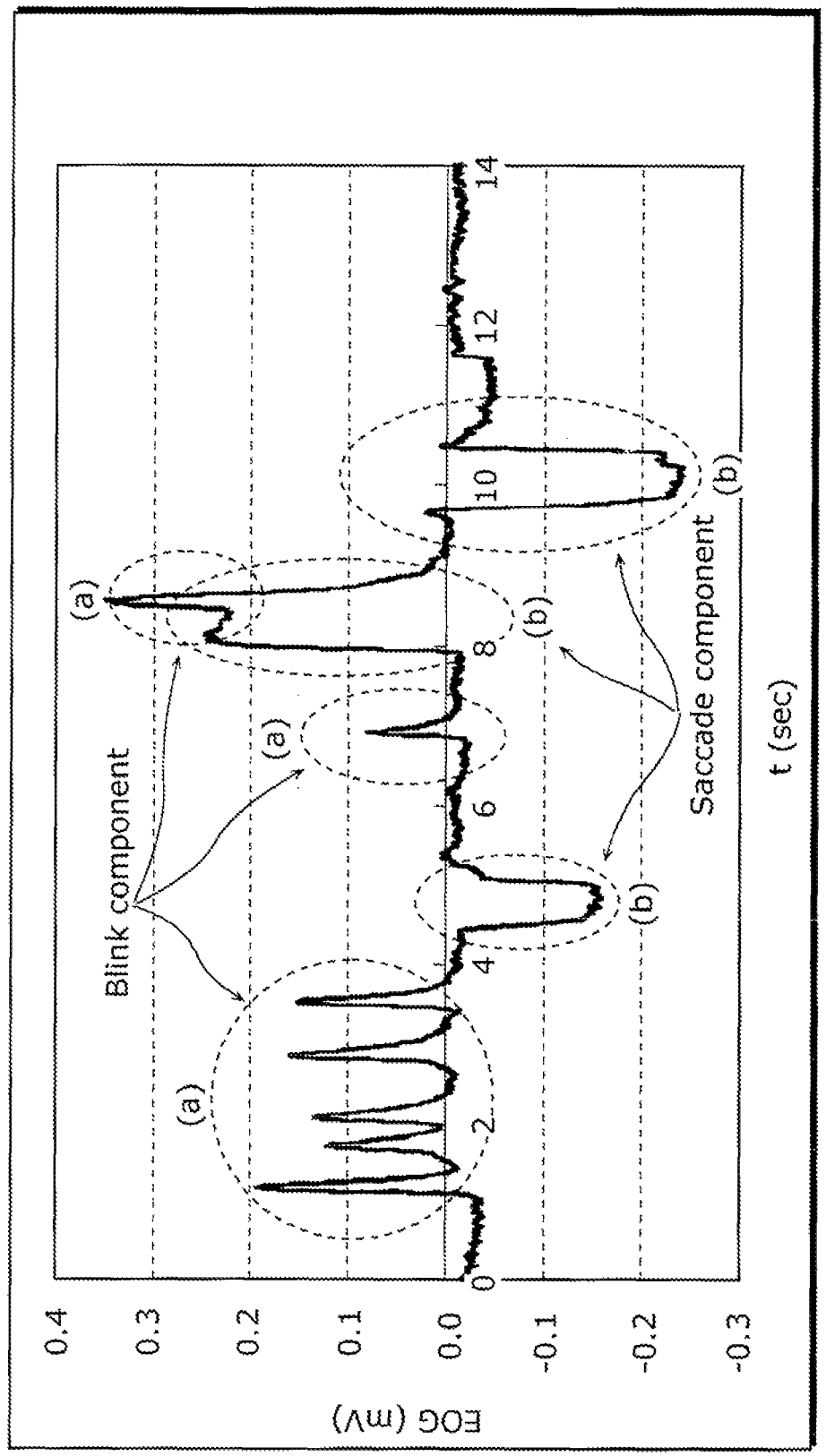
FIG. 37 is a diagram showing an example of an electro-oculography signal that includes a blink signal.

When the user blinks during the measurement according to the placement patterns as shown in FIGS. 36A and 36B, a potential is generated steeply in the plus direction (this is the "blink signal") as shown by regions (a) in FIG. 37. When the blink signal is directly used for detecting a gaze point, the gaze point changes rapidly and a gaze-path cannot be tracked accurately.

Here, there is a technique disclosed by Japanese Unexamined Patent Application Publication No. 11-85384 (Patent Literature 1) as a method to reduce the effect of the blink signal (a component of a signal generated by a blink) and the like from the electro-oculography original signal.

The technique disclosed by Patent Literature 1 aims to detect an electro-oculogram of a user and input a gaze-position (cursor) in real time. At this time, a delay element is introduced into a fluctuation waveform of the electro-oculogram, so that a temporal change in the gaze-position (cursor) is smoothed and a rapid change in the gaze-position caused by a blink is reduced.

Further, there is a technique disclosed by "Full-time Wearable Headphone-Type Gaze Detector", Interaction, 2006, pp. 23-24, 2006 (Non-patent Literature 1), Hiroyuki Manabe, Masaaki Fukumoto, as a technique for reducing the effect of the blink signal.

According to the technique disclosed in Non-patent Literature 1, a total of 8 electrodes are placed on the right and left of a headphone. A median filter is applied at 0.4 second intervals as to changes in the electro-oculogram obtained from the 8 electrodes, thereby removing a change caused by a blink signal that is shorter than the above-described time interval.

However, as shown in Patent Literature 1, merely temporally smoothing the electro-oculography original signal causes an adverse effect that the smoothing is performed even on a saccade waveform indicating a component change in a saccade (a rapid movement of a human eye from one gaze point to another gaze point (saccadic movement)) that is important in tracking a gaze-path.

Figure 38:
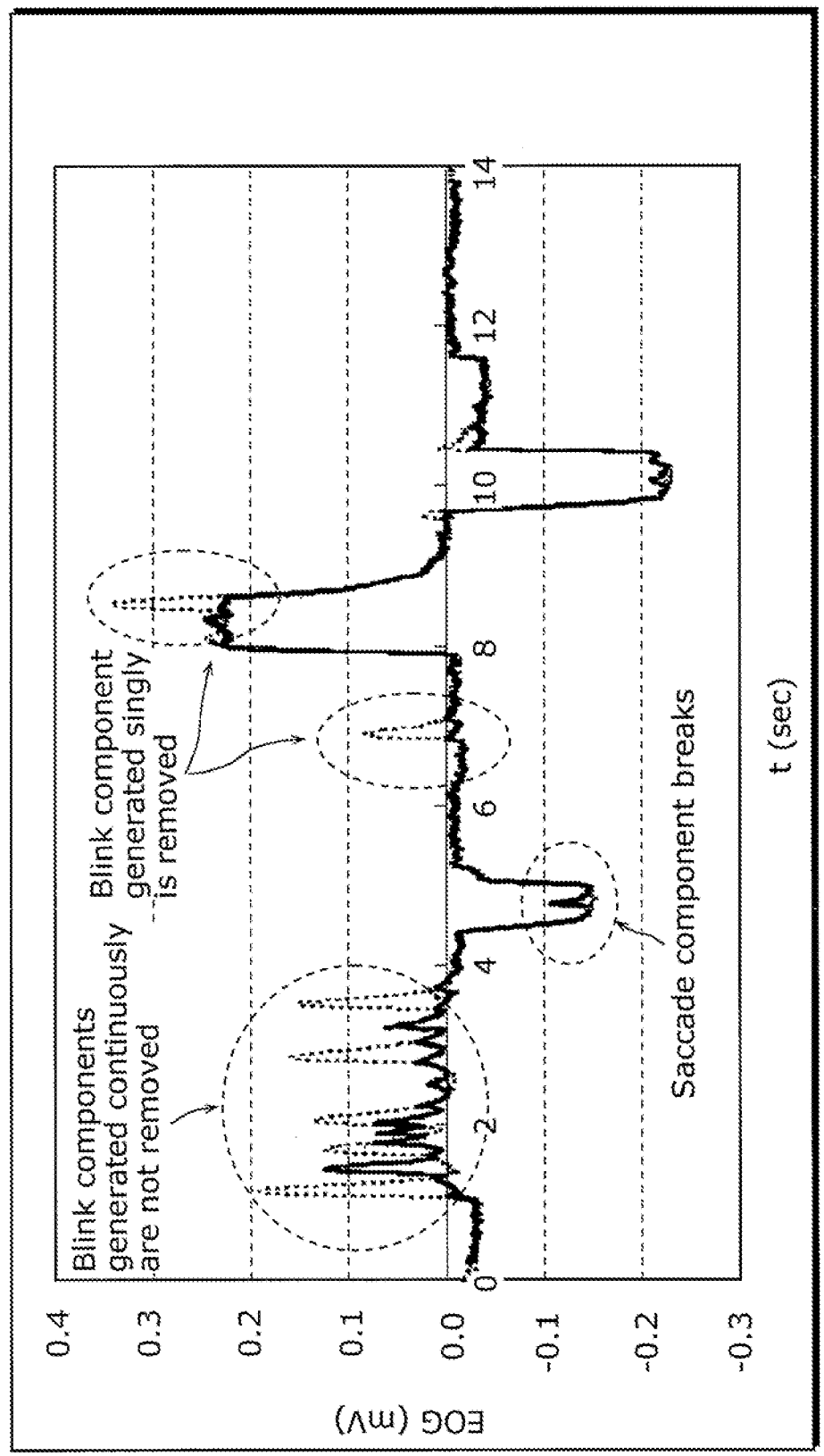
FIG. 38 is a diagram showing an electro-oculography signal obtained by applying median filter processing to the electro-oculography signal shown in FIG. 37.

In addition, when a median filter is applied to the electro-oculography original signal as shown in Non-patent Literature 1, although a blink signal that has been generated singly can be removed as shown in FIG. 38, the effect of blink signals that have been generated continuously for at least a predetermined amount of time cannot be completely removed. In addition, an adverse effect that a part of the saccade waveform breaks is caused.

Therefore, the above-described literatures have not made it clear what smoothing filter should be applied how long and in what order is optimum, in consideration of removal of the blink signal and retaining the saccade signal.

Thus, in Embodiments 11 to 13, a method for removing or detecting a blink signal from an electro-oculography signal of a user with ease and high accuracy, and further detecting a saccade signal will be described. Though the following describes an example of removing or detecting a blink signal from an electro-oculography original signal including a drift signal obtained from the electrodes placed on the user, the same applies to the case of removing or detecting a blink signal from an electro-oculography signal from which noise has been removed.

(Embodiment 11)

Figure 39:
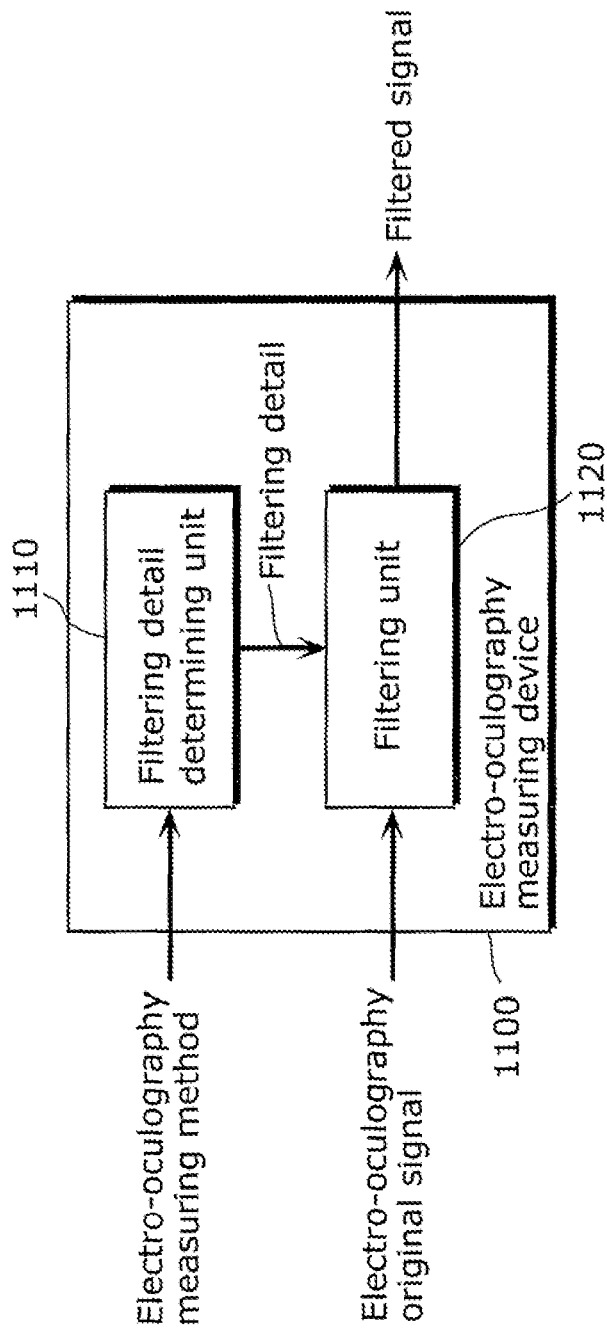
FIG. 39 is a block diagram of an electro-oculography measuring device according to Embodiment 11.

FIG. 39 is a block diagram showing a structure of an electro-oculography measuring device 1100 according to Embodiment 11 of the present invention.

The electro-oculography measuring device 1100 includes: an electro-oculography measuring unit (not shown) placed around a user's eye to measure an electro-oculogram and output an electro-oculography original signal; a filtering detail determining unit 1110 that determines a detail of filtering using a signal indicating how to measure the electro-oculogram (in the diagram: electro-oculography measuring method); and a filtering unit 1120 that performs filtering on the electro-oculography original signal according to a filtering detail signal output from the filtering detail determining unit 1110.

First, the method of measuring the electro-oculogram may be specified in advance by an experimenter or a user, or may be estimated based on a tendency of change in the electro-oculography original signal.

More specifically, the user may specify a measuring method as the one that places the electrodes A and B on the right and left, respectively, of an eyeball as shown in FIGS. 63A and 63B, or when a signal is generated upward in the electro-oculography original signal whenever the user blinks, it may be estimated that the placement pattern as shown in FIGS. 36A and 36B is employed for the measuring method.

Figure 40:
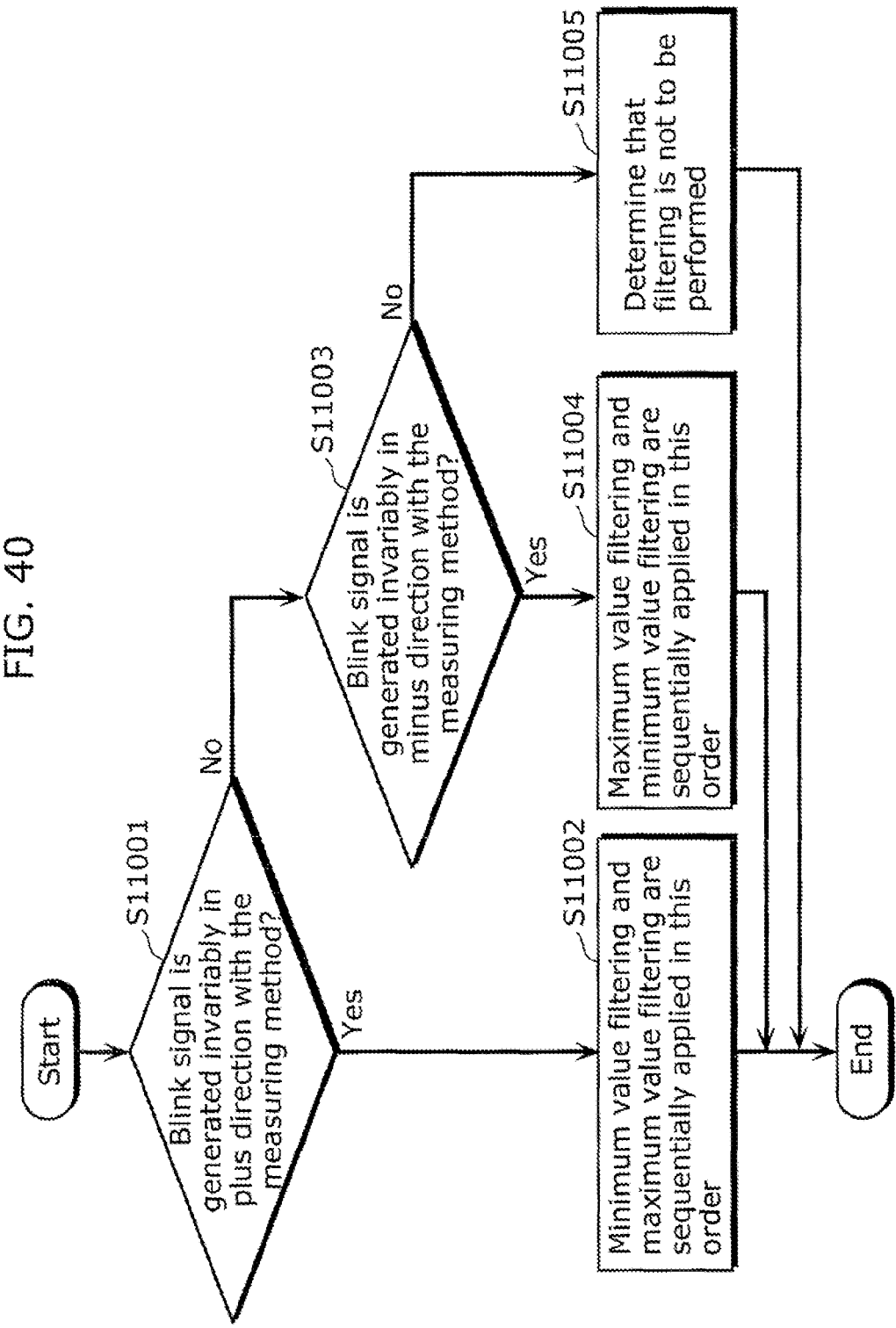
FIG. 40 is a flowchart showing an operation of a filtering detail determining unit according to Embodiment 11.

FIG. 40 is a flowchart showing a filtering detail determining operation of the filtering detail determining unit 1110. The filtering detail determining unit 1110 determines an order of applying a filter (described later) in the filtering unit 1120 to first remove an effect of a blink. Further, although not shown, the number of necessary taps (time) is determined depending on the difference of electro-oculography measuring methods. Furthermore, whether or not a filter is to be applied is changed depending on whether the electrodes placed in advance are arranged in a horizontal direction or in a vertical direction.

More specifically, it is determined whether or not a blink signal is generated invariably in the plus direction with the measuring method as in the placement pattern of FIGS. 36A and 36B (Step S11001). When the blink signal indicates invariably a plus potential (Yes in Step S11001), the filtering detail is determined so that the minimum value filtering and the maximum value filtering are performed in this order (Step S11002).

Figure 36D:
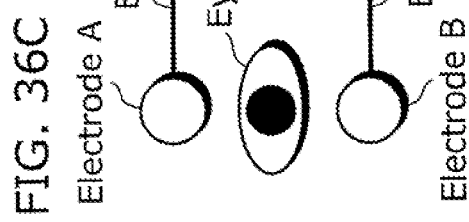
FIG. 36D is a diagram showing another example of the electrode placement pattern.

When the blink signal does not indicate a plus potential (No in Step S11001), it is determined whether or not the blink signal is generated invariably in the minus direction with the measuring method as in the placement pattern of FIGS. 36C and 36D (Step S11003). When the blink signal indicates invariably a minus potential (Yes in Step S11003), the filtering detail is determined so that the maximum value filtering and the minimum value filtering are performed in this order (Step S11004).

When the blink signal does not indicate a minus potential (No in Step S11003), it is determined that the measuring method is not affected by a blink, and that filtering is not to be performed for removing a blink signal (Step S11005). It is to be noted that an example of the case where the measuring method is not affected by a blink includes: the case where the electrodes A and B are placed on the right and left of an eye as shown in FIGS. 63A and 63B to measure the difference; and the case where the electrodes A and B are placed away from an eye.

The filtering detail determining unit 1110 outputs a filtering detail signal (orientation, the number of taps n, presence or absence (n=0 may also be output)) by including information such as an application order of the filter which has been determined in the above process, the number of taps n of the filter, and unit processing period. It is to be noted that the determination order of the above-described flowchart is an example, and any determination order may be employed.

Figure 41:
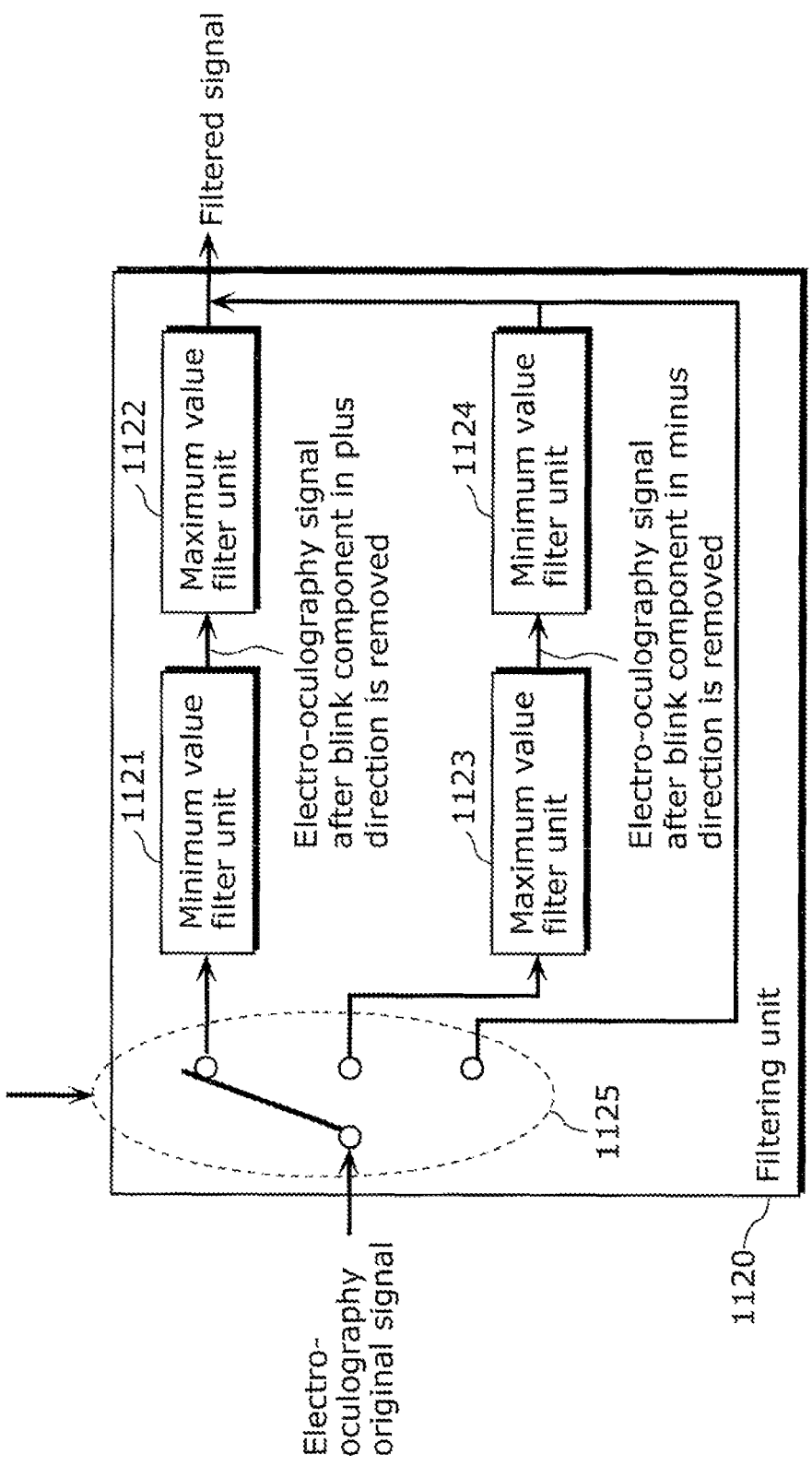
FIG. 41 is a block diagram of a filtering unit shown in FIG. 39.

FIG. 41 is a diagram showing a structure of the filtering unit 1120. The filtering unit 1120 performs filtering on the electro-oculography original signal according to the filtering detail signal that has been output from the filtering detail determining unit 1110.

The filtering unit 1120 includes: two minimum value filter units 1121 and 1124; two maximum value filter units 1122 and 1123; and a switch 1125 that switches between a first path to a third path from an input terminal to an output terminal to connect one of the paths to which the electro-oculography original signal is output.

In the first path, the minimum value filter unit 1121 (first filtering unit) and the maximum value filter unit 1122 (second filtering unit) are connected in series, where the minimum value filter unit 1121 performs the minimum value filtering on the electro-oculography original signal and outputs a first electro-oculography signal, and the maximum value filter unit 1122 performs the maximum value filtering on the first electro-oculography signal and outputs a second electro-oculography signal (filtered signal). In the second path, the maximum value filter unit 1123 (first filtering unit) and the minimum value filter unit 1124 (second filtering unit) are connected in series, where the maximum value filter unit 1123 performs the maximum value filtering on the electro-oculography original signal and outputs a first electro-oculography signal, and the minimum value filter unit 1124 performs the minimum value filtering on the first electro-oculography signal and outputs a second electro-oculography signal (filtered signal). The third path is a path that outputs the electro-oculography original signal without performing filtering processing. The switch 1125 switches between output destinations to which the electro-oculography original signal is output, according to the filtering detail determined by the filtering detail determining unit 1110.

In the case where the switch 1125 receives the filtering detail signal generated in Step S11002 shown in FIG. 40, the switch 1125 switches a connection point to the one in the top stage shown in FIG. 41, so that the electro-oculography original signal is output to the first path. In the case where the switch 1125 receives a filtering detail signal generated in Step S11004 shown in FIG. 40, the switch 1125 switches the connection point to the one in the middle stage shown in FIG. 41, so that the electro-oculography original signal is output to the second path. In the case where the switch 1125 receives a filtering detail signal generated in Step S11005 shown in FIG. 40, the switch 1125 switches the connection point to the one in the bottom stage shown in FIG. 41, so that the electro-oculography original signal is output to the third path.

It is to be noted that the processing details of the minimum value filter units 1121 and 1124, and the maximum value filter units 1122 and the 1123 are the same as those described in Embodiment 6, and so their description is omitted. It is to be noted that, although two units are included in each of the minimum value filter unit and the maximum value filter unit in Embodiment 11, that is, the minimum value filter units 1121 and 1124 and the maximum value filter units 1122 and 1123, it is also possible to provide a single unit for each of the minimum value filter unit and the maximum value filter unit and change an order of connection based on the filtering detail signal, and the like, to achieve the invention.

Next, the processing in the case where the electro-oculography original signal is input into the first path will be described. First, FIG. 42 is a diagram showing the first electro-oculography signal obtained by performing, on the electro-oculography original signal as shown in FIG. 37, the minimum value filtering in the minimum value filter unit 1121.

It is to be noted that, in order to remove the blink signal from the electro-oculography original signal, the unit processing period of the minimum value filter unit 1121 is set to 0.25 seconds in accordance with the value determined with a filtering detail signal.

Figure 42:
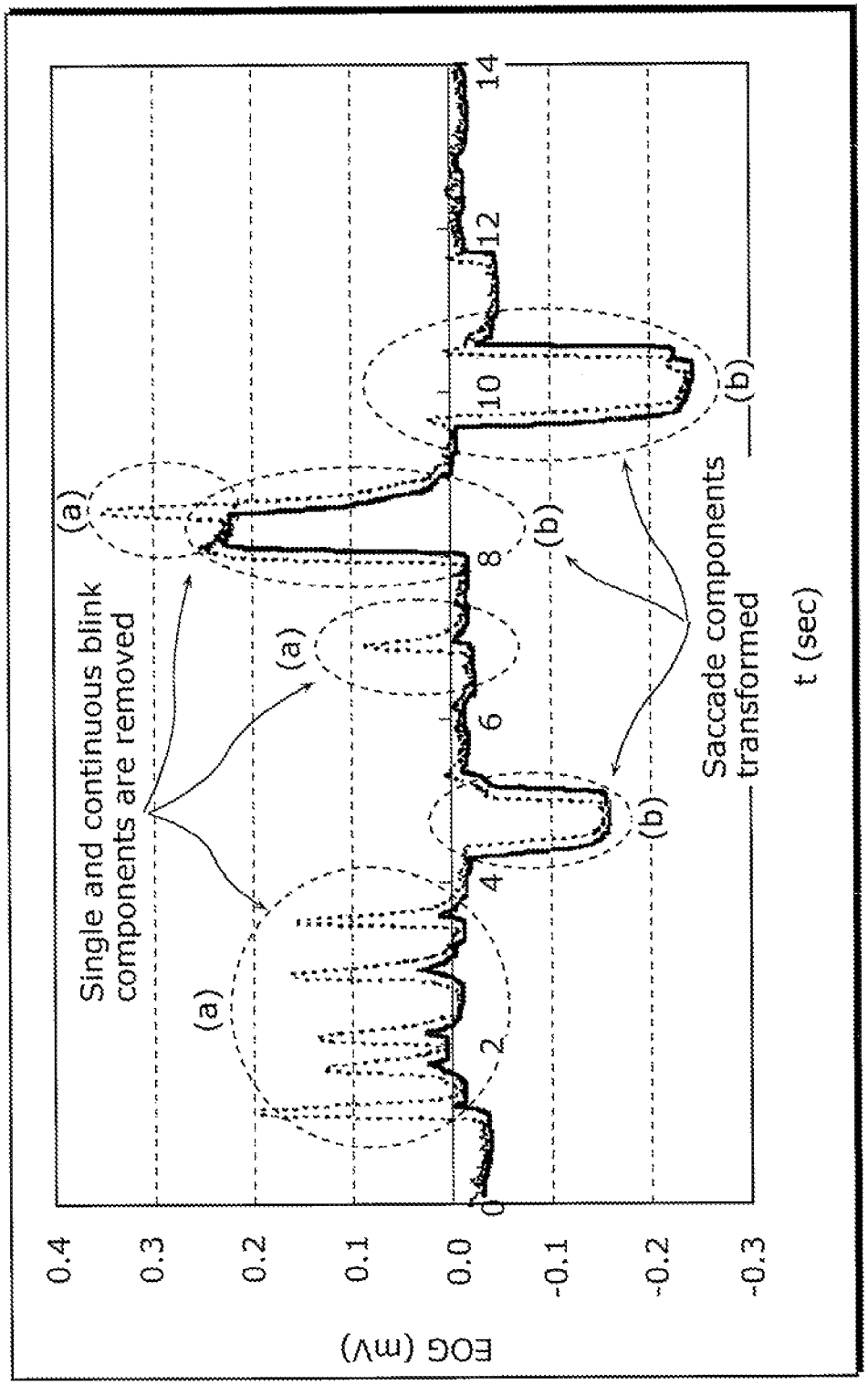
FIG. 42 is a diagram showing an electro-oculography signal obtained by applying minimum value filtering to the electro-oculography signal shown in FIG. 37.

It can be understood by referring to regions (a) in FIG. 42 that consecutive blink signals and an isolated blink signal are removed by performing the minimum value filtering on the electro-oculography original signal. However, in the first electro-oculography signal as shown in FIG. 42, the saccade waveforms have transformed (increased in a temporal width), which is an adverse effect caused by performing the minimum value filtering.

It is to be noted that, although Embodiment 11 describes an example where the minimum value filtering is performed by setting the unit processing period of the minimum value filter unit 1121 to 0.25 seconds, it may be any value as long as it is longer than an amount of time of one typical blink (from 0.15 seconds to 0.2 seconds, approximately) and shorter than an amount of time of one visual fixation (from 0.3 seconds to 0.4 seconds, approximately).

Figure 43:
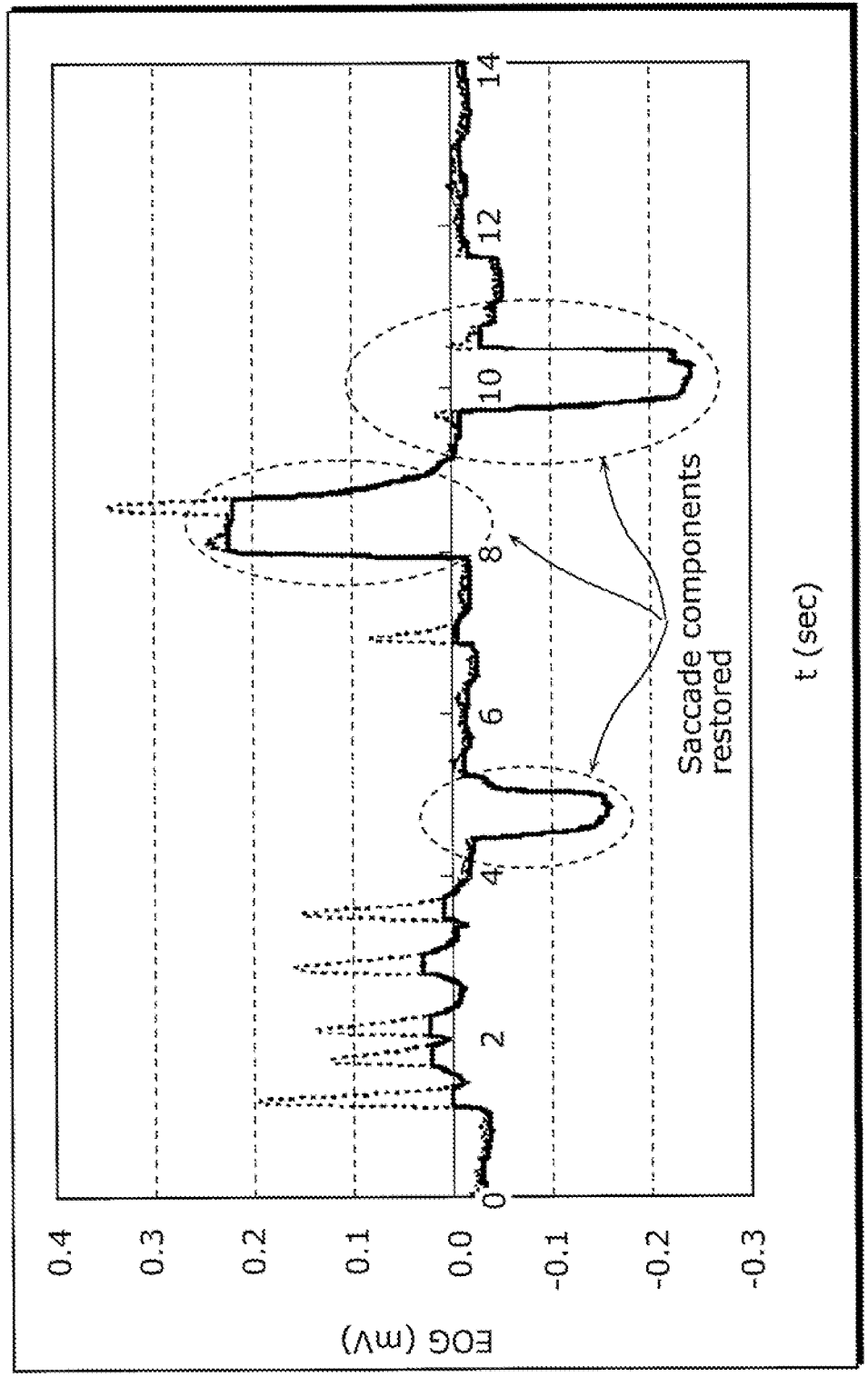
FIG. 43 is a diagram showing an electro-oculography signal obtained by applying maximum value filtering to the electro-oculography signal shown in FIG. 42.

Next, FIG. 43 is a diagram showing the second electro-oculography signal (filtered signal) obtained by performing the maximum value filtering on the first electro-oculography signal as shown in FIG. 42, in the maximum value filter unit 1122. It is to be noted that the unit processing period is set to 0.25 seconds as in the case of the minimum value filter unit 1121.

As shown in FIG. 43, the transformed saccade waveform as in FIG. 42 can be restored to the width of the original signal waveform by performing the maximum value filtering on the first electro-oculography signal.

Fundamental processes of the maximum value filter unit 1123 and the minimum value filter unit 1124 are the same as the maximum value filter unit 1122 and the minimum value filter unit 1121, respectively, and it is possible to remove the blink signal in the minus direction without affecting the saccade waveform, by performing filtering in order of the maximum value filtering and the minimum value filtering.

It is to be noted that, although the minimum value filter units 1121 and 1124, and the maximum value filter units 1122 and 1123 are used in the example of Embodiment 11, a filter that selects a value close to the minimum value or the maximum value may be used. In this case, it is desirable to select a value approximately 90% of the maximum value or the minimum value.

Further, although the same value is used for the number of filter taps of the minimum value filtering and the maximum value filtering in Embodiment 11, a proximate value may be used. In other words, perfect matching is not necessarily required.

In the case where plural filtering processes are performed consecutively, it is sufficient to perform the filtering for removing the effect of the blink signal first, and then perform the filtering for restoring the temporal waveform of saccade.

Further, although the blink signal is removed and the saccade waveform is restored by consecutively performing the minimum value filtering and the maximum value filtering in Embodiment 11, only one of the minimum value filtering and the maximum value filtering may be performed without departing from the scope of the present invention when the purpose is only to remove the blink signal.

According to the structure of the above-described Embodiment 11, the detail of filtering to be performed on an electro-oculography original signal is determined according to the method of measuring the electro-oculography original signal, and filtering is performed according to the detail. As a result, it is possible to remove a blink signal properly, even when the electrodes are placed in the opposite orientation, for example.

Further, when the measuring method is such that a blink signal is generated in the plus direction of an electro-oculography original signal, the filtering detail is determined such that the minimum value filtering and the maximum value filtering are performed consecutively in this order. As a result, it is possible to easily remove a blink signal in the plus direction and restore a saccade waveform.

Further, when the measuring method is such that a blink signal is generated in the minus direction of an electro-oculography original signal, the filtering detail is determined such that the maximum value filtering and the minimum value filtering are performed consecutively in this order. As a result, it is possible to easily remove a blink signal in the minus direction and restore a saccade waveform.

The electro-oculography measuring device 1100 having the above-described structure can be applied to the noise reduction device 100 shown in FIG. 1. For example, a filtering processing signal that is output from the electro-oculography measuring device 1100 is input to the saccade information obtaining unit 110 and the filtering unit 130 shown in FIG. 1 as an electro-oculography original signal. This eliminates the need to take a blink signal into consideration in the saccade information obtaining unit 110 and the filtering unit 130, even when an electro-oculography signal including a blink signal is measured in the electro-oculography measuring unit.

(Embodiment 12)

Figure 44:
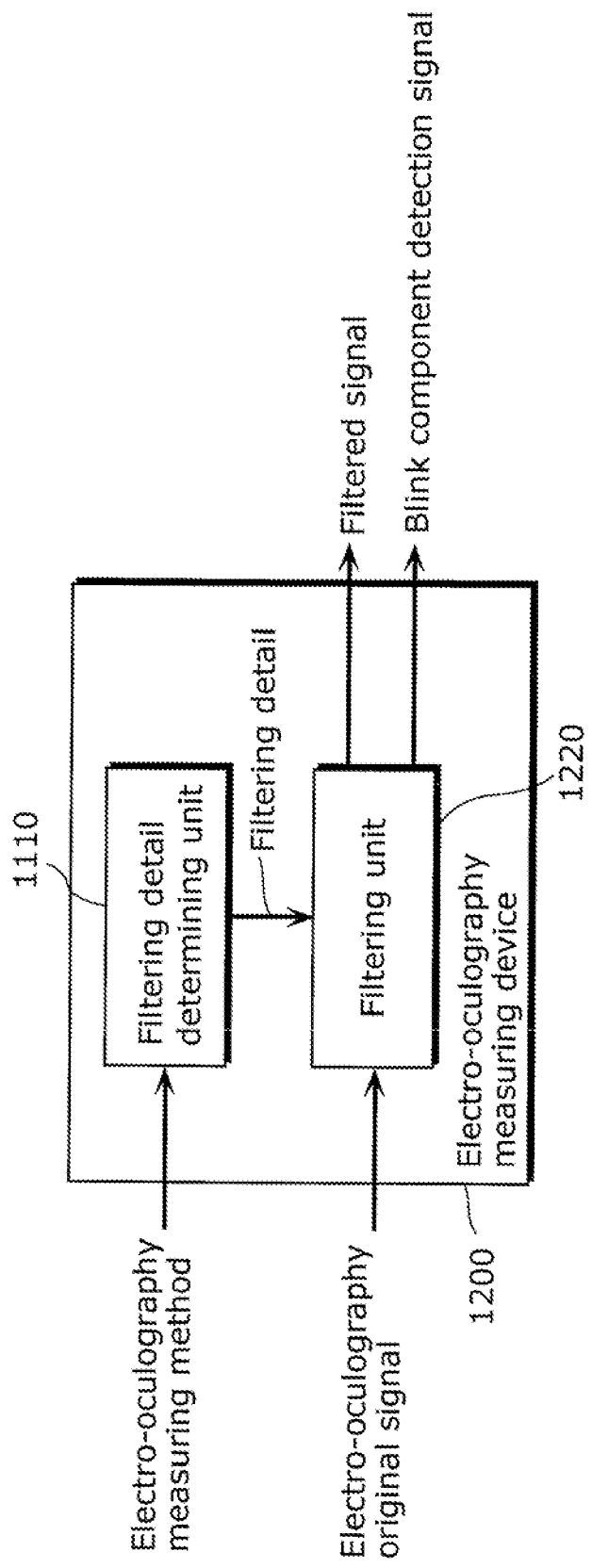
FIG. 44 is a block diagram of an electro-oculography measuring device according to Embodiment 12.
Figure 45:
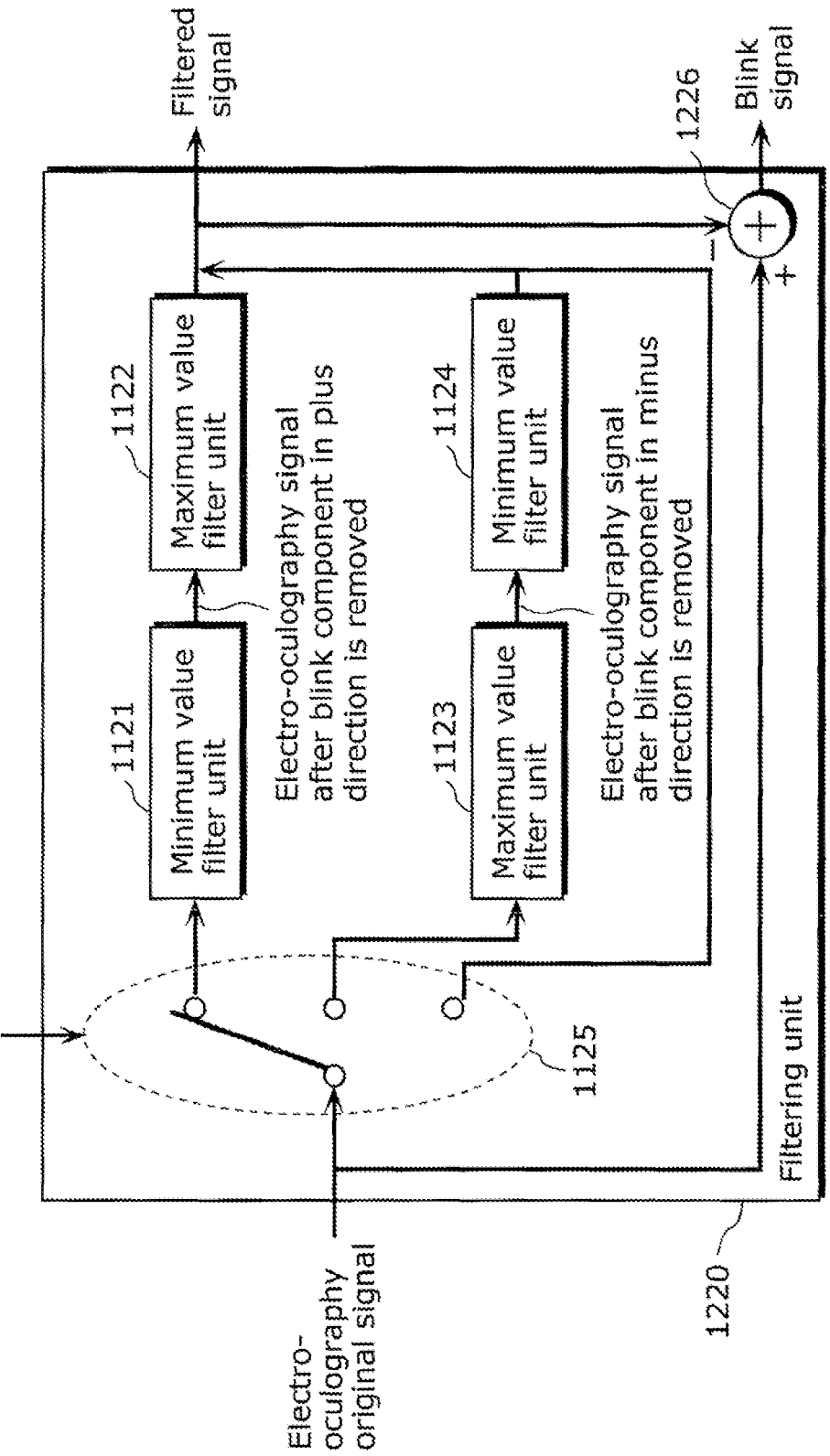
FIG. 45 is a block diagram of a filtering unit shown in FIG. 44.

FIGS. 44 and 45 are block diagrams showing a structure of an electro-oculography measuring device 1200 according to Embodiment 12 of the present invention.

Embodiment 12 differs from Embodiment 11 in that a filtering unit 1220 includes a subtraction unit 1226 that subtracts a filtered electro-oculography signal from the electro-oculography original signal. The inclusion of the subtraction unit 1226 makes it possible to output a blink signal in addition to the filtered signal.

FIG. 45 is a block diagram showing an example of the filtering unit 1220 in the electro-oculography measuring device 1200 according to Embodiment 12. It is to be noted that, since the structure same as the structure in FIG. 41 has already been described, the same numerals are assigned and the description that is overlapped will be omitted.

The subtraction unit 1226 outputs a difference between the electro-oculography original signal and the filtered signal. The difference is a blink signal.

Figure 46:
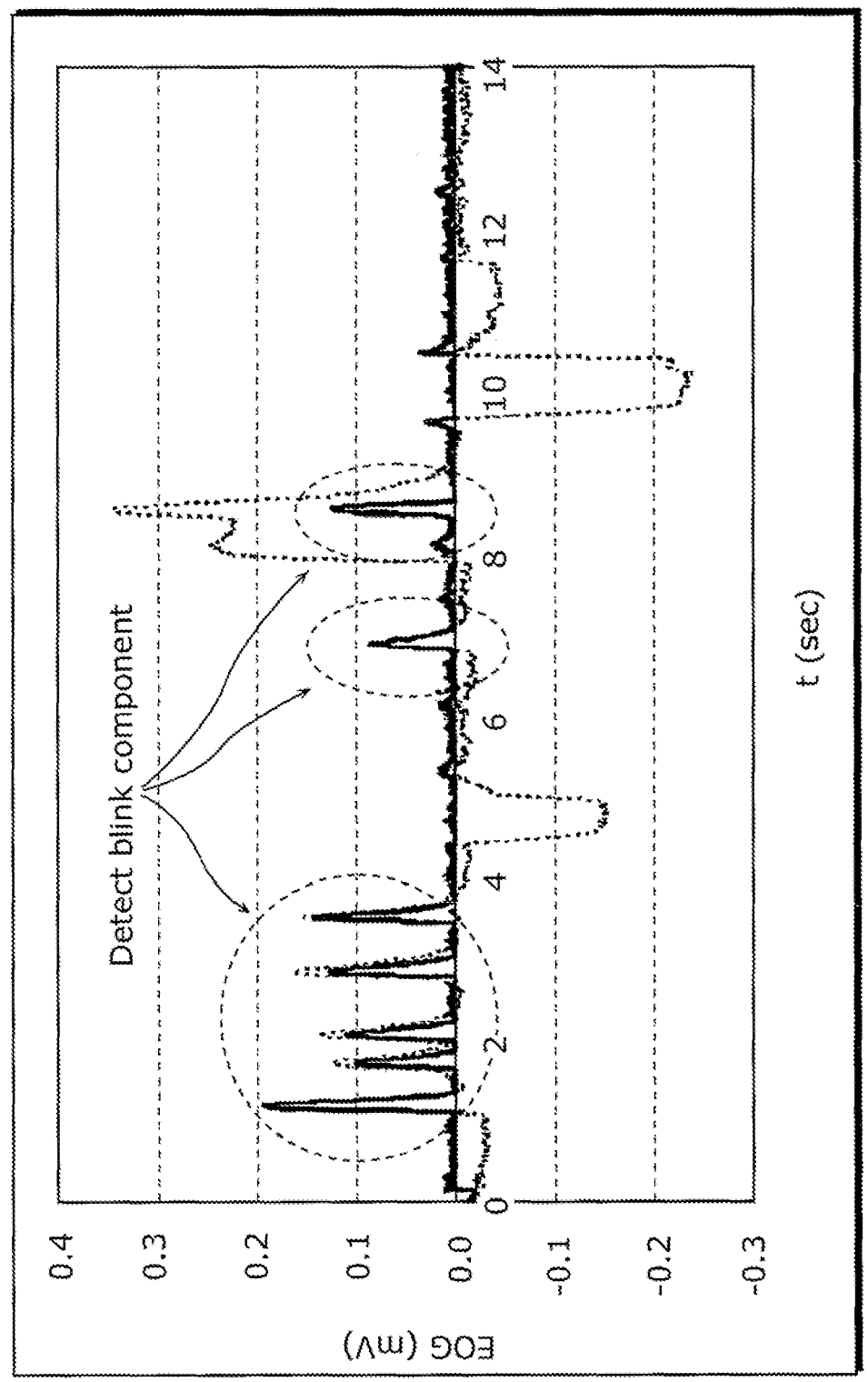
FIG. 46 is a diagram showing a blink signal obtained by inputting the electro-oculography signal shown in FIG. 37 into the filtering unit shown in FIG. 45.

FIG. 46 shows a blink signal obtained by subtracting the second electro-oculography signal in FIG. 43 from the electro-oculography original signal in FIG. 37. It is understood, by referring to FIG. 46, that only the blink signal is detected from the electro-oculography original signal.

According to the structure of the above-described Embodiment 12, the detail of filtering to be performed on an electro-oculography original signal is determined according to the method of measuring the electro-oculography original signal, and suitable filtering is performed according to the detail. As a result, it is possible to detect a blink signal no matter what measuring method is employed.

Further, when the measuring method is such that a blink signal is generated in the plus direction of an electro-oculography original signal, the filtering detail is determined such that the minimum value filtering and the maximum value filtering are performed consecutively in this order. As a result, it is possible to restore a saccade component while easily detecting the blink signal in the plus direction.

Further, when the measuring method is such that a blink signal is generated in the minus direction of an electro-oculography original signal, the filtering detail is determined such that the maximum value filtering and the minimum value filtering are performed consecutively in this order. As a result, it is possible to restore a saccade component while easily detecting the blink signal in the minus direction.

(Embodiment 13)

Figure 47:
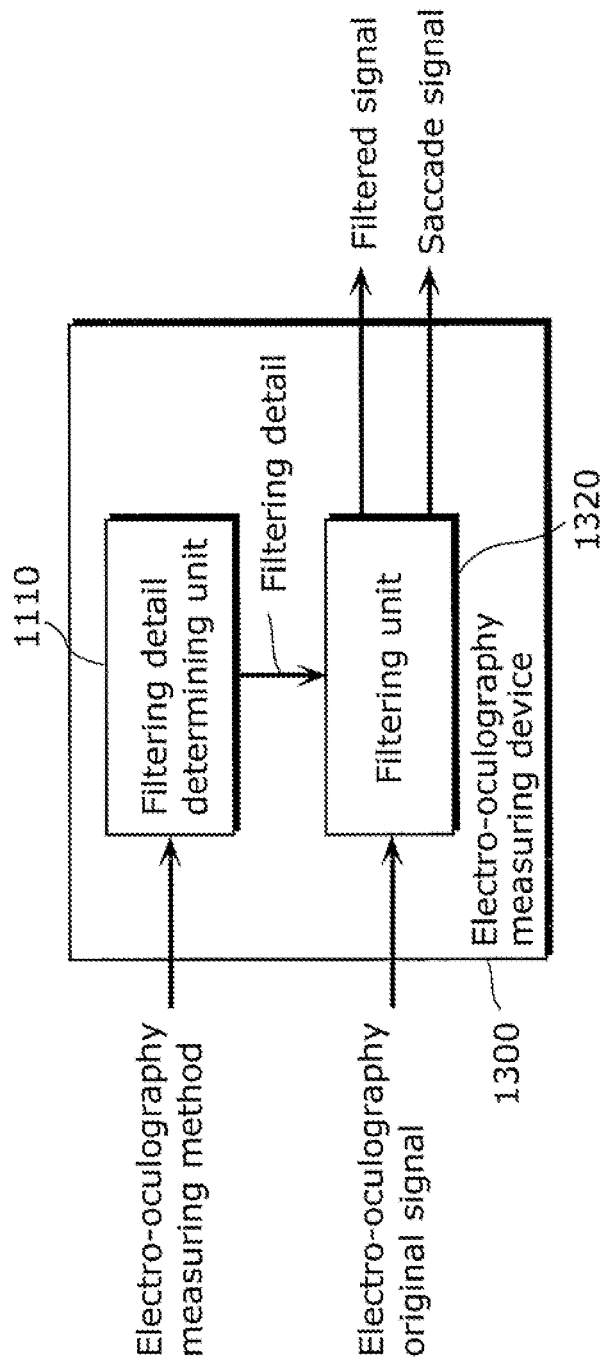
FIG. 47 is a block diagram of an electro-oculography measuring device according to Embodiment 13.
Figure 48:
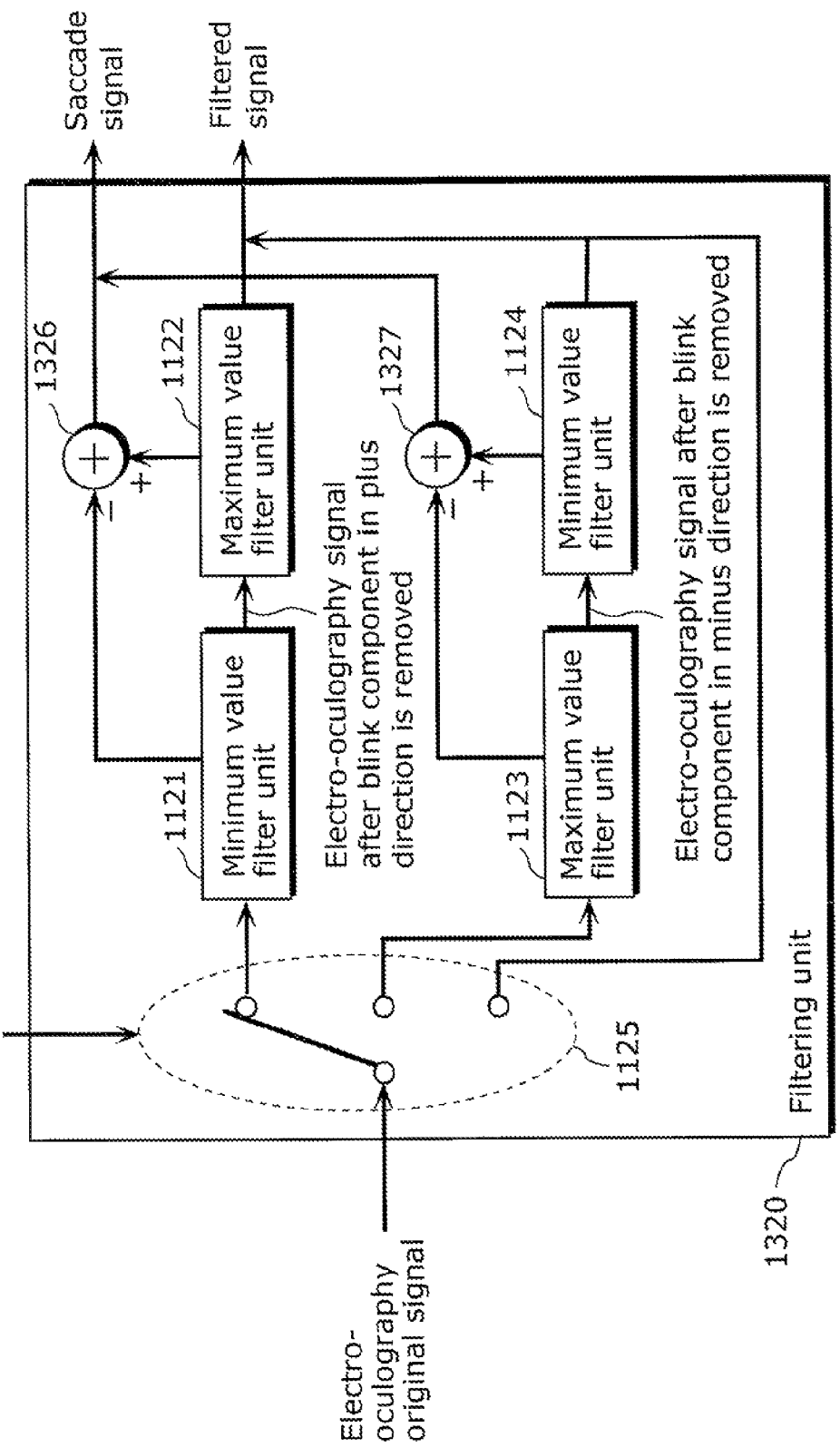
FIG. 48 is a block diagram of a filtering unit shown in FIG. 47.

FIGS. 47 and 48 are block diagrams showing a structure of an electro-oculography measuring device 1300 according to Embodiment 13 of the present invention.

Embodiment 13 differs from Embodiment 11 in that a filtering unit 1320 includes subtraction units 1326 and 1327 which subtract a signal on which one of the maximum value filtering and the minimum value filtering has been performed (first electro-oculography signal) from a signal on which both of the maximum value filtering and the minimum value filtering have been performed (second electro-oculography signal). The inclusion of the subtraction units 1326 and 1327 makes it possible to output a saccade signal in addition to the filtered signal.

FIG. 48 is a block diagram showing an example of the filtering unit 1320 in the electro-oculography measuring device 1300 according to Embodiment 13. It is to be noted that, since the structure same as the structure in FIG. 41 has already been described, the same numerals are assigned and the description that is overlapped will be omitted.

The subtraction unit 1326 outputs a saccade signal by subtracting an output signal of the minimum value filter unit 1121 from an output signal of the maximum value filter unit 1122. Similarly, the subtraction unit 1327 outputs a saccade signal by subtracting an output signal of the maximum value filter unit 1123 from an output signal of the minimum value filter unit 1124.

Figure 49:
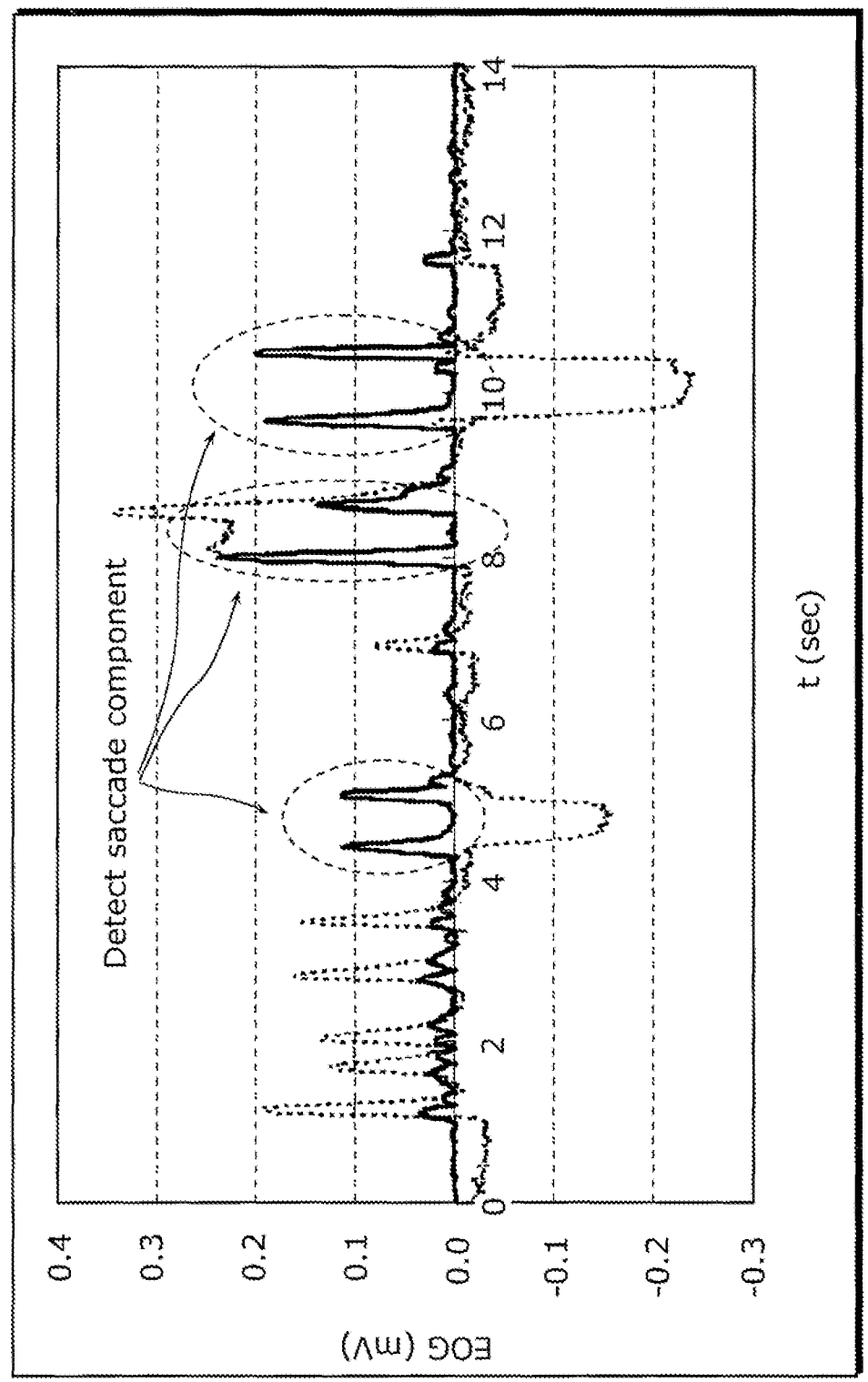
FIG. 49 is a diagram showing a saccade signal obtained by inputting the electro-oculography signal shown in FIG. 37 into the filtering unit shown in FIG. 48.

FIG. 49 shows a saccade signal obtained by subtracting the first electro-oculography signal in FIG. 42, on which the minimum value filtering has been performed, from the second electro-oculography signal in FIG. 43, on which the maximum value filtering has been performed. It is understood, by referring to FIG. 49, that only the saccade signal is detected from the electro-oculography original signal.

According to the structure of the above-described Embodiment 13, the detail of filtering to be performed on an electro-oculography original signal is determined according to the method of measuring the electro-oculography original signal, and filtering is performed according to the detail. As a result, it is possible to detect a saccade signal no matter what measuring method is employed. More specifically, it is possible to properly detect a saccade without being affected by a blink signal, by applying the filtering unit 1320 to the saccade detecting unit 211 shown in FIG. 3.

Further, when the measuring method is such that a blink signal is generated in the plus direction of an electro-oculography original signal, the filtering detail is determined such that the minimum value filtering and the maximum value filtering are performed consecutively in this order, and further that the first electro-oculography signal on which the minimum value filtering has been performed is subtracted from the second electro-oculography signal on which the maximum value filtering has been performed. As a result, it produces an advantageous effect that the saccade signal can be detected while removing the blink signal of the plus direction.

Further, in Embodiment 13, there is an advantageous effect that it is possible to detect a saccade signal including a generation time of the saccade signal by setting the number of filter taps of the maximum value filtering to be greater than the number of filter taps of the minimum value filtering.

On the other hand, when the measuring method is such that a blink signal is generated in the minus direction of an electro-oculography original signal, the filtering detail is determined such that the maximum value filtering and the minimum value filtering are performed consecutively in this order, and further that the first electro-oculography signal on which the maximum value filtering has been performed is subtracted from the second electro-oculography signal on which the minimum value filtering has been performed. As a result, it produces an advantageous effect that the saccade signal can be detected while removing the blink signal in the minus direction.

Further, in Embodiment 13, there is an advantageous effect that it is possible to detect a saccade signal including a generation time of the saccade signal by setting the number of filter taps of the minimum value filtering to be greater than the number of filter taps of the maximum value filtering.

It is to be noted that removing a blink signal, detecting a blink signal, or detecting a saccade signal has been focused on in each of the above-described Embodiments 11 to 13, and the number of the filter taps of filtering to be performed first between the minimum value filtering and the maximum value filtering has been described. The number of the filter taps may be used for removing a muscle potential, noise, and the like, by being adjusted to the temporal width of the muscle potential, the noise, and the like.

(Embodiment 14)

Figure 50:
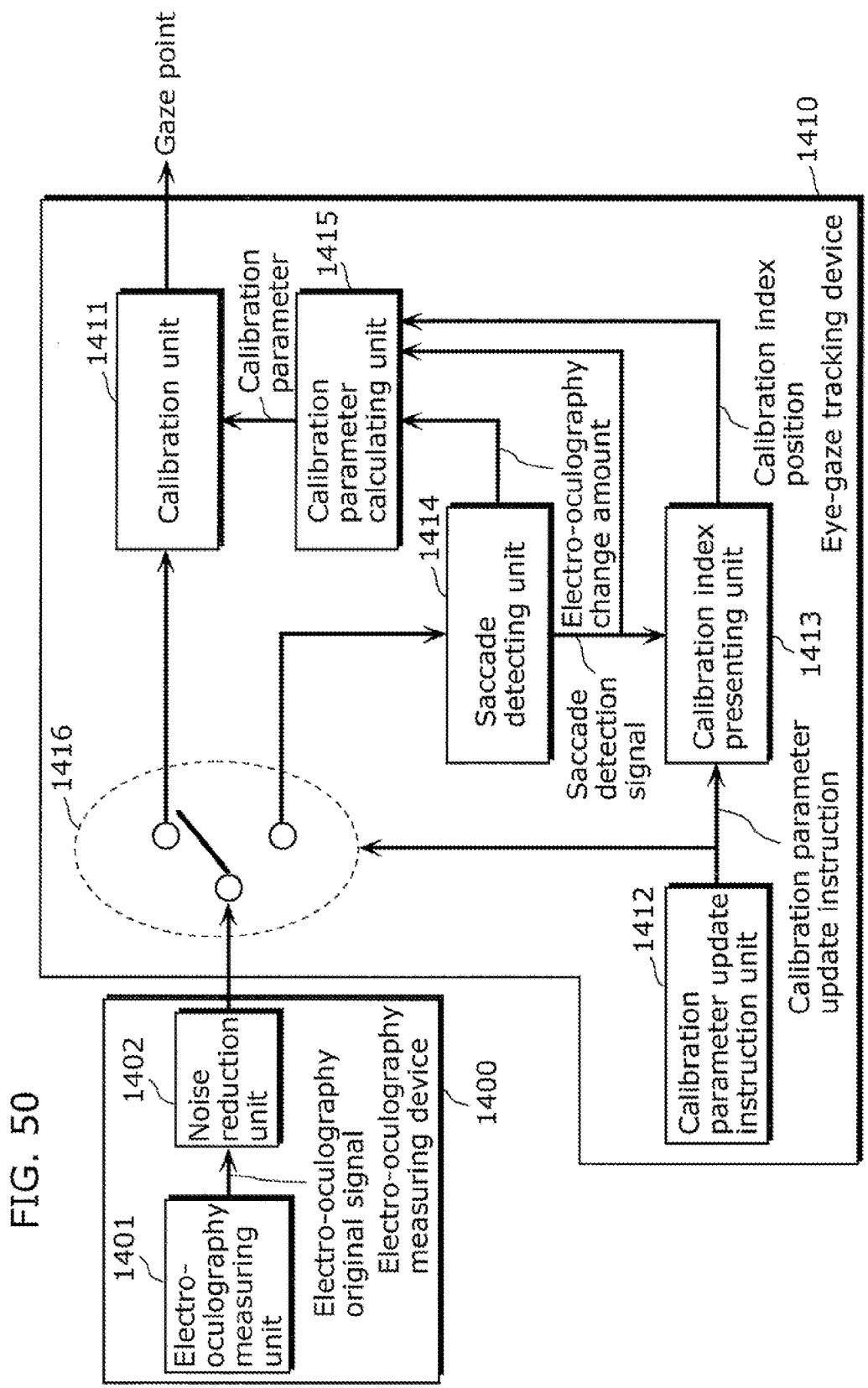
FIG. 50 is a block diagram of an eye-gaze tracking device according to Embodiment 14.

FIG. 50 is a block diagram showing a structure of an eye-gaze tracking device 1410 according to Embodiment 14 of the present invention. The eye-gaze tracking device 1410 as shown in FIG. 50 includes: an electro-oculography measuring device 1400 including an electro-oculography measuring unit 1401 placed around a user's eye to measure an electro-oculogram and output an electro-oculography original signal and a noise reduction unit 1402 that performs noise reduction processing on the electro-oculography original signal; a calibration unit 1411 that converts the electro-oculography original signal into a gaze point (which may also be referred to as "gaze path direction", hereafter the same); a calibration parameter update instruction unit 1412 that instructs update of a calibration parameter; a calibration index presenting unit 1413 that presents a calibration index in response to the calibration parameter update instruction; a saccade detecting unit 1414 that detects a saccade signal from the electro-oculography original signal; a calibration parameter calculating unit 1415 that calculates a calibration parameter based on an electro-oculography change amount output from the saccade detecting unit 1414 and a position of the calibration index output from the calibration index presenting unit 1413; and a switch 1416 that switches the output destination of the electro-oculography original signal between the calibration unit 1411 and the saccade detecting unit 1414.

For instance, the noise reduction device according to any of Embodiments 1 to 5 may be applied to the noise reduction unit 1402 in the electro-oculography measuring device 1400. Moreover, for instance, any of Embodiments 6 to 10 and 13 may be applied to the saccade detecting unit 1414.

The electro-oculography measuring unit is, typically, an electrode that is placed around an eye of a user. The placing method is not specifically limited. For example, the electrode A placed at the outer corner of the eye may be used in combination with the electrode B placed at the inner corner of the eye, as shown in FIGS. 63A and 63B. Alternatively, an electrode may be placed one or both of above and below an eye as shown in FIGS. 36A to 36D. Further, an electrode may be placed above and below a temple. Though this embodiment describes the case where the electrodes are placed around the user's eye, a method of placing the electrodes around the user's ear, a method of providing the electrodes in contact with the user's skin, and the like are also applicable.

The calibration unit 1411 calculates a gaze point of a user from the electro-oculography original signal by using a calibration parameter held in advance. Here, the calibration parameter is a parameter for converting the electro-oculography original signal into an eyeball movement angle. One of the parameters is a calibration coefficient $\alpha$ that is used in Expression 2 indicated below.

It is generally known that a measured electro-oculogram $V_{a-b}$ changes linearly when the eyeball movement angle $\theta$ is within a certain range. Therefore, the measured electro-oculogram $V_{a-b}$ can be approximated by the following Expression 2 using the calibration coefficient $\alpha$ and the eyeball movement angle $\theta$.

[Math. 2]

$$V_{a-b} = \alpha \times \theta \quad \text{(Expression 2)}$$

An example of operations of calibration using the EOG will be described. In the case where an electro-oculogram Ve is input, as an electro-oculography original signal, into the calibration unit 1411, an eyeball movement angle $\theta$ is calculated by using Expression 2. Then, a gaze point is obtained from the movement angle θ by using information such as a distance between the user and the gaze object. Through the above-described procedure, the gaze point can be obtained from the electro-oculogram. It is to be noted that the method of measuring a distance between a user and a gaze object is not specifically limited, and a distance measuring sensor and the like may be used, for example.

It is to be noted that the present invention is not limited to the calibration method using Expression 2, and a table that holds plural combinations of the electro-oculography change amount and the eyeball movement angle associated with each other as shown in FIG. 51A may be used as a calibration parameter. In addition, a table that holds plural combinations of the electro-oculogram and the gaze point such as a display coordinate, a camera coordinate, and the like associated with each other as shown in FIG. 51B may be used as a calibration parameter.

The calibration parameter update instruction unit 1412 outputs a calibration parameter update instruction signal to the calibration index presenting unit 1413 and the switch 1416 in the case where an event such as an outset of eye gaze tracking occurs. Then, when ending the update of the calibration parameter, the calibration parameter update instruction unit 1412 stops outputting the calibration parameter update instruction signal.

The switch 1416 switches between the calibration unit 1411 and the saccade detecting unit 1414 for transmitting the electro-oculography original signal, according to the calibration parameter update instruction.

The calibration index presenting unit 1413 presents a calibration index to the user, when the calibration parameter update instruction is received. Then, the calibration index presenting unit 1413 changes the position of presenting the calibration index according to the saccade detection signal from the saccade detecting unit 1414.

In the case where a display 10 as shown in FIG. 52 is used to perform calibration, for example, a first calibration index 20 is displayed at the center of the display 10 in response to receiving the calibration parameter update instruction. Then, when a saccade detection signal is received, a second calibration index 30 is displayed at the upper left. Then, when a saccade detection signal is received again, a next calibration index is displayed at the upper right and the like. As described above, it is possible to induce a saccade for a user by changing the position of the calibration index according to the saccade of the user. As described above, the position of the calibration index which is changed according to the saccade of the user is output to the calibration parameter calculating unit 1415.

It is to be noted that, although the first and second calibration indexes 20 and 30, respectively, are displayed on the display 10 in Embodiment 14, the method of presenting the calibration index is not limited to this. For example, the calibration index may be displayed on a real space by using a laser pointer and the like. Further, a calibration index may be selected from among objects (a human face and the like, for example) which exist in the surroundings by using a camera and so on to output audio information so that a user can recognize the calibration index. Thus, the calibration index presenting unit 1413 may, be any form as long as it outputs information so that a user can identify the calibration index.

The calibration parameter calculating unit 1415, when the saccade detection signal is received from the saccade detecting unit 1414, updates a calibration parameter using the electro-oculography change amount and the calibration index position. A calculation example of a calibration coefficient α that is one of calibration parameters will be described. First, an eyeball movement angle θ of a user when viewing the calibration index is calculated by using a calibration index position and distance information between the user and the object on which the calibration index is displayed (typically a display), and the like. Then, the calibration coefficient α can be obtained by substituting the electro-oculography change amount Vc and the eyeball movement angle θ which have been input, into Expression 2. It is to be noted that the method of obtaining the distance information between the user and the display is not specifically limited. For example, a distance measuring sensor or the like may be used, or the calibration parameter update instruction may be output after having a user stand at a position a predetermined distance away from the display.

Figure 53:
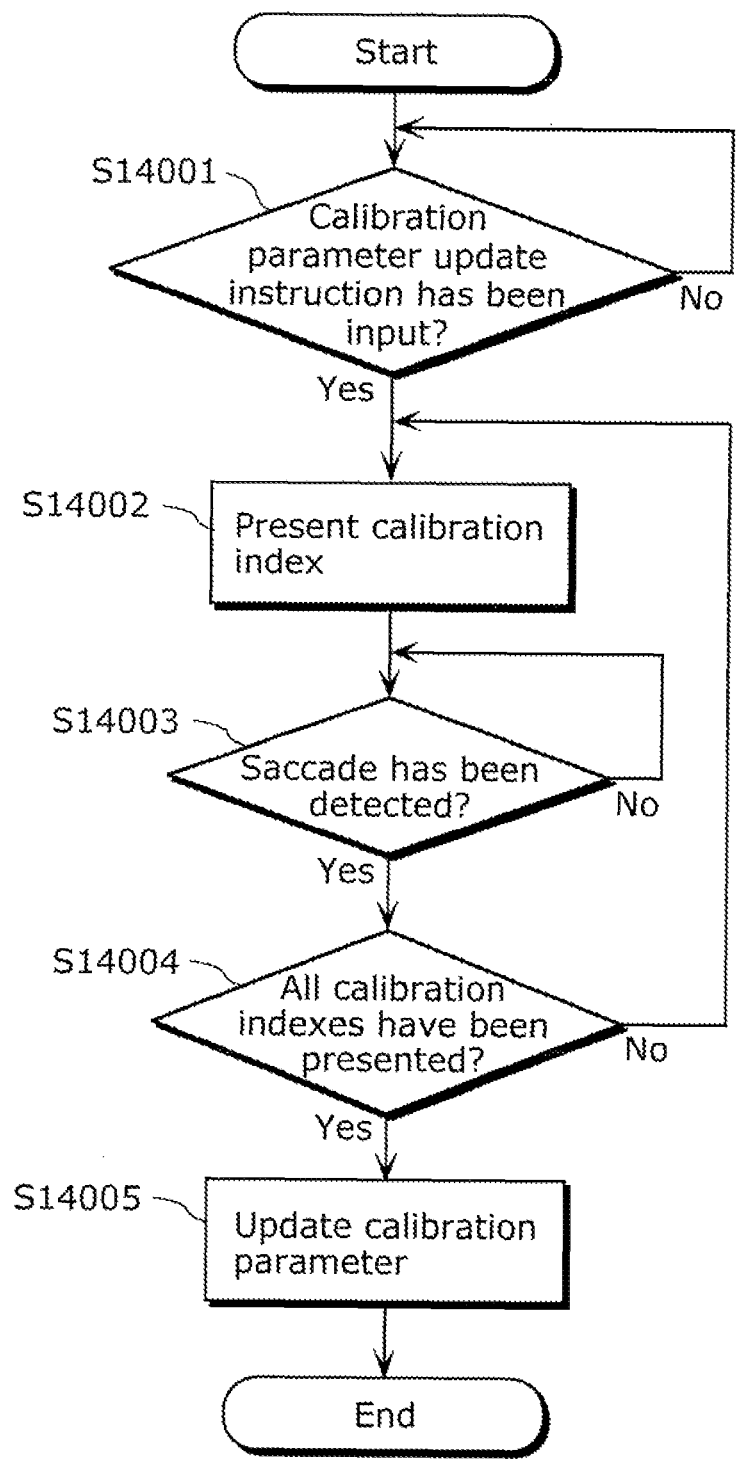
FIG. 53 is a flowchart showing an operation of the eye-gaze tracking device according to Embodiment 14.

Next, the procedure of updating the calibration parameter performed by the eye-gaze tracking device 1410 according to Embodiment 14 will be described with reference to FIG. 53. The eye-gaze tracking device 1410 calculates a new calibration parameter when triggered by an input of a calibration parameter update instruction from outside.

First, the eye-gaze tracking device 1410 monitors an input of the calibration parameter update instruction (Step S14001). The calibration parameter update instruction is transmitted from the calibration parameter update instruction unit 1412 to the calibration index presenting unit 1413 and the switch 1416. The method of inputting the calibration parameter update instruction is not specifically limited. For example, the calibration parameter update instruction unit 1412 may receive an instruction from a user or issue the instruction automatically with a predetermined timing such as the time when the power of the eye-gaze tracking device 1410 is turned on.

Next, the calibration index presenting unit 1413 which has received the calibration parameter update instruction (Yes in Step S14001) presents the first calibration index 20 to the user (Step 14002). Further, the calibration index presenting unit 1413 notifies the calibration parameter calculating unit 1415 of position information of the first calibration index 20. In a similar way, the switch 1416 which has received the calibration parameter update instruction switches the output of the electro-oculography original signal from the calibration unit 1411 to the saccade detecting unit 1414.

Next, the saccade detecting unit 1414 monitors the electro-oculography original signal that is input via the switch 1416 to see whether or not a saccade signal is included (Step S14003). When the first calibration index 20 is displayed on the display 10, the gaze-path of the user moves from an arbitrary position to the first calibration index 20. At this time, a saccade signal appears.

It is to be noted that the method of detecting a saccade signal is not specifically limited. The method includes, for example, detecting by using a maximum value filter, a minimum value filter, a delay device, and so on. The details will be described later. When a saccade signal is detected (Yes in Step 14003), the saccade detecting unit 1414 outputs a saccade detection signal to the calibration index presenting unit 1413. In a similar way, the saccade detecting unit 1414 outputs the saccade detection signal and the electro-oculography change amount $V_{a-b}$ to the calibration parameter calculating unit 1415.

Next, the calibration index presenting unit 1413 which has received the saccade detection signal determines whether or not all calibration indexes have been presented to the user (Step S14004).

The number of calibration indexes to be presented may be specified in advance, or whether or not to continue presenting the calibration indexes may be asked to the user. It is to be noted that the number of the calibration indexes to be presented is assumed to be two in the description of Embodiment 14.

At this point, only the first calibration index 20 is presented (No in Step S14004), and thus the calibration index presenting unit 1413 presents the next calibration index (Step S14002). More specifically, the first calibration index 20 is deleted from the display 10 and the second calibration index 30 is displayed on the display 10. Further, the calibration index presenting unit 1413 notifies the calibration parameter calculating unit 1415 of the position information of the second calibration index 30.

Next, the saccade detecting unit 1414 monitors the electro-oculography original signal to see whether or not a saccade signal is included (Step 14003). When the second calibration index 30 is displayed on the display 10, the gaze-path of the user moves from the first calibration index 20 to the second calibration index 30. At this time, a saccade signal appears.

The saccade detecting unit 1414 which has detected the saccade signal outputs the saccade detection signal and the electro-oculography change amount $V_{a-b}$ in the same manner as the previous time. Further, after the second calibration index 30 is presented, the calibration index presenting unit 1413, in Step S14004, determines that all of the calibration indexes have been presented (Yes in Step S14004).

Next, the calibration parameter calculating unit 1415 calculates a new calibration parameter based on the position information of the first and the second calibration indexes 20 and 30 received from the calibration index presenting unit 1413 and the electro-oculography change amount $V_{a-b}$ after the output of the second calibration index 30, which has been received from the saccade detecting unit 1414. More specifically, an eyeball movement angle θ is calculated using the position information of the first and the second calibration indexes 20 and 30. Then, the electro-oculography change amount $V_{a-b}$ and the eyeball movement angle θ are substituted into Expression 2 to obtain a calibration coefficient α.

It is to be noted that the method of calculating the calibration coefficient α is described as an example of updating a calibration parameter in Embodiment 14. However, the method of updating the calibration parameter is not limited to this. For example, it is also possible to use the electro-oculography change amount, the eyeball movement angle, or the calibration index position which have been input to the calibration parameter calculating unit 1415 to update a table holding plural combinations of the electro-oculography change amount and a corresponding eyeball movement angle or a gaze-path position as shown in FIGS. 51A and 51B. In this case, the number of records of the tables in FIGS. 51A and 51B increases by increasing the total number of the calibration indexes to be presented, and thus it is possible to obtain a more reliable calibration parameter.

According to the structure of Embodiment 14 as described above, noise is reduced from the electro-oculography original signal, the saccade signal is detected from the electro-oculography original signal that has been improved in S/N ratio, and the calibration parameter is updated using the amount of change in electro-oculogram occurring during a saccadic movement. As a result, the calibration parameter can be properly obtained without being affected by a drift which has been a problem of conventional methods.

Moreover, the S/N ratio of the electro-oculography original signal is improved as a result of noise reduction in the electro-oculography measuring device, which contributes to improved eye-gaze tracking accuracy.

Further, it is possible to update a calibration parameter while inducing a saccade of a user. As a result, the user only has to follow a calibration index with his/her eyes, and thus it is possible to reduce the burden of the user at the time of calibration.

Further, it is also possible to reduce a calibrate time by holding the calibration parameter as a table as shown in FIGS. 51A and 51B.

Further, it is possible to reduce a memory by holding the calibration parameter as a slope of function (calibration coefficient α) of the electro-oculography change amount $V_{a-b}$ and the eyeball movement angle θ.

Figure 54:
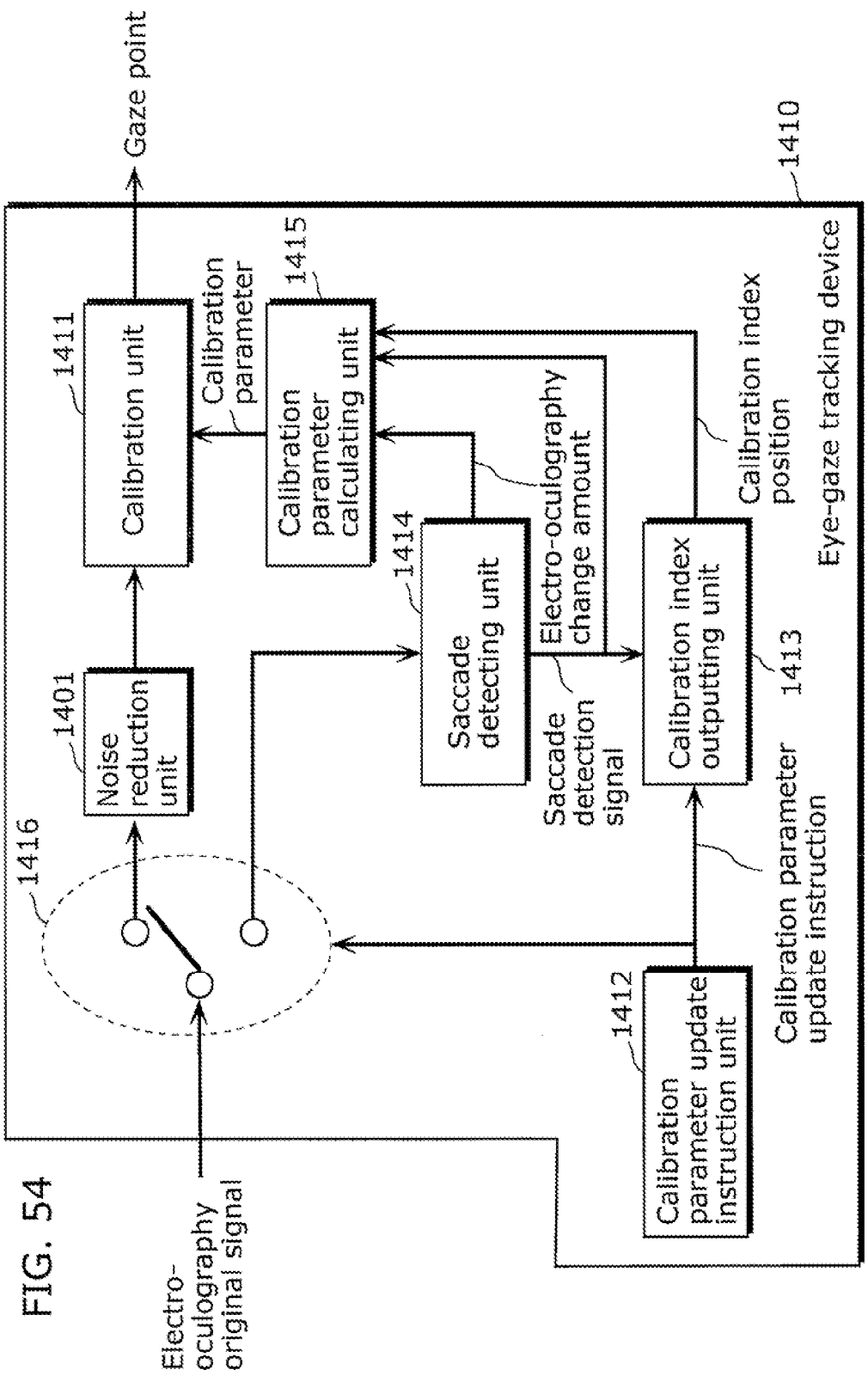
FIG. 54 is a diagram showing another structure of the eye-gaze tracking device according to Embodiment 14.
Figure 55:
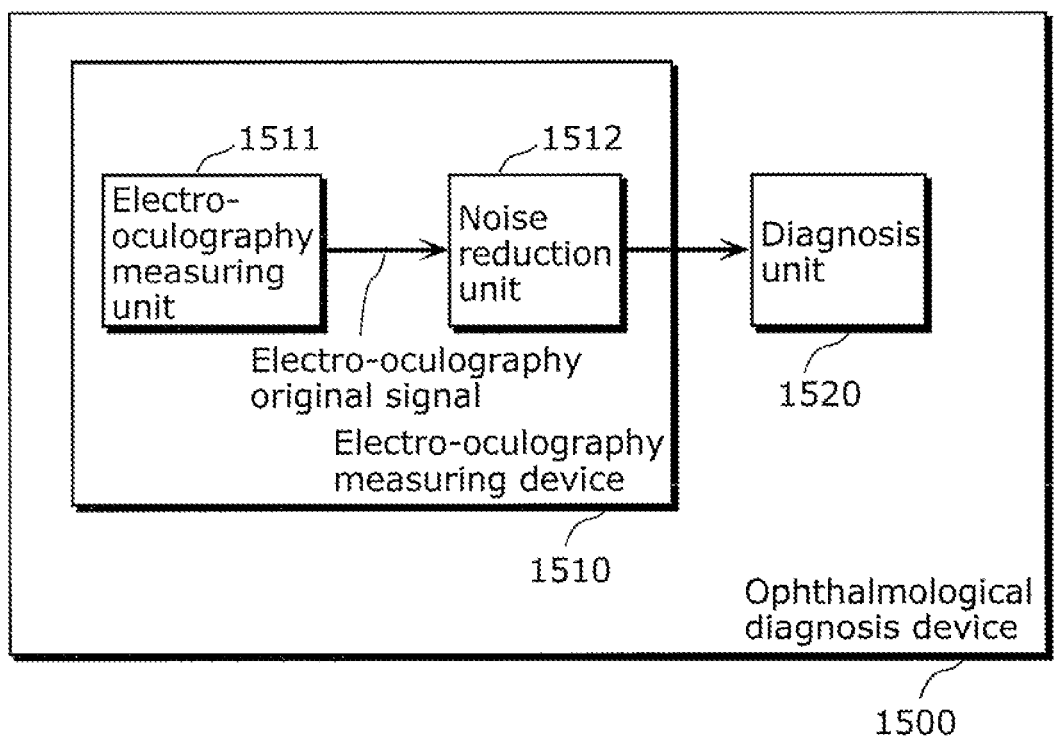
FIG. 55 is a block diagram of an ophthalmological diagnosis device according to Embodiment 15.

Note that the noise reduction unit 1401 of the electro-oculography measuring device 1400 may be included in the eye-gaze tracking device 1410, as shown in FIG. 54. Including the noise reduction unit 1401 in the eye-gaze tracking device 1410 allows the saccade information used in the noise reduction unit 1401 to be obtained from the saccade detecting unit 1414, which contributes to reduced processing amount and circuit size.

(Embodiment 15)

The following describes an ophthalmological diagnosis device 1500 according to Embodiment 15 of the present invention. For example, the ophthalmological diagnosis device 1500 is a device that diagnoses abnormality of a retinal standing potential by measuring an electro-oculogram from electrodes placed around the user's eye. In detail, the ophthalmological diagnosis device 1500 includes: an electro-oculography measuring device 1510 including an electro-oculography measuring unit 1511 that is placed around the user's eye to measure an electro-oculogram and output an electro-oculography original signal, and a noise reduction unit 1512 that performs noise reduction processing on the electro-oculography original signal; and a diagnosis unit 1520.

As an example, the diagnosis unit 1520 may calculate an Arden ratio which is a ratio between an electro-oculography signal during light adaptation and an electro-oculography signal during dark adaptation, and diagnosis a retinal state from abnormality of the Arden ratio. For instance, the noise reduction device according to any of Embodiments 1 to 5 may be applied to the noise reduction unit 1512 in the electro-oculography measuring device 1510.

Note that the electro-oculography measuring device 1510 according to Embodiment 15 is not limited to the above use. The electro-oculography measuring device 1510 may also be applied to a device that performs switching according to the amount of change in electro-oculogram, or a remote control operation of a mobile terminal such as a music player, a mobile phone, and so on.

Though this embodiment describes the case where the electrodes are placed around the user's eye, a method of placing the electrodes around the user's ear, a method of providing the electrodes in contact with the user's skin, and the like are also applicable.

(Embodiment 16)

Figure 56:
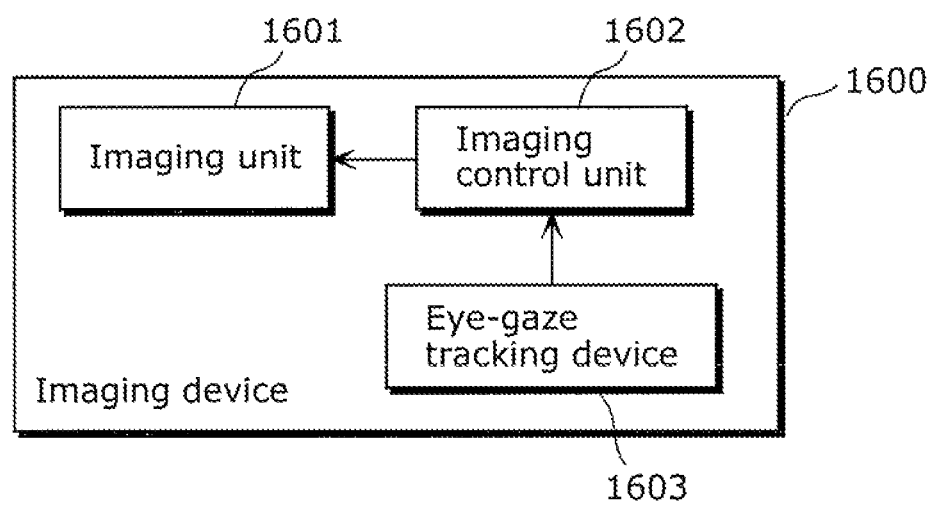
FIG. 56 is a block diagram of an imaging device according to Embodiment 16.
Figure 57:
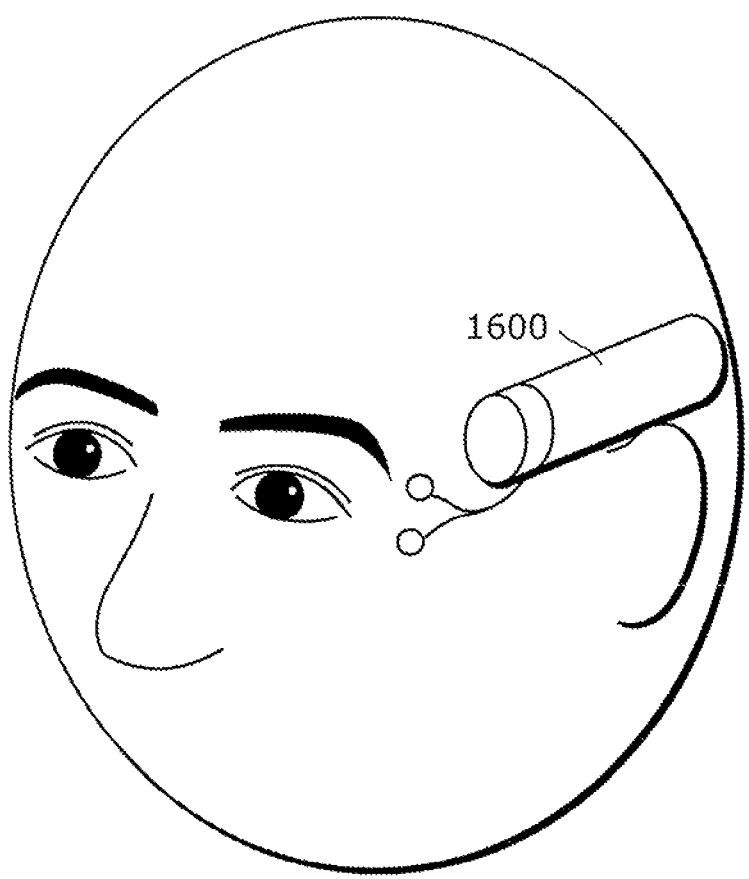
FIG. 57 is a diagram showing a state where a user wears the imaging device according to Embodiment 16.

The following describes an imaging device 1600 according to Embodiment 16 of the present invention, with reference to FIGS. 56 and 57. For example, the imaging device 1600 is a device that is worn by the user on the side of his/her head, and captures an image in the gaze-path direction of the user. In detail, the imaging device 1600 includes an imaging unit 1601, an imaging control unit 1602, and an eye-gaze tracking device 1603.

As an example, the imaging device 1600 may be a camera that captures a still image, or a video camera that captures a moving image. For instance, the eye-gaze tracking device 1410 according to Embodiment 14 may be applied to the eye-gaze tracking device 1600. Electrodes as an electro-oculography measuring unit in Embodiment 16 are placed above and below the user's left temple, as shown in FIG. 57.

The imaging control unit 1602 monitors an output signal of the eye-gaze tracking device 1603, and changes an orientation of the imaging unit 1601 according to the gaze-path movement of the user. This enables the imaging unit 1601 to capture an image in the gaze-path direction of the user.
(Embodiment 17)

Figure 58:
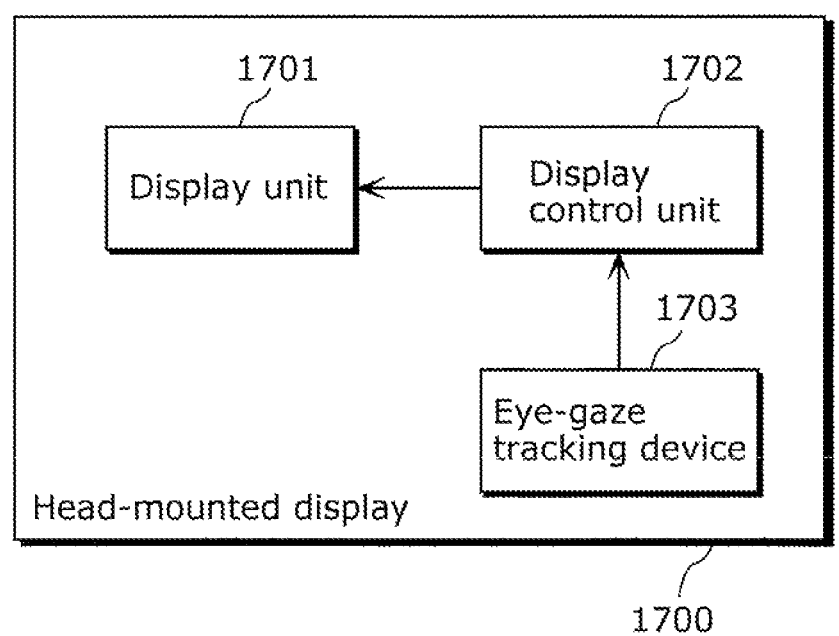
FIG. 58 is a block diagram of a head-mounted display according to Embodiment 17.
Figure 59:
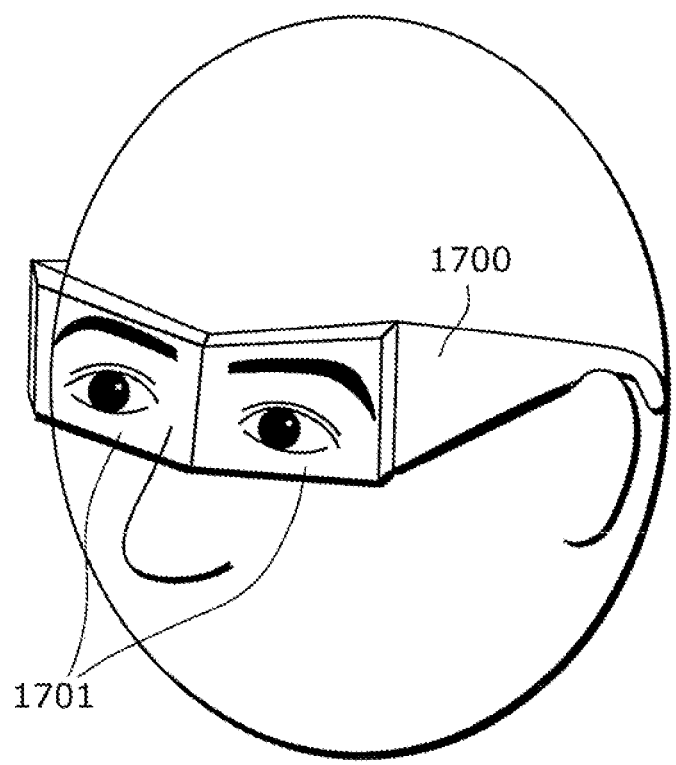
FIG. 59 is a diagram showing a state where the user wears the head-mounted display according to Embodiment 17.

The following describes a head-mounted display 1700 according to Embodiment 17 of the present invention, with reference to FIGS. 58 and 59. For example, the head-mounted display 1700 is an eyeglass-type device that displays an image in front of the user's eye, and moves a mouse pointer appearing on the displayed image in the gaze-path direction of the user. In detail, the head-mounted display 1700 includes a display unit 1701, a display control unit 1702, and an eye-gaze tracking device 1703.

Figure 60:
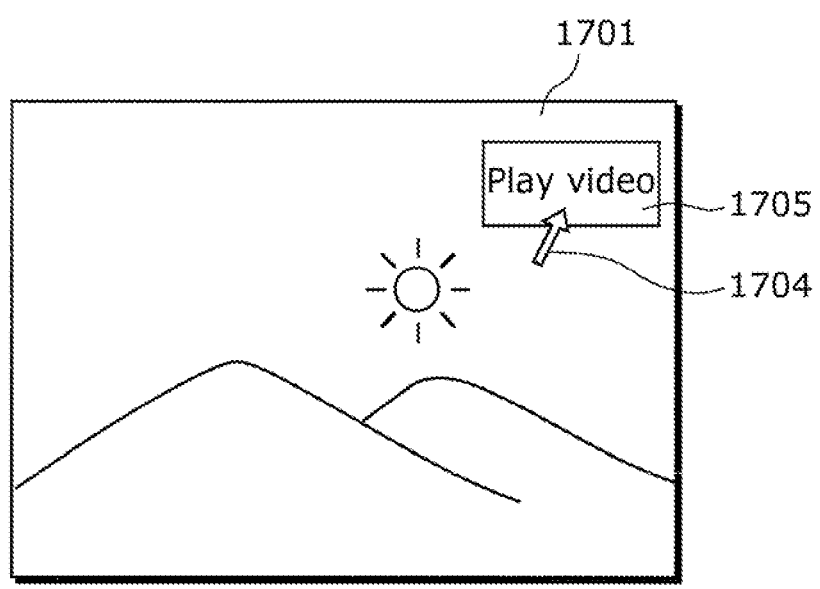
FIG. 60 is a diagram showing an example of an image displayed on a display unit of the head-mounted display according to Embodiment 17.

Suppose one of various images is displayed on the display unit 1701, with a mouse pointer 1704 appearing on the displayed image, as shown in FIG. 60. For instance, the eye-gaze tracking device 1410 according to Embodiment 14 may be applied to the eye-gaze tracking device 1703.

The display control unit 1702 monitors an output signal of the eye-gaze tracking device 1703, and moves the mouse pointer 1704 displayed on the display unit 1701 according to the user's gaze-path movement. This enables, for example, a processing unit (not shown) to execute a process (video playback in the example of FIG. 60) corresponding to an icon 1705 pointed at with the mouse pointer 1704.
(Embodiment 18)

Figure 61:
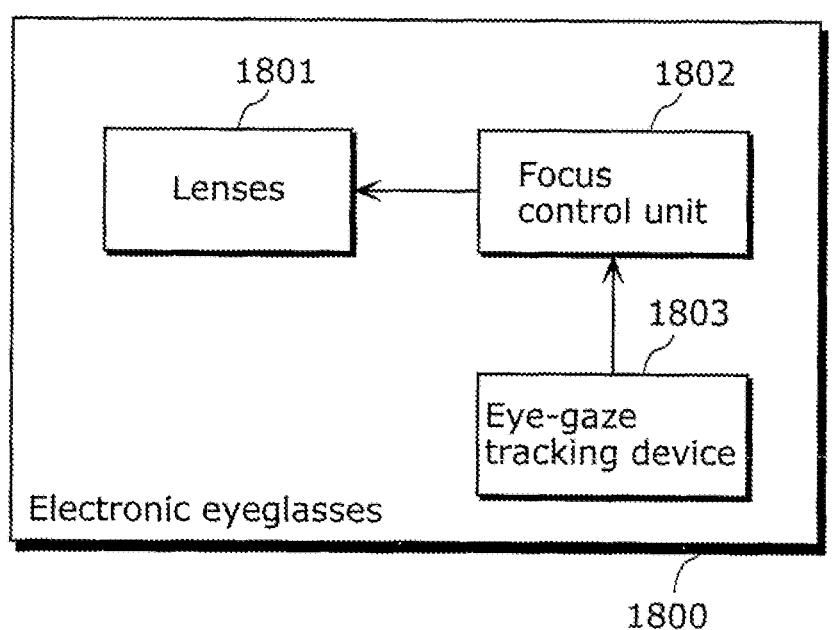
FIG. 61 is a block diagram of electronic eyeglasses according to Embodiment 18.
Figure 62:
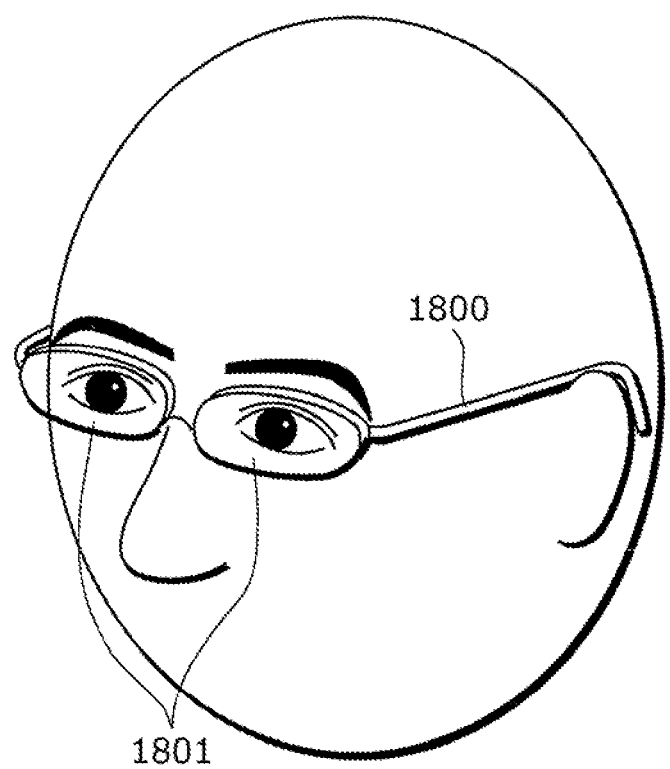
FIG. 62 is a diagram showing a state where the user wears the electronic eyeglasses according to Embodiment 18.

The following describes electronic eyeglasses 1800 according to Embodiment 18 of the present invention, with reference to FIGS. 61 and 62. The electronic eyeglasses 1800 are eyeglasses that can change a focus of each lens according to the gaze point of the user. In detail, the electronic eyeglasses 1800 include lenses 1801, a focus control unit 1802, and an eye-gaze tracking device 1803.

Each lens 1801 is located in front of an eye of the user, and has an electronically changeable focus.

For instance, the eye-gaze tracking device 1410 according to Embodiment 14 may be applied to the eye-gaze tracking device 1803.

The focus control unit 1802 monitors an output signal of the eye-gaze tracking device 1803, and changes the focus of each lens 1801 according to the user's gaze-path movement. For example, in the case where the user is watching a near object such as when reading a book, the focus control unit 1802 controls the focus of each lens 1801 so as to converge to the near object. In the case where the user is watching a far landscape, on the other hand, the focus control unit 1802 controls the focus of each lens 1801 so as to converge to the far landscape.

In this embodiment, the right and left eyes of the user are assumed to gaze at the same point. Thus, the eye-gaze tracking device 1803 can detect the gaze point from the electro-oculogram.

Note that the eye-gaze tracking device 1410 according to Embodiment 14 is not limited to the above use. The eye-gaze tracking device 1410 may also be applied to a device that plots the user's gaze point detected by the eye-gaze tracking device 1410 on an image captured by an imaging device, a device that detects the driver's gaze point during driving and alerts the driver, and so on.

Although the present invention has been described by way of the above embodiments, the present invention is not limited to the above embodiments. The present invention also includes the following variations.

Each of the above devices is actually a computer system that includes a microprocessor, a ROM, a RAM, a hard disk unit, a display unit, a keyboard, a mouse, and the like. A computer program is stored on the RAM or the hard disk unit. Functions of each of the devices can be achieved by the microprocessor operating in accordance with the computer program. The computer program mentioned here is a combination of a plurality of instruction codes that represent instructions to a computer for achieving predetermined functions.

The components that constitute each of the above devices may be partly or wholly realized by one system LSI (Large Scale Integration). The system LSI is an ultra-multifunctional LSI produced by integrating a plurality of components on one chip, and is actually a computer system that includes a microprocessor, a ROM, a RAM, and the like. A computer program is stored on the RAM. Functions of the system LSI can be achieved by the microprocessor operating in accordance with the computer program.

The components that constitute each of the above devices may be partly or wholly realized by an IC card or a single module that is removably connectable to the device. The IC card or the module is a computer system that includes a microprocessor, a ROM, a RAM, and the like. The IC card or the module may include the above-mentioned ultra-multifunctional LSI. Functions of the IC card or the module can be achieved by the microprocessor operating in accordance with the computer program. The IC card or the module may be tamper resistant.

The present invention may also be the method described above. The present invention may also be a computer program that realizes the method by a computer. The present invention may also be a digital signal formed by the computer program.

The present invention may also be a computer-readable recording medium, such as a flexible disk, a hard disk, a CD-ROM, an MO, a DVD, a DVD-ROM, a DVD-RAM, a Blu-ray Disc (BD), or a semiconductor memory, on which the computer program or the digital signal is recorded. Conversely, the present invention may be the digital signal recorded on such a recording medium.

The present invention may also be the computer program or the digital signal transmitted via a network such as an electric communication line, a wired or wireless communication line, or the Internet, data broadcasting, and the like.

The present invention may also be a computer system that includes a microprocessor and a memory. In this case, the computer program can be stored in the memory, with the microprocessor operating in accordance with the computer program.

The computer program or the digital signal may be provided to another independent computer system by distributing the recording medium on which the computer program or the digital signal is recorded, or by transmitting the computer program or the digital signal via the network and the like. The independent computer system may then execute the computer program or the digital signal to function as the present invention.

The above embodiments and variations may be freely combined.

Though the embodiments of the present invention have been described with reference to the drawings, the present invention is not limited to the illustrated embodiments. Various modifications and changes can be made to the illustrated embodiments within the same or equivalent scope of the present invention.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

The present invention is useful, for example, as an apparatus for recording and reproducing video and audio in fields such as broadcasting, communication, and storage. The present invention is also applicable as a still image recording and reproduction apparatus and the like. The present invention is also applicable as health-care equipment.

What is claimed is:

1. A noise reduction device comprising:
a saccade information obtaining unit configured to obtain saccade information from an electro-oculography original signal that indicates an electro-oculogram resulting from an eye movement of a user, the saccade information relating to a saccadic movement which is a rapid eyeball movement;
a control unit configured to determine a filter property for reducing noise included in the electro-oculography original signal, on the basis of the saccade information obtained by said saccade information obtaining unit; and
a filtering unit configured to reduce the noise included in the electro-oculography original signal using the filter property determined by said control unit, to output an electro-oculography signal,
wherein said filtering unit includes a high pass filter,
wherein said saccade information obtaining unit includes a saccade detecting unit configured to output a saccade detection signal in the case where a saccade signal indicating the saccadic movement is included in the electro-oculography original signal,
wherein said control unit is configured to change a cutoff frequency of the high pass filter according to the saccade detection signal, and
wherein said filtering unit is configured to output the electro-oculography original signal using, as the filter property, the cutoff frequency having a value obtained by said control unit changing the cutoff frequency according to the saccade detection signal.

2. The noise reduction device according to claim 1,
wherein said saccade information obtaining unit includes a time interval calculating unit configured to calculate, as the saccade information, a time interval of temporally adjacent saccade detection signals output from said saccade detecting unit, and
wherein said control unit is configured to (i) increase the cutoff frequency in the case where the time interval is equal to or smaller than a first value, and (ii) decrease the cutoff frequency in the case where the time interval is larger than the first value.

3. The noise reduction device according to claim 1,
wherein said saccade information obtaining unit includes an occurrence frequency calculating unit configured to calculate, as the saccade information, an occurrence frequency of the saccade detection signal output from said saccade detecting unit, and
wherein said control unit is configured to (i) increase the cutoff frequency in the case where the occurrence frequency is larger than a second value, and (ii) decrease the cutoff frequency in the case where the occurrence frequency is equal to or smaller than the second value.

4. The noise reduction device according to claim 2,
wherein the noise is drift noise which is a change of a base line of the electro-oculography original signal with time, and
wherein said control unit is configured to change the cutoff frequency within a range from 0 to a maximum frequency of the drift noise.

5. The noise reduction device according to claim 1,
wherein said filtering unit includes a low pass filter,
wherein said saccade information obtaining unit includes a non-occurrence area specifying unit configured to specify a non-occurrence area on the basis of the saccade detection signal output from said saccade detecting unit, the non-occurrence area being a temporally continuous area which includes a sample subject to filtering by said filtering unit and in which no saccadic movement occurs, and
wherein said control unit is configured to set a filter coefficient of a sample not included in the non-occurrence area to 0.

6. The noise reduction device according to claim 1,
wherein said filtering unit includes a low pass filter,
wherein said saccade detecting unit is configured to output, in the case where the saccade signal indicating the saccadic movement is included in the electro-oculography original signal, an amplitude of the saccade signal; and
wherein said saccade information obtaining unit includes a non-occurrence probability calculating unit configured to calculate a non-occurrence probability for each sample input to said filtering unit, according to the amplitude detected by said saccade detecting unit, the non-occurrence probability being a probability that no saccade occurs in a position of the sample, and
wherein said control unit is configured to set a larger filter coefficient for a sample having a higher non-occurrence probability.

7. The noise reduction device according to claim 2,
wherein said saccade detecting unit includes:
a delayed signal generating unit configured to generate a delayed signal by delaying the electro-oculography original signal by a predetermined amount of time;
a subtraction unit configured to generate an output signal obtained by subtracting the delayed signal from the electro-oculography original signal; and
a saccade determining unit configured to determine a signal, in the output signal, that exceeds a predetermined threshold, as the saccade signal indicating the saccadic movement.

8. The noise reduction device according to claim 7,
wherein the predetermined amount of time is shorter than an amount of time of visual fixation by the user on a calibration index.

9. The noise reduction device according to claim 2,
wherein said saccade detecting unit includes:
a first filtering unit configured to perform one of maximum value filtering and minimum value filtering on the electro-oculography original signal, to output a first electro-oculography signal;
a subtraction unit configured to generate an output signal by subtracting, from one of the first electro-oculography signal and a second electro-oculography signal, an other one of the first electro-oculography signal and the second electro-oculography signal, the second electro-oculography signal being obtained from the electro-oculography original signal; and a saccade determining unit configured to determine a signal, in the output signal, that exceeds a predetermined threshold, as the saccade signal indicating the saccadic movement.

10. The noise reduction device according to claim 9, wherein said saccade detecting unit further includes a second filtering unit configured to perform an other one of the maximum value filtering and the minimum value filtering on the electro-oculography original signal, to output the second electro-oculography signal.

11. The noise reduction device according to claim 9, wherein said saccade detecting unit further includes a second filtering unit configured to perform an other one of the maximum value filtering and the minimum value filtering on the first electro-oculography signal, to output the second electro-oculography signal.

12. The noise reduction device according to claim 7, further comprising
a synthesized signal generating unit configured to generate a synthesized signal by averaging the electro-oculography original signal measured through each of a plurality of channels, for each group to which the plurality of channels belong, and differential-amplifying an average value of each group,
wherein said saccade detecting unit is configured to detect a saccade included in the synthesized signal.

13. An electro-oculography measuring device comprising:
an electro-oculography measuring unit configured to output an electro-oculography original signal that indicates an electro-oculogram resulting from an eye movement; and
the noise reduction device according to claim 1 that reduces noise included in the electro-oculography original signal.

14. An ophthalmological diagnosis device that diagnoses a retinal state of a user, said ophthalmological diagnosis device comprising:
the electro-oculography measuring device according to claim 13; and
a diagnosis unit configured to detect retinal abnormality of the user from an electro-oculography signal output from said electro-oculography measuring device.

15. An eye-gaze tracking device that detects a gaze-path direction of a user from an electro-oculography signal, said eye-gaze tracking device comprising:
the electro-oculography measuring device according to claim 13;
a calibration index presenting unit configured to present a calibration index to the user;
a saccade detecting unit configured to detect a saccadic movement from the electro-oculography signal and output an electro-oculography change amount, the saccadic movement being a rapid eyeball movement that occurs when a gaze point of the user moves to the calibration index presented by said calibration index presenting unit, and the electro-oculography change amount being an amount of change in electro-oculogram before or after the saccadic movement;
a calibration parameter calculating unit configured to calculate a calibration parameter, on the basis of a position of the calibration index presented by said calibration index presenting unit and the electro-oculography change amount output from said saccade detecting unit; and
a calibration unit configured to detect the gaze-path direction of the user from the electro-oculography signal, on the basis of the calibration parameter.

16. A wearable camera that captures an image in a gaze-path direction of a user, said wearable camera comprising:
an imaging unit;
the eye-gaze tracking device according to claim 15; and
an imaging control unit configured to cause said imaging unit to capture an image in a gaze-path direction detected by said eye-gaze tracking device.

17. A head-mounted display that moves a mouse pointer in a gaze-path direction of a user, said head-mounted display comprising:
a display unit configured to display an image and the mouse pointer;
the eye-gaze tracking device according to claim 15; and
a display control unit configured to move the mouse pointer displayed by said display unit, in a gaze-path direction detected by said eye-gaze tracking device.

18. Electronic eyeglasses that change a focus of each of lenses according to a gaze point of a user, said electronic eyeglasses comprising:
lenses each having a changeable focus;
the eye-gaze tracking device according to claim 15; and
a focus control unit configured to change the focus of each of said lenses according to a gaze point detected by said eye-gaze tracking device.

19. The noise reduction device according to claim 1, wherein said control unit is configured to change the cutoff frequency according to the saccade detection signal so that the cutoff frequency has a greater value as the saccade detection signal is output more frequently.

20. A noise reduction method comprising:
obtaining saccade information from an electro-oculography original signal that indicates an electro-oculogram resulting from an eye movement of a user, the saccade information relating to a saccadic movement which is a rapid eyeball movement;
determining a filter property for reducing noise included in the electro-oculography original signal, on the basis of the saccade information obtained in said obtaining;
reducing, using a high filter, the noise included in the electro-oculography original signal using the filter property determined in said determining, to output an electro-oculography signal; and
outputting a saccade detection signal in the case where a saccade signal indicating the saccadic movement is included in the electro-oculography original signal,
wherein said determining includes changing a cutoff frequency of the high pass filter according to the saccade detection signal, and
wherein said reducing outputs the electro-oculography original signal using, as the filter property, the cutoff frequency changed in said determining according to the saccade detection signal.

21. A non-transitory computer-readable recording medium for use in a computer, said recording medium having a computer program recorded thereon for causing the computer to execute:
obtaining saccade information from an electro-oculography original signal that indicates an electro-oculogram resulting from an eye movement of a user, the saccade information relating to a saccadic movement which is a rapid eyeball movement;
determining a filter property for reducing noise included in the electro-oculography original signal, on the basis of the saccade information obtained in said obtaining;
reducing, using a high pass filter, the noise included in the electro-oculography original signal using the filter property determined in said determining, to output an electro-oculography signal; and outputting a saccade detection signal in the case where a saccade signal indicating the saccadic movement is included in the electro-oculography original signal, wherein said determining includes changing a cutoff frequency of the high pass filter according to the saccade detection signal, and wherein said reducing outputs the electro-oculography original signal using, as the filter property, the cutoff frequency changed in said determining according to the saccade detection signal.

* * * * *